US008580784B2

(12) United States Patent
Matsuda et al.

(10) Patent No.: US 8,580,784 B2
(45) Date of Patent: Nov. 12, 2013

(54) METHOD FOR TREATING A DISEASE RELATED TO THE GLUCOCORTICOID RECEPTOR

(75) Inventors: Mamoru Matsuda, Ikoma (JP); Masato Nagatsuka, Ikoma (JP); Toshiyuki Mori, Ikoma (JP); Sachiko Kobayashi, Ikoma (JP); Masatomo Kato, Ikoma (JP); Miwa Takai, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 10 days.

(21) Appl. No.: 13/135,765

(22) Filed: Jul. 14, 2011

(65) Prior Publication Data

US 2011/0275632 A1 Nov. 10, 2011

Related U.S. Application Data

(63) Continuation of application No. 12/312,396, filed as application No. PCT/JP2007/072082 on Nov. 14, 2007, now Pat. No. 8,008,498.

(30) Foreign Application Priority Data

Nov. 14, 2006 (JP) ................................. 2006-307651

(51) Int. Cl.
*A61K 31/5377* (2006.01)
(52) U.S. Cl.
USPC ...................................... 514/235.2; 514/314
(58) Field of Classification Search
USPC ............................................ 514/235.2, 314
See application file for complete search history.

(56) References Cited

U.S. PATENT DOCUMENTS

| 5,688,808 | A | 11/1997 | Jones et al. |
| 5,688,810 | A | 11/1997 | Jones et al. |
| 5,693,646 | A | 12/1997 | Jones et al. |
| 5,693,647 | A | 12/1997 | Jones et al. |
| 5,696,127 | A | 12/1997 | Jones et al. |
| 5,696,130 | A | 12/1997 | Jones et al. |
| 5,696,133 | A | 12/1997 | Jones et al. |
| 5,994,544 | A | 11/1999 | Jones et al. |
| 6,093,821 | A | 7/2000 | Jones et al. |
| 6,121,450 | A | 9/2000 | Jones et al. |
| 6,448,405 | B1 | 9/2002 | Jones et al. |
| 6,696,459 | B1 | 2/2004 | Jones et al. |
| 6,852,719 | B2 | 2/2005 | Liu et al. |
| 6,858,627 | B2 | 2/2005 | Bekkali et al. |
| 7,799,782 | B2 * | 9/2010 | Munson et al. ............ 514/234.5 |
| 2004/0014741 | A1 | 1/2004 | Liu et al. |
| 2004/0116455 | A1 | 6/2004 | Bekkali et al. |
| 2004/0186132 | A1 | 9/2004 | Jones et al. |
| 2007/0254917 | A1 | 11/2007 | Higuchi et al. |
| 2009/0298826 | A1 | 12/2009 | Matsuda et al. |
| 2009/0326009 | A1 | 12/2009 | Matsuda et al. |
| 2010/0056504 | A1 | 3/2010 | Matsuda et al. |
| 2011/0118260 | A1 | 5/2011 | Kato et al. |

FOREIGN PATENT DOCUMENTS

| EP | 1 944 290 A1 | 7/2008 |
| JP | 10-510840 A | 10/1998 |
| JP | 2002-193955 A | 7/2002 |
| RU | 2004135304 A | 7/2005 |
| WO | WO 96/19458 A2 | 6/1996 |
| WO | WO 96/19458 A3 | 6/1996 |
| WO | WO 03/093237 A1 | 11/2003 |
| WO | WO 2004/018429 A2 | 3/2004 |
| WO | WO 2006/019716 A1 | 2/2006 |
| WO | WO 2007/032556 A1 | 3/2007 |
| WO | WO 2008/111632 A1 | 9/2008 |

OTHER PUBLICATIONS

Hajime Nawata, Sougou Rinsyou, "New horizon of glucocorticoid therapy in 21st century," 54(7), 1951-2076 (2005).
Ku, Yi-Yin; Grieme, Tim; Raje, Prasad; Sharma, Padam; King, Steve; Morton, Edward: "Asymmetric Synthesis of A-240610.0 via a New Atropselective Approach for Axially Chiral Biaryls with Chirality Transfer," Journal of the American Chemical Society, vol. 124, 2002, pp. 4282-4286.
Supplementary European Search Report dated Nov. 4, 2010 in European application No. EP 07 83 1812.
International Search Report for PCT/JP2007/072082 dated Jan. 29, 2008.
Igaku Daijiten, Nanzando, the 17th edition, pp. 1038-1040 (including English-language translation as attached pp. 1-10), 1996.

* cited by examiner

*Primary Examiner* — Rei-tsang Shiao
(74) *Attorney, Agent, or Firm* — Holtz Holtz Goodman & Chick, PC

(57) ABSTRACT

A method for preventing or treating a disease related to the glucocorticoid receptor involving administering a pharmacologically effective amount of a 1,2-dihydroquinoline compound.

7 Claims, No Drawings

METHOD FOR TREATING A DISEASE RELATED TO THE GLUCOCORTICOID RECEPTOR

CROSS-REFERENCE TO RELATED APPLICATIONS

This application is a continuation application of application Ser. No. 12/312,396 filed May 7, 2009 (U.S. Pat. No. 8,008,498), which is the United States national phase application under 35 USC 371 of International application PCT/JP2007/072082 filed Nov. 14, 2007. The entire contents of each of application Ser. No. 12/312,396 and International application PCT/JP2007/072082 are hereby incorporated by reference herein.

TECHNICAL FIELD

The present invention relates to novel 1,2-dihydroquinoline derivatives having substituted phenylamino lower alkyl group and ester-introduced phenyl group as substituents or a salt thereof, which are useful as pharmaceuticals. The derivatives have glucocorticoid receptor binding activity and are useful as glucocorticoid receptor modulators having a non-steroidal structure (glucocorticoid receptor agonists and/or glucocorticoid receptor antagonists).

BACKGROUND ART

A glucocorticoid receptor is a 94 kDa ligand-activated intracellular transcriptional regulatory factor that is a member of the nuclear receptor superfamily. This receptor is known to affect the regulation of the metabolism of carbohydrates, proteins, fats and the like, suppression of the immune or inflammatory responses, activation of the central nervous system, regulation of cardiovascular function, and basal and stress-related homeostasis and the like due to its transcriptional regulatory action. As diseases which are considered to be related to glucocorticoid receptor, metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like are known (SOUGOU RINSYOU, 54(7), 1951-2076 (2005), JP-A-2002-193955). Therefore, a compound having a glucocorticoid receptor binding activity is useful as a preventive and/or therapeutic agent for these diseases.

As such a compound having a glucocorticoid receptor binding activity, glucocorticoid receptor agonists synthesized in the living body such as cortisol and corticosterone, synthetic glucocorticoid receptor agonists such as dexamethasone, prednisone and prednisilone, non-selective glucocorticoid receptor antagonists such as RU486 and the like are known (JP-A-2002-193955).

On the other hand, compounds having a 1,2-dihydroquinoline structure are disclosed as steroid receptor modulators in WO 2004/018429, JP-T-10-0510840, WO 2006/019716 and the like. In WO 2004/018429, JP-T-10-0510840 and WO 2006/019716, many compounds which have very broad and a variety of chemical structures are disclosed, and 1,2-dihydroquinoline structure is disclosed as one of them. However, 1,2-dihydroquinoline derivatives having substituted phenylamino lower alkyl group and ester-introduced phenyl group as substituents have not been specifically disclosed at all.

DISCLOSURE OF THE INVENTION

Problems to be Solved

It is a very interesting subject to study the synthesis of novel 1,2-dihydroquinoline derivatives having substituted phenylamino lower alkyl group and ester-introduced phenyl group as substituents and a salt thereof, and to find a pharmacological action of the derivatives and a salt thereof.

Means of Solving Problems

The present inventors conducted studies of the synthesis of novel 1,2-dihydroquinoline derivatives having substituted phenylamino lower alkyl group and ester-introduced phenyl group as substituents and a salt thereof having a novel chemical structure, and succeeded in producing a large number of novel compounds.

These novel compounds have chemical structural features 1) to 3) shown in below.

1) Having an ester structure (X is —C(O)—, —C(O)NR$^8$—, —S(O)— or —S(O)$_2$—) in A part of the general formula (1).
2) Having a hydroxy group or a lower alkoxy group in B part of the general formula (1).
3) Having a substituted phenylamino lower alkyl group (Y is a lower alkylene group) in C part of the general formula (1).

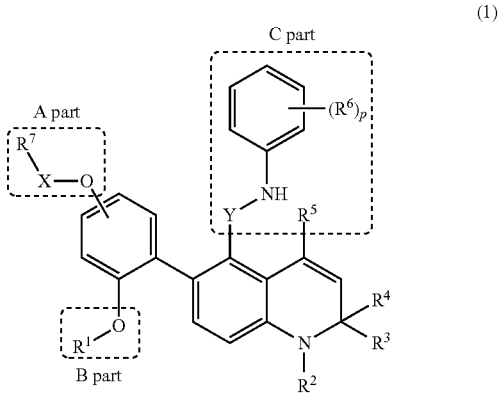

Further, as a result of the study about the pharmacological actions of the novel compound, the present inventors found that the novel compound have a glucocorticoid receptor binding activity and are useful as pharmaceuticals, and thus the present invention has been completed.

That is, the present invention relates to compounds represented by the following general formula (1) or a salt thereof (hereinafter referred to as "the present compound") and a pharmaceutical composition containing the same. Further, a preferred invention in its pharmaceutical use relates to glucocorticoid receptor modulators, and its target diseases are considered to be glucocorticoid receptor-related diseases, that is, metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like, and an invention relating to a preventive or a therapeutic agent for these diseases is particularly preferred.

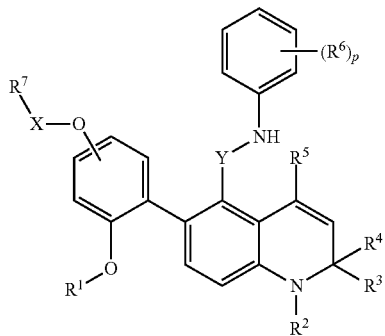

(1)

[$R^1$ represents a hydrogen atom or a lower alkyl group;
$R^2$ represents a hydrogen atom or a lower alkyl group;
$R^3$ and $R^4$ may be the same or different and represent a hydrogen atom or a lower alkyl group;
$R^5$ represents a hydrogen atom or a lower alkyl group;
$R^6$ represents a halogen atom, a lower alkyl group, a hydroxy group, a lower alkoxy group, a nitro group or a cyano group;
X represents —C(O)—, —C(O)$NR^8$—, —S(O)— or —S(O)$_2$—;
$R^7$ and/or $R^8$ may be the same or different and represent a hydrogen atom, a lower alkyl group which may have a substituent, a lower alkenyl group which may have a substituent, a lower alkynyl group which may have a substituent, a lower cycloalkyl group which may have a substituent, an aryl group which may have a substituent, a heterocyclic group which may have a substituent, a lower alkoxy group which may have a substituent, a lower alkenyloxy group which may have a substituent, a lower alkynyloxy group which may have a substituent, a lower cycloalkyloxy group which may have a substituent, an aryloxy group which may have a substituent or a heterocyclic oxy group which may have a substituent;
Y represents a lower alkylene group;
p represents 0, 1, 2 or 3, in the case where p is 2 or 3, each $R^6$ may be the same or different. Hereinafter the same shall apply.]

Advantage of the Invention

The present invention provides novel 1,2-dihydroquinoline derivatives having substituted phenylamino lower alkyl group and ester-introduced phenyl group as substituents or a salt, which are useful as pharmaceuticals. The present compound has an excellent glucocorticoid receptor binding activity and is useful as a glucocorticoid receptor modulator. In particular, the present compound is useful as a preventive or therapeutic agent for glucocorticoid receptor-related diseases, that is, metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like.

BEST MODE FOR CARRYING OUT THE INVENTION

Hereinafter, definitions of terms and phrases (atoms, groups and the like) used in this specification will be described in detail. In addition, when the definition of terms and phrases is applied to the definition of another terms and phrases, a desirable range and the particularly desirable range of each definition is also applied.

The "halogen atom" refers to a fluorine, chlorine, bromine or iodine atom.

The "lower alkyl group" refers to a straight chain or branched alkyl group having 1 to 8 carbon atoms, preferably 1 to 6, especially preferably 1 to 4. Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups and the like.

The "lower alkenyl group" refers to a straight chain or branched alkenyl group having 2 to 8 carbon atoms, preferably 2 to 6, especially preferably 2 to 4. Specific examples thereof include vinyl, propenyl, butenyl, pentenyl, hexenyl, heptenyl, octenyl, isopropenyl, 2-methyl-1-propenyl and 2-methyl-2-butenyl groups and the like.

The "lower alkynyl group" refers to a straight chain or branched alkynyl group having 2 to 8 carbon atoms, preferably 2 to 6, especially preferably 2 to 4. Specific examples thereof include ethynyl, propynyl, butynyl, pentynyl, hexynyl, heptynyl, octynyl, isobutynyl and isopentynyl groups and the like.

The "lower cycloalkyl group" refers to a cycloalkyl group having 3 to 10 carbon atoms, preferably 3 to 8, especially preferably 3 to 6. Specific examples thereof include cyclopropyl, cyclobutyl, cyclopentyl, cyclohexyl, cycloheptyl, cyclooctyl, cyclononanyl and cyclodecanyl groups.

The "aryl group" refers to a residue formed by removing one hydrogen atom from a monocyclic aromatic hydrocarbon group, or bicyclic or tricyclic condensed polycyclic aromatic hydrocarbon having 6 to 14 carbon atoms. Specific examples thereof include phenyl, naphthyl, anthryl and phenanthryl groups and the like.

The "heterocyclic ring" refers to a saturated or unsaturated monocyclic heterocyclic ring having one or a plurality of heteroatoms selected from a nitrogen atom, an oxygen atom and a sulfur atom in the ring (preferably, a saturated or unsaturated monocyclic 5 or 6 membered heterocyclic ring having one or two heteroatoms and 3 to 5 carbon atoms in the ring), or a bicyclic or tricyclic condensed polycyclic heterocyclic ring (preferably, a bicyclic or tricyclic condensed polycyclic heterocyclic ring having one or two heteroatoms and 7 to 13 carbon atoms in the ring).

Specific examples of the "saturated monocyclic heterocyclic ring" include pyrrolidine, pyrazolidine, imidazolidine, triazolidine, piperidine, hexahydropyridazine, hexahydropyrimidine, piperazine, homopiperidine and homopiperazine rings and the like having at least a nitrogen atom in the ring, tetrahydrofuran and tetrahydropyran rings and the like having at least an oxygen atom in the ring, tetrahydrothiophene and tetrahydrothiopyran rings and the like having a sulfur atom in the ring, oxazolidine, isoxazolidine and morpholine rings and the like having a nitrogen atom and an oxygen atom in the ring, and thiazolidine, isothiazolidine and thiomorpholine rings and the like having a nitrogen atom and a sulfur atom in the ring.

Further, such a saturated monocyclic heterocyclic ring can be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chromane, isochromane, dihydrobenzothiophene, dihydroisobenzothiophene, thiochromane, isothiochromane, dihydrobenzoxazole, dihydrobenzisoxazole, dihydrobenzoxazine, dihydrobenzothiazole, dihydrobenzisothiazole, dihydrobenzothiazine, xanthene, 4a-carbazole, or perimidine ring and the like.

Specific examples of the "unsaturated monocyclic heterocyclic ring" include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine rings and the like having at least a nitrogen atom in the ring, dihydrofuran, furan, dihydropyran and pyran rings and the like having at least an oxygen atom in the ring, dihydrothiophene, thiophene, dihydrothiopyran and thiopyran rings and the like having a sulfur atom in the ring, dihydrooxazole, oxazole, dihydroisoxazole, isoxazole, dihydrooxazine and oxazine rings and the like having a nitrogen atom and an oxygen atom in the ring, dihydrothiazole, thiazole, dihydroisothiazole, isothiazole, dihydrothiazine and thiazine rings and the like having a nitrogen atom and a sulfur atom in the ring.

Further, such an unsaturated monocyclic heterocyclic ring can be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, benzisothiazole, benzothiazine, phenoxanthin, carbazole, β-carboline, phenanthridine, acridine, phenanthroline, phenazine, phenothiazine or phenoxazine ring and the like.

Incidentally, among the above "heterocyclic ring", "monocyclic heterocyclic ring" is defined as the thing which put saturated monocyclic heterocyclic ring and unsaturated monocyclic heterocyclic ring together.

The "heterocyclic group" refers to a residue formed by removing a hydrogen atom from heterocyclic ring mentioned above.

The "lower alkoxy group" refers to a group formed by replacing the hydrogen atom of a hydroxy group with a lower alkyl group. Specific examples thereof include methoxy, ethoxy, n-propoxy, n-butoxy, n-pentoxy, n-hexyloxy, n-heptyloxy, n-octyloxy, isopropoxy, isobutoxy, sec-butoxy, tert-butoxy and isopentoxy groups and the like.

The "lower alkenyloxy group" refers to a group formed by replacing the hydrogen atom of a hydroxy group with a lower alkenyl group. Specific examples thereof include vinyloxy, propenyloxy, butenyloxy, pentenyloxy, hexenyloxy, heptenyloxy, octenyloxy, isopropenyloxy, 2-methyl-1-propenyloxy and 2-methyl-2-butenyloxy groups and the like.

The "lower alkynyloxy group" refers to a group formed by replacing the hydrogen atom of a hydroxy group with a lower alkynyl group. Specific examples thereof include ethynyloxy, propynyloxy, butynyloxy, pentynyloxy, hexynyloxy, heptynyloxy, octynyloxy, isobutynyloxy and isopentynyloxy groups and the like.

The "lower cycloalkyloxy group" refers to a group formed by replacing the hydrogen atom of a hydroxy group with a lower cycloalkyl group. Specific examples thereof include cyclopropyloxy, cyclobutyloxy, cyclopentyloxy, cyclohexyloxy, cycloheptyloxy, cyclooctyloxy, cyclononanyloxy and cyclodecanyloxy groups.

The "aryloxy group" refers to a group formed by replacing the hydrogen atom of a hydroxy group with an aryl group. Specific examples thereof include phenoxy, naphthoxy, anthryloxy and phenanthryloxy groups and the like.

The "heterocyclic oxy group" refers to a group formed by replacing the hydrogen atom of a hydroxy group with a heterocyclic group.

The "lower alkylthio group" refers to a group formed by replacing the hydrogen atom of a mercapto group with a lower alkyl group. Specific examples thereof include methylthio, ethylthio, n-propylthio, n-butylthio, n-pentylthio, n-hexylthio, n-heptylthio, n-octylthio, isopropylthio, isobutylthio, sec-butylthio, tert-butylthio and isopentylthio groups and the like.

The "lower alkenylthio group" refers to a group formed by replacing the hydrogen atom of a mercapto group with a lower alkenyl group. Specific examples thereof include vinylthio, propenylthio, butenylthio, pentenylthio, hexenylthio, heptenylthio, octenylthio, isopropenylthio, 2-methyl-1-propenylthio and 2-methyl-2-butenylthio groups and the like.

The "lower alkynylthio group" refers to a group formed by replacing the hydrogen atom of a mercapto group with a lower alkynyl group. Specific examples thereof include ethynylthio, propynylthio, butynylthio, pentynylthio, hexynylthio, heptynylthio, octynylthio, isobutynylthio and isopentynylthio groups and the like.

The "lower cycloalkylthio group" refers to a group formed by replacing the hydrogen atom of a mercapto group with a lower cycloalkyl group. Specific examples thereof include cyclopropylthio, cyclobutylthio, cyclopentylthio, cyclohexylthio, cycloheptylthio and cyclooctylthio groups.

The "arylthio group" refers to a group formed by replacing the hydrogen atom of a mercapto group with an aryl group. Specific examples thereof include phenylthio, naphthylthio, anthrylthio and phenanthrylthio groups and the like.

The "heterocyclic thio group" refers to a group formed by replacing the hydrogen atom of a mercapto group with a heterocyclic group.

The "lower alkylcarbonyl group" refers to a group formed by replacing the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, n-heptylcarbonyl, n-octylcarbonyl, isopropylcarbonyl, isobutylcarbonyl, sec-butylcarbonyl, tert-butylcarbonyl and isopentylcarbonyl groups and the like.

The "arylcarbonyl group" refers to a group formed by replacing the hydrogen atom of a formyl group with an aryl group. Specific examples thereof include phenylcarbonyl, naphthylcarbonyl, anthrylcarbonyl and phenanthrylcarbonyl groups and the like.

The "lower alkoxycarbonyl group" refers to a group formed by replacing the hydrogen atom of a formyl group with a lower alkoxy group. Specific examples thereof include methoxycarbonyl, ethoxycarbonyl, n-propoxycarbonyl, n-butoxycarbonyl, n-pentoxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl and isopentoxycarbonyl groups and the like.

The "aryloxycarbonyl group" refers to a group formed by replacing the hydrogen atom of a formyl group with an aryloxy group. Specific examples thereof include phenoxycarbonyl, naphthoxycarbonyl, anthryloxycarbonyl and phenanthryloxycarbonyl groups and the like.

The "lower alkylcarbonyloxy group" refers to a group formed by replacing the hydrogen atom of a hydroxy group with a lower alkylcarbonyl group. Specific examples thereof include methylcarbonyloxy, ethylcarbonyloxy, n-propylcarbonyloxy,
n-butylcarbonyloxy, n-pentylcarbonyloxy,
n-hexylcarbonyloxy, n-heptylcarbonyloxy,
n-octylcarbonyloxy, isopropylcarbonyloxy, isobutylcarbonyloxy, sec-butylcarbonyloxy, tert-butylcarbonyloxy and isopentylcarbonyloxy groups and the like.

The "arylcarbonyloxy group" refers to a group formed by replacing the hydrogen atom of a hydroxy group with an arylcarbonyl group. Specific examples thereof include phenylcarbonyloxy, naphthylcarbonyloxy, anthrylcarbonyloxy and phenanthrylcarbonyloxy groups and the like.

The "lower alkylene group" refers to a straight chain or branched alkylene group having 1 to 8 carbon atoms, preferably 1 to 6, especially preferably 1 to 4. Specific examples thereof include methylene, ethylene, trimethylene, tetramethylene, pentamethylene, hexamethylene, heptamethylene, octamethylene, methylmethylene and ethylmethylene groups and the like.

The "halogenated lower alkyl group" refers to a group formed by replacing the hydrogen atom of a lower alkyl group with one or a plurality of halogen atoms. Specific examples thereof include difluoromethyl, trifluoromethyl, trifluoroethyl, trifluoropropyl, dichloromethyl, trichloromethyl, trichloroethyl, trichloropropyl and the like.

The "halogenated lower alkoxy group" refers to a group formed by replacing the hydrogen atom of a lower alkoxy group with one or a plurality of halogen atoms. Specific examples thereof include difluoromethoxy, trifluoromethoxy, trifluoroethoxy, trifluoropropoxy, dichloromethoxy, trichloromethoxy, trichloroethoxy, trichloropropoxy and the like.

The "lower alkyl group which may have a substituent", "lower alkenyl group which may have a substituent", "lower alkynyl group which may have a substituent", "lower alkoxy group which may have a substituent", "lower alkenyloxy group which may have a substituent" and/or "lower alkynyloxy group which may have a substituent" refer to a "lower alkyl group", a "lower alkenyl group", a "lower alkynyl group", a "lower alkoxy group", a "lower alkenyloxy group" and/or a "lower alkynyloxy group" which may have one or a plurality of substituents selected from the following $\alpha^1$ group, preferred one or a plurality of substituents selected from the following $\alpha^2$, respectively.

[$\alpha^1$ Group]

A halogen atom, a lower cycloalkyl group, an aryl group, a heterocyclic group, a hydroxy group, a lower alkoxy group, a halogenated lower alkoxy group, a lower alkenyloxy group, a lower alkynyloxy group, a lower cycloalkyloxy group, an aryloxy group, a heterocyclic oxy group, a mercapto group, a lower alkylthio group, a lower alkenylthio group, a lower alkynylthio group, a lower cycloalkylthio group, an arylthio group, a heterocyclic thio group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, —NR$^a$R$^b$, a nitro group and a cyano group.

[$\alpha^2$ Group]

A halogen atom, a lower cycloalkyl group, an aryl group, a heterocyclic group, a hydroxy group, a lower alkoxy group, a lower alkenyloxy group, a lower alkynyloxy group, a lower cycloalkyloxy group, an aryloxy group, a heterocyclic oxy group and —NR$^a$R$^b$.

The "lower cycloalkyl group which may have a substituent", "aryl group which may have a substituent", "heterocyclic group which may have a substituent", "lower cycloalkyloxy group which may have a substituent", "aryloxy group which may have a substituent" and/or "heterocyclic oxy group which may have a substituent" refer to a "lower cycloalkyl group", an "aryl group", a "heterocyclic group", a "lower cycloalkyloxy group", an "aryloxy group" and/or a "heterocyclic oxy group" which may have one or a plurality of substituents selected from the following β group, respectively.

[β Group]

A halogen atom, a lower alkyl group, a halogenated lower alkyl group, a lower alkenyl group, a lower alkynyl group, a lower cycloalkyl group, an aryl group, a heterocyclic group, a hydroxy group, a lower alkoxy group, a halogenated lower alkoxy group, a lower alkenyloxy group, a lower alkynyloxy group, a lower cycloalkyloxy group, an aryloxy group, a heterocyclic oxy group, a mercapto group, a lower alkylthio group, a lower alkenylthio group, a lower alkynylthio group, a lower cycloalkylthio group, an arylthio group, a heterocyclic thio group, a formyl group, a lower alkylcarbonyl group, an arylcarbonyl group, a carboxy group, a lower alkoxycarbonyl group, an aryloxycarbonyl group, a lower alkylcarbonyloxy group, an arylcarbonyloxy group, —NR$^a$R$^b$, a nitro group and a cyano group.

R$^a$ and R$^b$ in the above "—NR$^a$R$^b$" may be the same or different and represent a substituent selected from the following $\gamma^1$ group, preferably the following $\gamma^2$ group

[$\gamma^1$ Group]

A hydrogen atom, a lower alkyl group, a lower alkenyl group, a lower alkynyl group, a lower cycloalkyl group, an aryl group, a heterocyclic group, a lower alkoxycarbonyl group and an aryloxycarbonyl group.

[$\gamma^2$ Group]

A hydrogen atom, a lower alkyl group, an aryl group, a heterocyclic group, a lower alkoxycarbonyl group and an aryloxycarbonyl group.

The term "a plurality of groups" as used in this invention means that each group may be the same or different and stands for 2 or more but not more than the number of groups which can be introduced into substitutable position(s), and the number is preferably 2 or 3, and 2 is particularly preferable.

Further, in this invention, a hydrogen atom and a halogen atom are also included in the concept of the "group".

The "glucocorticoid receptor modulator" as used herein refers to a modulator that exhibits a pharmaceutical action by binding to glucocorticoid receptor. Examples thereof include glucocorticoid receptor agonists, glucocorticoid receptor antagonists and the like.

The "salt" of the present compound is not particularly limited as long as it is a pharmaceutically acceptable salt. Examples thereof include salts with an inorganic acid such as hydrochloric acid, hydrobromic acid, hydroiodic acid, nitric acid, sulfuric acid or phosphoric acid of the like; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid, sulfosalicylic acid or the like; quaternary ammonium salts with methyl bromide, methyl iodide or the like; salts with a halogen ion such as a bromine ion, a chlorine ion, an iodine ion or the like; salts with an alkali metal such as lithium, sodium, potassium or the like; salts with an alkaline earth metal such as calcium, magnesium or the like; salts with a metal such as iron, zinc or the like; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-bis(phenylmethyl)-1,2-ethanediamine or the like.

In the case where there are geometrical isomers and/or optical isomers in the present compound, these isomers are also included in the scope of the present invention.

In the case where there are proton tautomers in the present compound, these tautomers (keto-form, enol-form) are also included in the scope of the present invention.

In the case where there are hydrate and/or solvate in the present compound, these hydrate and/or solvate are also included in the scope of the present invention.

In the case where there are polymorphism and polymorphism group (polymorphism system) in the present compound, these polymorphism and polymorphism group (polymorphism system) are also included in the scope of the present invention. "Polymorphism group (polymorphism system)" herein means each crystal form in each step where the crystal form changes depending on condition s and states (the states also include a state of drug formulation) of manufacture, crystallization and preservation and the like, and the entire process.

(a) Preferred examples of the present compound include compounds in which the respective groups are groups as defined below and salts thereof in the compounds represented by the general formula (1) and salts thereof.

(a1) $R^1$ represents a hydrogen atom or a lower alkyl group; and/or (a2) $R^2$ represents a hydrogen atom or a lower alkyl group; and/or (a3) $R^3$ and $R^4$ may be the same or different and represent a hydrogen atom or a lower alkyl group; and/or (a4) $R^5$ represents a hydrogen atom or a lower alkyl group; and/or (a5) $R^6$ represents a halogen atom, a lower alkyl group, a hydroxy group, a lower alkoxy group, a nitro group or a cyano group; and/or (a6) X represents —CO—, —C(O)NR$^8$—, —S(O)— or —S(O)$_2$—; and/or (a7) $R^7$ and/or $R^8$ may be the same or different and represent a hydrogen atom, a lower alkyl group, a lower alkenyl group, a lower alkynyl group, a lower cycloalkyl group, an aryl group, a heterocyclic group, a lower alkoxy group, a lower alkenyloxy group, a lower alkynyloxy group, a lower cycloalkyloxy group, an aryloxy group or a heterocyclic oxy group;

in the case where $R^7$ and/or $R^8$ is a lower alkyl group, a lower alkenyl group, a lower alkynyl group, a lower alkoxy group, a lower alkenyloxy group or a lower alkynyloxy group, the lower alkyl group, lower alkenyl group, lower alkynyl group, lower alkoxy group, lower alkenyloxy group or lower alkynyloxy group may have one or a plurality of groups selected from a halogen atom, a lower cycloalkyl group, an aryl group, a heterocyclic group, a hydroxy group, a lower alkoxy group, a lower alkenyloxy group, a lower alkynyloxy group, a lower cycloalkyloxy group, an aryloxy group, a heterocyclic oxy group and —NR$^a$R$^b$ as substituent(s);

in the case where $R^7$ and/or $R^8$ is a lower cycloalkyl group, an aryl group, a heterocyclic group, a lower cycloalkyloxy group, an aryloxy group or a heterocyclic oxy group, the lower cycloalkyl group, aryl group, heterocyclic group, lower cycloalkyloxy group, aryloxy group or heterocyclic oxy group may have one or a plurality of groups selected from a halogen atom, a lower alkyl group, a halogenated lower alkyl group, an aryl group, a lower alkenyl group, a lower alkynyl group, a lower cycloalkyl group, an aryl group, a heterocyclic group, a hydroxy group, a lower alkoxy group, a halogenated lower alkoxy group, a lower alkenyloxy group, a lower alkynyloxy group, a lower cycloalkyloxy group, an aryloxy group, a heterocyclic oxy group, a mercapto group, a lower alkylthio group, a lower alkenylthio group, a lower alkynylthio group, a lower cycloalkylthio group, an arylthio group, a heterocyclic thio group, a lower alkylcarbonyl group, an arylcarbonyl group, a lower alkoxycarbonyl group, an aryloxycarbonyl group, a lower alkylcarbonyloxy group, an arylcarbonyloxy group, —NR$^a$R$^b$ a nitro group and a cyano group as substituent(s);

$R^a$ and $R^b$ may be the same or different and represent a hydrogen atom, a lower alkyl group, a lower alkenyl group, a lower alkynyl group, a lower cycloalkyl group, an aryl group, a heterocyclic group, a lower alkoxycarbonyl group or an aryloxycarbonyl group; and/or (a8) Y represents a lower alkylene group; and/or (a9) p represents 0, 1, 2 or 3, in the case where p is 2 or 3, each $R^6$ may be the same or different.

That is, in the compounds represented by the general formula (1) and salts thereof, preferred examples include compounds that comprise one or a combination of two or more selected from the above (a1), (a2), (a3), (a4), (a5), (a6), (a7), (a8) and (a9), and salts thereof.

(b) More preferred examples of the present compound include compounds in which the respective groups are groups as defined below and salts thereof in the compounds represented by the general formula (1) and salts thereof.

(b1) $R^1$ represents a hydrogen atom or a lower alkyl group; and/or (b2) $R^2$ represents a hydrogen atom or a lower alkyl group; and/or (b3) $R^3$ and $R^4$ may be the same or different and represent a hydrogen atom or a lower alkyl group; and/or (b4) $R^5$ represents a hydrogen atom or a lower alkyl group; and/or (b5) $R^6$ represents a halogen atom, a lower alkyl group, a hydroxy group or a lower alkoxy group; and/or (b6) X represents —CO—, —C(O)NR$^8$—, —S(O)— or —S(O)$_2$—; and/or (b7) $R^7$ and/or $R^8$ may be the same or different and represent a hydrogen atom, a lower alkyl group, a lower cycloalkyl group, an aryl group, a heterocyclic group, a lower alkoxy group, a lower cycloalkyloxy group, an aryloxy group or a heterocyclic oxy group;

in the case where $R^7$ and/or $R^8$ is a lower alkyl group, the lower alkyl group may have one or a plurality of groups selected from a halogen atom and —NR$^a$R$^b$ as substituent(s);

in the case where $R^7$ and/or $R^8$ is a lower cycloalkyl group, an aryl group, a heterocyclic group, a lower cycloalkyloxy group, an aryloxy group or a heterocyclic oxy group, the lower cycloalkyl group, aryl group, heterocyclic group, lower cycloalkyloxy group, aryloxy group or heterocyclic oxy group may have one or a plurality of groups selected from a halogen atom, a lower alkyl group, a hydroxy group, a lower alkoxy group, a mercapto group, a lower alkylthio group, a lower alkylcarbonyl group, a lower alkoxycarbonyl group, a lower alkylcarbonyloxy group and a nitro group as substituent(s);

$R^a$ and $R^b$ may be the same or different and represent a hydrogen atom or a lower alkyl group; and/or (b8) Y represents a lower alkylene group; and/or (b9) p represents 0, 1, 2 or 3, in the case where p is 2 or 3, each $R^6$ may be the same or different.

That is, in the compounds represented by the general formula (1) and salts thereof, more preferred examples include compounds that comprise one or a combination of two or more selected from the above (b1), (b2), (b3), (b4), (b5), (b6), (b7), (b8) and (b9), and salts thereof.

(c) Further more preferred examples of the present compound include compounds in which the respective groups are groups as defined below and salts thereof in the compounds represented by the general formula (1) and salts thereof.

(c1) $R^1$ represents a lower alkyl group; and/or
(c2) $R^2$ represents a hydrogen atom; and/or
(c3) $R^3$ and $R^4$ represent a lower alkyl group; and/or
(c4) $R^5$ represents a lower alkyl group; and/or
(c5) $R^6$ represents a halogen atom, a lower alkyl group or a lower alkoxy group; and/or
(c6) X represents —CO—, —C(O)$NR^8$— or —S(O)$_2$—; and/or
(c7) $R^7$ represents a lower alkyl group, a lower cycloalkyl group, an aryl group, a heterocyclic group, a lower alkoxy group or an aryloxy group;

in the case where $R^7$ is a lower alkyl group, the lower alkyl group may have one or a plurality of groups selected from a halogen atom and —$NR^aR^b$ as substituent(s);

in the case where $R^7$ is an aryl group, a heterocyclic group or an aryloxy group, the aryl group, heterocyclic group or aryloxy group may have one or a plurality of groups selected from a halogen atom, a lower alkyl group, a lower alkoxy group, a lower alkylthio group, a lower alkylcarbonyl group, a lower alkoxycarbonyl group, a lower alkylcarbonyloxy group and a nitro group as substituent(s);

$R^a$ and $R^b$ may be the same or different and represent a hydrogen atom or a lower alkyl group; and/or (c8) $R^8$ represents a hydrogen atom or a lower alkyl group; and/or (c9) Y represents a lower alkylene group; and/or (c10) p represents 0, 1 or 2, in the case where p is 2, each $R^6$ may be the same or different.

That is, in the compounds represented by the general formula (1) and salts thereof, further more preferred examples include compounds that comprise one or a combination of two or more selected from the above (c1), (c2), (c3), (c4), (c5), (c6), (c7), (c8), (c9) and (c10), and salts thereof.

(d) Further more preferred examples of the present compound include compounds in which the respective groups are groups as defined below and salts thereof in the compounds represented by the general formula (1) and salts thereof.

(d1) $R^1$ represents a lower alkyl group; and/or
(d2) $R^2$ represents a hydrogen atom; and/or
(d3) $R^3$ and $R^4$ represent a lower alkyl group; and/or
(d4) $R^5$ represents a lower alkyl group; and/or
(d5) $R^6$ represents a halogen atom, a lower alkyl group or a lower alkoxy group; and/or
(d6) X represents —CO—, —C(O)$NR^8$— or —S(O)$_2$—; and/or
(d7) $R^7$ represents a lower alkyl group, a lower cycloalkyl group, an aryl group, a heterocyclic group, a lower alkoxy group or an aryloxy group;

in the case where $R^7$ is a lower alkyl group, the lower alkyl group may have one or a plurality of groups selected from a halogen atom and —$NR^aR^b$ as substituent(s);

in the case where $R^7$ is an aryl group, the aryl group may have one or a plurality of groups selected from a halogen atom, a lower alkyl group, a lower alkoxy group, a lower alkylthio group, a lower alkylcarbonyl group, a lower alkoxycarbonyl group, a lower alkylcarbonyloxy group and a nitro group as substituent(s);

in the case where $R^7$ is a heterocyclic group, the heterocyclic group may have one or a plurality of groups selected from a halogen atom, a lower alkyl group and a lower alkoxy group as substituent(s);

in the case where $R^7$ is an aryloxy group, the aryloxy group may have one or a plurality of halogen atoms as substituent(s);

$R^a$ and $R^b$ may be the same or different and represent a hydrogen atom or a lower alkyl group; and/or (d8) $R^8$ represents a hydrogen atom or a lower alkyl group; and/or (d9) Y represents a lower alkylene group; and/or (d10) p represents 0, 1 or 2, in the case where p is 2, each $R^6$ may be the same or different.

That is, in the compounds represented by the general formula (1) and salts thereof, further more preferred examples include compounds that comprise one or a combination of two or more selected from the above (d1), (d2), (d3), (d4), (d5), (d8), (d7), (d8), (d9) and (d10), and salts thereof.

(e) Specific examples of the present compound represented by the preferred substituent(s) include compounds in which $R^1$, $R^3$, $R^4$ and $R^5$ represents a methyl group, $R^2$ represents a hydrogen atom, Y is a methylene group in the general formula (1) and satisfy the above conditions (a), (b), (c) and/or (d), and salts thereof.

(f) Particularly preferred specific examples of the present compound include the following compounds and salts thereof.

6-[4-(Furan-2-ylcarbonyloxy)-2-methoxyphenyl]-5-(2-methoxyphenylaminomethyl)-2,2,4-trimethyl-1,2-dihydroquinoline, 6-[2-Methoxy-4-(2-methylpyridin-3-ylcarbonyloxy)phenyl]-5-(2-methoxyphenylaminomethyl)-2,2,4-trimethyl-1,2-dihydro quinoline, 6-(4-Benzoyloxy-2-methoxyphenyl)-5-(2-methoxyphenylaminomethyl)-2,2,4-trimethyl-1,2-dihydroquinoline, 6-[2-Methoxy-4-(2-methoxybenzoyloxy)phenyl]-5-(2-methoxyphenylaminomethyl)-2,2,4-trimethyl-1,2-dihydroquinoline, 6-[2-Methoxy-4-(2-methylbenzoyloxy)phenyl]-5-(2-methoxyphenylaminomethyl)-2,2,4-trimethyl-1,2-dihydroquinoline, 6-[4-(Furan-3-ylcarbonyloxy)-2-methoxyphenyl]-5-(2-methoxyphenylaminomethyl)-2,2,4-trimethyl-1,2-dihydroquinoline, 5-(2-Methoxyphenylaminomethyl)-6-[2-methoxy-4-(thiophen-3-ylcarbonyloxy)phenyl]-2,2,4-trimethyl-1,2-dihydroquinoline, 5-(2-Methoxyphenylaminomethyl)-6-[2-methoxy-4-(pyridin-3-ylcarbonyloxy)phenyl]-2,2,4-trimethyl-1,2-dihydroquinoline, 6-[4-(2-Chlorobenzoyloxy)-2-methoxyphenyl]-5-(5-fluoro-2-methylphenylaminomethyl)-2,2,4-trimethyl-1,2-dihydroquinoline, 6-[4-(2-Chlorobenzoyloxy)-2-methoxyphenyl]-5-(2-methoxyphenylaminomethyl)-2,2,4-trimethyl-1,2-dihydroquinoline, 6-[4-(2-Fluorobenzoyloxy)-2-methoxyphenyl]-5-(2-methoxyphenylaminomethyl)-2,2,4-trimethyl-1,2-dihydroquinoline, 5-(2-Methoxyphenylaminomethyl)-6-[2-methoxy-4-(pyridin-4-ylcarbonyloxy)phenyl]-2,2,4-trimethyl-1,2-dihydroquinoline, 6-(4-Isopropylcarbonyloxy-2-methoxyphenyl)-5-(2-methoxyphenylaminomethyl)-2,2,4-trimethyl-1,2-dihydroquinoline, 5-(2-Methoxyphenylaminomethyl)-6-[2-methoxy-4-(thiophen-2-ylcarbonyloxy)phenyl]-2,2,4-trimethyl-1,2-dihydroquinoline, 5-(5-Fluoro-2-methylphenylaminomethyl)-6-[2-methoxy-4-(pyridin-3-ylcarbonyloxy)phenyl]-2,2,4-trimethyl-1,2-dihydroquinoline, 5-(5-Fluoro-2-methylphenylaminomethyl)-6-[4-(furan-2-ylcarbonyloxy)-2-methoxyphenyl]-2,2,4-trimethyl-1,2-dihydroquinoline, 6-[2-Methoxy-4-(3-methoxycarbonylbenzoyloxy)phenyl]-5-(2-methoxyphenylaminomethyl)-2,2,4-trimethyl-1,2-dihydroquinoline, 6-[2-Methoxy-4-(4-methoxybenzoyloxy)phenyl]-5-(2-methoxyphenylaminomethyl)-2,2,4-trimethyl-1,2-dihydroquinoline, 6-[4-(4-Fluorobenzoyloxy)-2-methoxyphenyl]-5-(2-methoxyphenylaminomethyl)-2,2,4-trimethyl-1,2-dihydroquinoline, 6-[2-Methoxy-4-(2-methylthiobenzoyloxy)phenyl]-5-(2-methoxyphenylaminomethyl)-2,2,4-trimethyl-1,2-dihydroquinoline 6-[4-(3-Acetylbenzoyloxy)-2-methoxyphenyl]-5-(2-methoxyphenylaminomethyl)-2,2,4-trimethyl-1,2-dihydroquinoline, 6-[4-(3-Chlorothiophen-2-ylcarbonyloxy)-2-methoxyphenyl]-5-(2-methoxyphenylaminomethyl)-2,2,4-trimethyl-1,2-dihydroquinoline, 6-[2-Methoxy-4-(3-methylfuran-2-ylcarbonyloxy)phenyl]-5-(2-methoxyphenylaminomethyl)-2,2,4-trimethyl-1,2-dihydroquinoline, 5-(2-Methoxyphenylaminomethyl)-6-[2-methoxy-4-(thiazol-4-ylcarbonyloxy)phenyl]-2,2,4-trimethyl-1,2-dihydroquinoline, 6-[2-Methoxy-4-(6-methylpyridin-3-ylcarbonyloxy)phenyl]-5-(2-methoxyphenylaminomethyl)-2,2,4-trimethyl-1,2-dihydroquinoline, 6-[2-Methoxy-4-(2-methoxypyridin-3-ylcarbonyloxy)phenyl]-5-(2-methoxyphenylaminomethyl)-2,2,4-trimethyl-1,2-dihydroquinoline, 5-(5-Fluoro-2-methylphenylaminomethyl)-6-[4-(furan-3-ylcarbonyloxy)-2-methoxyphenyl]-2,2,4-trimethyl-1,2-dihydroquinoline, 5-(5-Fluoro-2-methylphenylaminomethyl)-6-[2-methoxy-4-(pyridin-4-ylcarbonyloxy)phenyl]-2,2,4-trimethyl-1,2-dihydroquinoline, 6-[4-(2-Fluorobenzoyloxy)-2-methoxyphenyl]-5-(5-fluoro-2-methylphenylaminomethyl)-2,2,4-trimethyl-1,2-dihydroquinoline, 5-(5-Fluoro-2-methylphenylaminomethyl)-6-[2-methoxy-4-(2-methylpyridin-3-ylcarbonyloxy)phenyl]-2,2,4-trimethyl-1,2-dihydroquinoline, 5-(5-Fluoro-2-methylphenylaminomethyl)-6-[4-(2-methylthiobenzoyloxy)-2-methoxyphenyl]-2,2,4-trimethyl-1,2-dihydroquinoline, 5-(5-Fluoro-2-methylphenylaminomethyl)-6-[2-methoxy-4-(2-methoxypyridin-3-ylcarbonyloxy)phenyl]-2,2,4-trimethyl-1,2-dihydroquinoline, 5-(5-Fluoro-2-methylphenylaminomethyl)-6-[2-methoxy-4-(3-methylfuran-2-ylcarbonyloxy)phenyl]-2,2,4-trimethyl-1,2-dihydroquinoline, 6-(4-Dimethylaminocarbonyloxy-2-methoxyphenyl)-5-(2-methoxyphenylaminomethyl)-2,2,4-trimethyl-1,2-dihydroquinoline 6-[2-Methoxy-4-(morpholin-4-ylcarbonyloxy)phenyl]-5-(2-methoxyphenylaminomethyl)-2,2,4-trimethyl-1,2-dihydroquinoline, 5-(5-Fluoro-2-methylphenylaminomethyl)-6-[2-methoxy-4-(morpholin-4-ylcarbonyloxy)phenyl]-2,2,4-trimethyl-1,2-dihydroquinoline, 5-(2-Methoxyphenylaminomethyl)-6-(2-methoxy-4-propylsulfonyloxyphenyl)-2,2,4-trimethyl-1,2-dihydroquinoline, 6-(4-Isopropylsulfonyloxy-2-methoxyphenyl)-5-(2-methoxyphenylaminomethyl)-2,2,4-trimethyl-1,2-dihydroquinoline, 6-(2-Methoxy-4-methylsulfonyloxyphenyl)-5-(2-methoxyphenylaminomethyl)-2,2,4-trimethyl-1,2-dihydroquinoline, 5-(5-Fluoro-2-methylphenylaminomethyl)-6-(2-methoxy-4-propylsulfonyloxyphenyl)-2,2,4-trimethyl-1,2-dihydroquinoline, 6-(4-Cyclopropylsulfonyloxy-2-methoxyphenyl)-5-(2-methoxyphenylaminomethyl)-2,2,4-trimethyl-1,2-dihydroquinoline, 6-(4-Cyclopentylsulfonyloxy-2-methoxyphenyl)-5-(2-methoxyphenylaminomethyl)-2,2,4-trimethyl-1,2-dihydroquinoline, 5-(5-Fluoro-2-methylphenylaminomethyl)-6-(2-methoxy-4-methylsulfonyloxyphenyl)-2,2,4-trimethyl-1,2-dihydroquinoline, 6-[4-[N-(2-Dimethylaminoethyl)-N-methylaminocarbonyloxy]-2-methoxyphenyl]-5-(2-methoxyphenylaminomethyl)-2,2,4-trimethyl-1,2-dihydroquinoline, 5-(2-Methoxyphenylaminomethyl)-6-[2-methoxy-4-(pyridin-3-ylaminocarbonyloxy)phenyl]-2,2,4-trimethyl-1,2-dihydroquinoline, and 6-[4-[N-(2-Dimethylaminoethyl)-N-methylaminocarbonyloxy]-2-methoxyphenyl]-5-(5-fluoro-2-methylphenylaminomethyl)-2,2,4-trimethyl-1,2-dihydroquinoline.

The present compound can be synthesized according to the following procedures. The individual concrete preparation procedures are explained in details in the section of "Production Examples" in Examples. These examples are intended to make the present invention more clearly understandable, and do not limit the scope of the present invention. The hal shown in the following synthetic routes represents a halogen atom. The fmoc represents a 9-fluorenylmethoxycarbonyl group.

The present compound (I)-(a) (the compound in which Y is a methylene group, $R^2$ is H, $R^3$, $R^4$ and $R^5$ are methyl groups, X is C(O) in the general formula (1)) can be synthesized according to the synthetic route 1. Namely, the compound (I)-(a) can be given by the reaction of the compound (II) with a corresponding halide (III) in an organic solvent such as methylene dichloride, N,N-dimethylformamide (hereinafter referred to as DMF) in the presence of a base such as triethylamine, diisopropylethylamine (hereinafter referred to as DIEA) at 0° C. to room temperature for 1 hour to 2 days.

And the compound (I)-(a) can be given by the reaction of the compound (II) with a corresponding carboxylic acid (IV) in an organic solvent such as methylene dichloride, DMF in the presence of a base such as triethylamine, DIEA and a condensation agent such as N,N'-dicyclohexylcarbodiimide, O-(7-azabenzotriazol-1-yl)-N,N,N,N-tetramethyluronium hexafluorophosphate at 0° C. to room temperature for 30 minutes to 3 days.

Synthetic Route 1

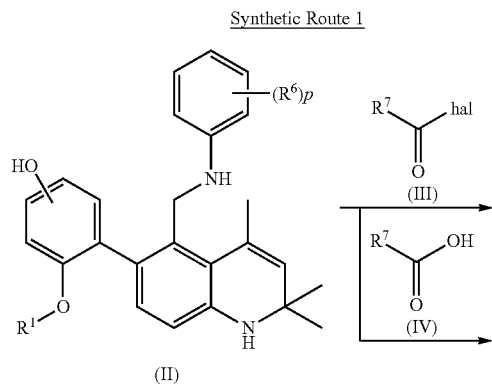

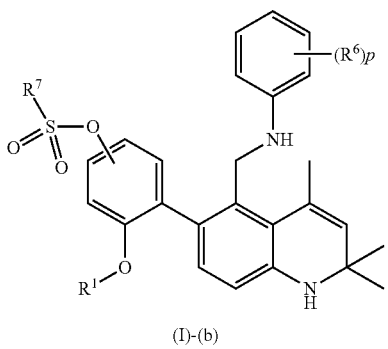

The present compound (I)-(b) (the compound in which Y is a methylene group, $R^2$ is H, $R^3$, $R^4$ and $R^5$ are methyl groups, X is $S(O)_2$ in the general formula (1)) can be synthesized according to the synthetic route 2. Namely, the compound (I)-(b) can be given by the reaction of the compound (II) with a corresponding halide (V) in an organic solvent such as methylene dichloride, DMF in the presence of a base such as triethylamine, DIEA at 0° C. to room temperature for 1 hour to 2 days.

Synthetic Route 2

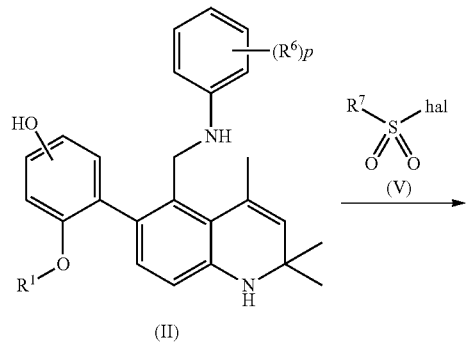

The present compound (I)-(c) (the compound in which Y is a methylene group, $R^2$ is H, $R^3$, $R^4$ and $R^5$ are methyl groups, X is $C(O)NR^8$ and $R^8$ is a hydrogen atom in the general formula (I)) can be synthesized according to the synthetic route 3. Namely, the compound (I)-(c) can be given by the reaction of the compound (II) with a corresponding isocyanate (VI) in an organic solvent such as methylene dichloride, DMF in the presence of a base such as triethylamine, DIEA at 0° C. to room temperature for 30 minutes to 1 day.

Synthetic Route 3

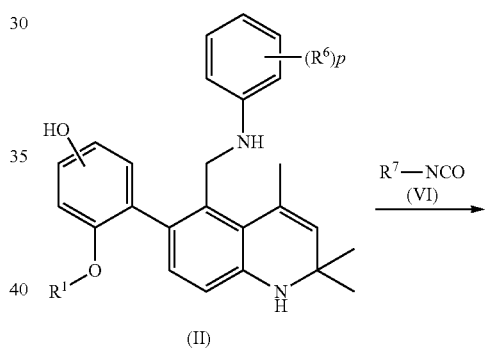

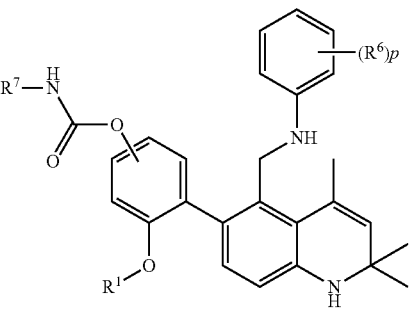

The present compound (I)-(d) (the compound in which Y is a methylene group, $R^2$ is H, $R^3$, $R^4$ and $R^5$ are methyl groups, X is $C(O)NR^8$ in the general formula (1)) can be synthesized according to the synthetic route 4. Namely, the compound (I)-(d) can be given by the reaction of the compound (II) with 1,1'-carbonyldiimidazole in an organic solvent such as methylene dichloride, tetrahydrofuran (hereinafter referred to as THF) at room temperature to 50° C. for 30 minutes to 12 hours followed by the reaction with a corresponding amine (VII) at room temperature to 50° C. for 30 minutes to 5 hours.

Synthetic Route 4

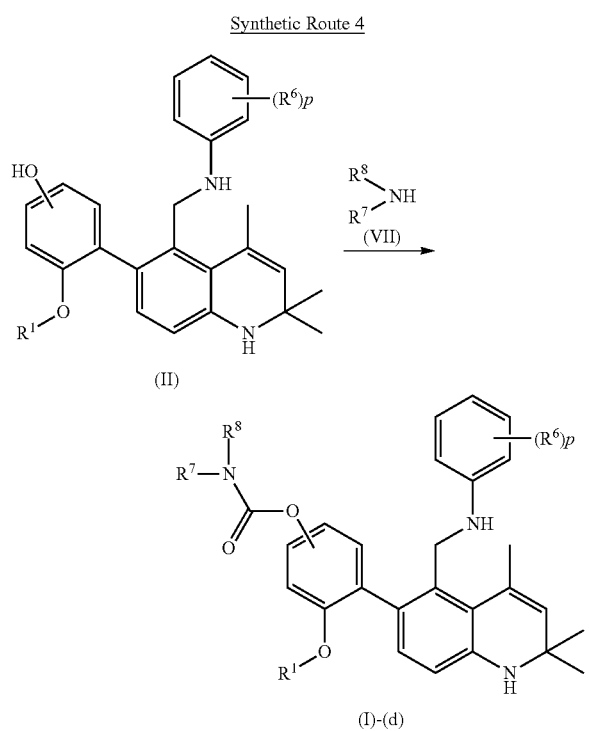

The present compounds (I)-(a), (I)-(b), (I)-(c), and (I)-(d) can be also synthesized according to the synthetic route 5. Namely, the compound (I)-(a), (I)-(b), (I)-(c), and (I)-(d) can be given by the reaction of the compound (VIII) with a halide (III), a carboxylic acid (IV), a halide (V), an isocyanate (VI) or an amine (VII) according to synthetic route 1, 2, 3 or 4 followed by the treatment with a base such as piperidine in an organic solvent such as DMF, methylene dichloride at 0° C. to 50° C. for 5 minutes to 24 hours.

Synthetic Route 5

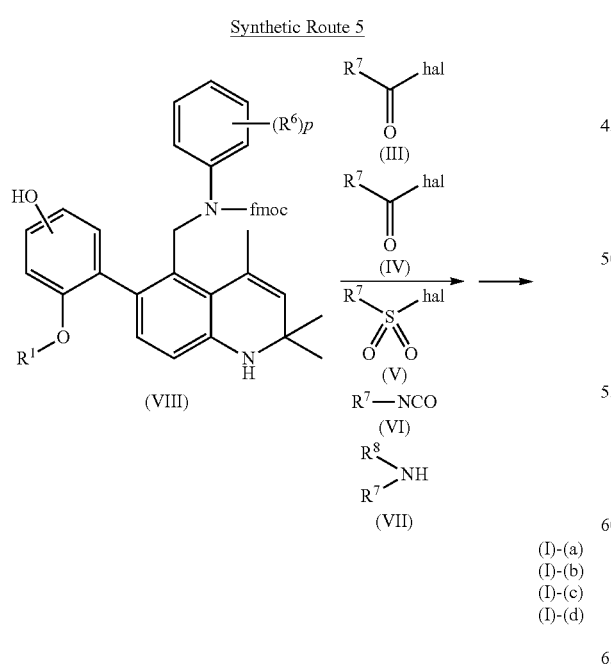

The compound (II) and (VIII) can be synthesized according to the synthetic route 6. Namely, the compound (X) can be given by the reaction of the compound (IX) with methanesulfonyl chloride in an organic solvent such as methylene dichloride, DMF in the presence of a base such as triethylamine, DIEA at 0° C. to room temperature for 30 minutes to 3 days. The compound (XII) can be given by the reaction of the compound (X) with a corresponding amine (XI) in an organic solvent such as DMF, methylene dichloride in the presence of a base such as potassium carbonate, DIEA, sodium hydride at 50° C. to 100° C. for 1 hour to days. The compound (II) can be given by the treatment of the compound (XII) in an organic solvent such as methylene dichloride, 1,4-dioxane in the presence of an acid such as hydrogen chloride, trifluoroacetic acid. The compound (VIII) can be given by the reaction of the compound (II) with 9-fluorenylmethoxycarbonyl chloride in a solvent such as 1,4-dioxane, water in the presence of a base such as sodium hydrogen carbonate at 0° C. to 50° C. for 1 hour to 24 hours.

Synthetic Route 6

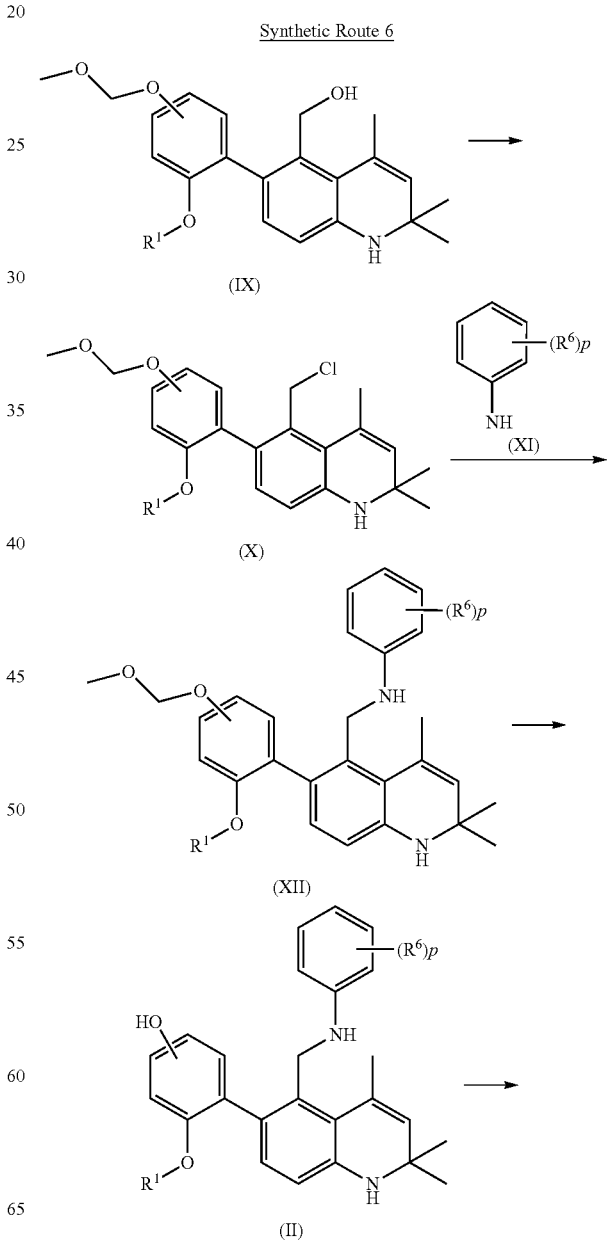

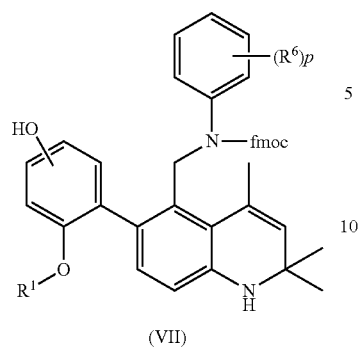

(VII)

The compound (IX) can be synthesized according to the synthetic route 7. Namely, the compound (XV) can be given by the reaction of a boronic acid (XIII) with a halide or triflate (XIV) in a solvent such as DMF, ethanol, toluene, water in the presence of a base such as cesium carbonate, sodium carbonate, potassium phosphate and a catalyst such as bis(triphenylphosphine)palladium (II) dichloride, tetrakis(triphenylphosphine)palladium (0) at 50° C. to 120° C. for 12 hours to 2 days. The compound (XVI) can be given by the treatment of the obtained compound (XV) in a solvent such as methylene dichloride, THF in the presence of an acid such as boron tribromide, hydrogen chloride at −78° C. to room temperature for 1 hour to 1 day. The compound (XVII) can be given by the treatment of the obtained compound (XVI) under hydrogen atmosphere in an organic solvent such as methanol, ethanol, 1,4-dioxane, THF in the presence of a catalyst such as palladium carbon, platinum dioxide at room temperature for 2 hours to 2 days. The compound (XVIII) can be given by the treatment of the obtained compound (XVII) in acetone in the presence of iodine at 80° C. to 130° C. for 24 hours to 5 days. The compound (XIX) can be given by the reaction of the obtained compound (XVIII) with chlorodimethylether in an organic solvent such as methylene dichloride, DMF in the presence of a base such as potassium carbonate, triethylamine, DIEA. The compound (XX) can be given by the treatment of the obtained compound (XIX) in an organic solvent such as diethyl ether, THF in the presence of a reducing agent such as lithium aluminium hydride at 0° C. to 50° C. for 1 hour to 1 day. The compound (VIII) can be given by the reaction of the compound (XX) with a corresponding halide (XXI) in an organic solvent such as DMF, ethanol in the presence of a base such as potassium carbonate, DIEA at room temperature to 100° C. for 1 hour to 24 hours.

Synthetic Route 7

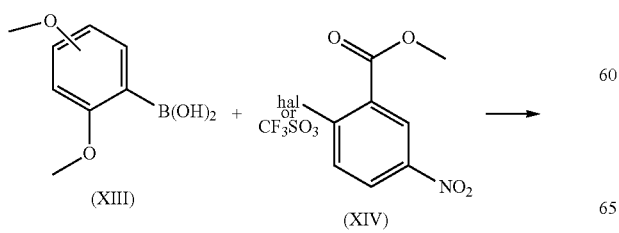

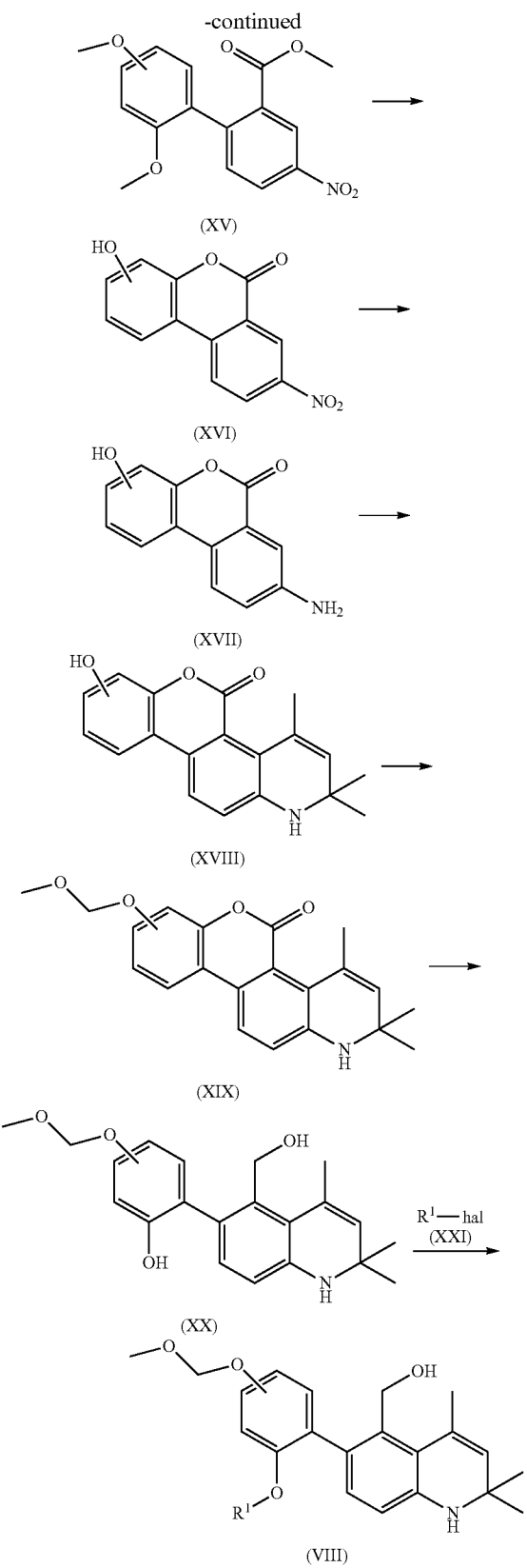

A detailed explanation of this matter will be described in the section of "Pharmacological Test" in Examples described below. In order to find the usefulness of the present compound as a pharmaceutical, a glucocorticoid receptor competitor assay was carried out by a fluorescence polarization method by using a glucocorticoid receptor competitor assay kit (manufactured by Invitrogen, cat No. P2816) to study the glucocorticoid receptor binding activity of the present compound. As a result, the present compound showed an excellent glucocorticoid receptor binding activity to the glucocorticoid receptor.

Incidentally, the glucocorticoid receptor is associated with the occurrence of various diseases as described above, therefore, the present compound having an excellent binding activity to the glucocorticoid receptor is useful as a glucocorticoid receptor modulator.

The present compound can be administered either orally or parenterally. Examples of the dosage form include a tablet, a capsule, a granule, a powder, an injection, an eye drop, a suppository, percutaneous absorption preparation, an ointment, an aerosol (including an inhalant) and the like and such a preparation can be prepared using a commonly used technique.

For example, an oral preparation such as a tablet, a capsule, a granule or a powder can be prepared by optionally adding a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor, or the like.

A parenteral preparation such as an injection or an eye drop can be prepared by optionally adding a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polysorbate 80, polyoxy 40 stearate or polyoxyethylene hydrogenated castor oil 60; stabilizer such as sodium citrate or sodium edetate; a preservative such as benzalkonium chloride, paraben, benzothonium chloride, p-hydroxybenzoate ester, sodium benzoate or chlorobutanol; a pH adjusting agent such as hydrochloric acid, citric acid, phosphoric acid, glacial acetic acid, sodium hydroxide, sodium carbonate or sodium hydrogen carbonate; a soothing agent such as benzyl alcohol, or the like.

This invention also provides a preventive or therapeutic method for glucocorticoid receptor related diseases, for examples, metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like.

The dose of the present compound can be appropriately selected depending on the kinds of the diseases, symptoms, age, dosage form or the like. For example, in the case of an oral preparation, it can be administered in an amount of generally 0.01 to 1000 mg, preferably 1 to 100 mg per day in a single dose or several divided doses. Further, in the case of an eye drop, a preparation containing the present compound at a concentration of generally 0.0001% to 10% (w/v), preferably 0.01% to 5% (w/v) can be administered in a single dose or several divided doses.

Hereinafter, Production Examples of the present compound, Preparation Examples and results of Pharmacological Test will be described. However, these examples are described for the purpose of understanding the present invention better and are not meant to limit the scope of the present invention.

PRODUCTION EXAMPLES

Reference Example 1

5-Hydroxymethyl-6-(2-methoxy-4-methoxymethoxyphenyl)-2,2,4-trimethyl-1,2-dihydroquioline (Reference Compound No. 1)

Methyl 2-(2,4-dimethoxyphenyl)-5-nitrobenzoate (Reference Compound No. 1-(1))

A mixture of 2,4-dimethoxyphenylboronic acid (25.0 g, 137 mmol), methyl 2-bromo-5-nitrobenzoate (35.7 g, 137 mmol), cesium carbonate (89.4 g, 274 mmol) and bis(triphenylphosphine)palladium (II) dichloride (4.81 g, 6.85 mmol) was suspended in N,N-dimethylformamide (450 mL), and then the suspension was stirred under argon atmosphere at 80° C. overnight. After cooling down, ethyl acetate (200 mL), diethylether (400 mL) and water (1000 mL) were added thereto and the mixture was separated into a water phase and an organic layer. The water layer was extracted with a mixed solvent of ethyl acetate (150 mL)-diethylether (150 mL) (twice). The combined organic layer was washed with water (500 mL, 3 times) and saturated brine (500 mL) successively, dried over anhydrous magnesium sulfate, and then the solvent was removed under reduced pressure to give the titled reference compound as a brown oil. (Quantitative)

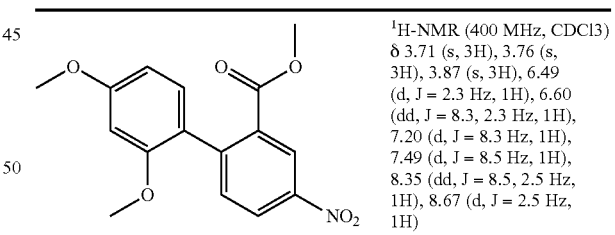

$^1$H-NMR (400 MHz, CDCl3) δ 3.71 (s, 3H), 3.76 (s, 3H), 3.87 (s, 3H), 6.49 (d, J = 2.3 Hz, 1H), 6.60 (dd, J = 8.3, 2.3 Hz, 1H), 7.20 (d, J = 8.3 Hz, 1H), 7.49 (d, J = 8.5 Hz, 1H), 8.35 (dd, J = 8.5, 2.5 Hz, 1H), 8.67 (d, J = 2.5 Hz, 1H)

3-Hydroxy-8-nitrobenzo[c]chromen-6-one (Reference Compound No. 1-(2))

A solution of methyl 2-(2,4-dimethoxyphenyl)-5-nitrobenzoate (Reference Compound No. 1-(1), 43.5 g, 137 mmol) in anhydrous methylene dichloride (250 mL) was cooled to −78° C., boron tribromide (96.2 g, 384 mmol) was added thereto, and then the mixture was stirred at room temperature for 1 hour. The mixture was cooled to −50° C. and methanol (300 mL) was added thereto. The resulting precipitates were filtered off with methanol to give the titled reference compound (18.0 g) as a yellow solid. (Yield 51%)

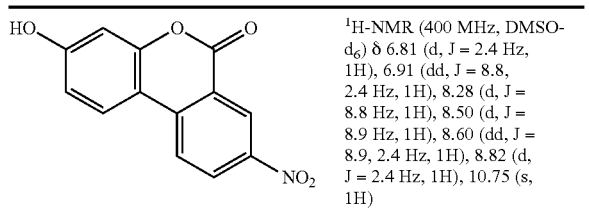

| | ¹H-NMR (400 MHz, DMSO-d₆) δ 6.81 (d, J = 2.4 Hz, 1H), 6.91 (dd, J = 8.8, 2.4 Hz, 1H), 8.28 (d, J = 8.8 Hz, 1H), 8.50 (d, J = 8.9 Hz, 1H), 8.60 (dd, J = 8.9, 2.4 Hz, 1H), 8.82 (d, J = 2.4 Hz, 1H), 10.75 (s, 1H) |
|---|---|

8-Amino-3-hydroxybenzo[c]chromen-6-one (Reference Compound No. 1-(3))

3-Hydroxy-8-nitrobenzo[c]chromen-6-one (Reference Compound No. 1-(2), 52.01 g, 202 mmol) was dissolved in methanol (150 mL) N,N-dimethylformamide (600 mL), 10% palladium on charcoal (5.00 g) was added thereto, and then the reaction mixture was stirred under hydrogen atmosphere (3 kgf/cm²) at room temperature overnight. After the unsoluble materials were filtered out, the methanol was removed under reduced pressure. Water (2 L) was added to the residue. The precipitated solid was filtered off and dried at 90° C. under reduced pressure to give the titled reference compound (44.02 g) as a pale yellow solid. (Yield 96%)

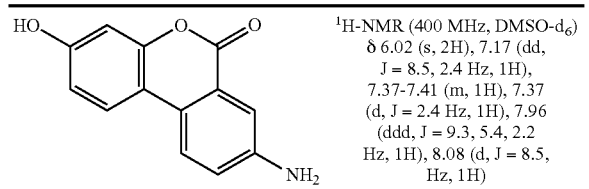

| | ¹H-NMR (400 MHz, DMSO-d₆) δ 6.02 (s, 2H), 7.17 (dd, J = 8.5, 2.4 Hz, 1H), 7.37-7.41 (m, 1H), 7.37 (d, J = 2.4 Hz, 1H), 7.96 (ddd, J = 9.3, 5.4, 2.2 Hz, 1H), 8.08 (d, J = 8.5, Hz, 1H) |
|---|---|

8-Hydroxy-2,2,4-trimethyl-1,2-dihydro-6-oxa-1-azachrysen-5-one (Reference Compound No. 1-(4))

In a pressure tube, 8-amino-3-hydroxybenzo[c]chromen-6-one (Reference Compound No. 1-(3), 40.0 g, 176 mmol) was dissolved in acetone (440 mL)-N-methylpyrrolidone (240 mL), iodine (17.9 g, 70.5 mmol) was added thereto, the pressure tube was sealed, and then the reaction mixture was stirred at 110° C. for 3 days. After cooling down, acetone was removed under reduced pressure. To the obtained residue, ethyl acetate (700 mL), hexane (150 mL) and 1% aqueous sodium thiosulfate solution (700 mL) were added thereto and the mixture was separated into a water phase and an organic layer. The water layer was extracted with a mixed solvent of ethyl acetate (250 mL)-hexane (50 mL) (3 times). The combined organic layer was washed with water (500 mL, 3 times) and saturated brine (500 mL) successively, dried over anhydrous magnesium sulfate, and then the solvent was removed under reduced pressure. To the obtained residue, chloroform (150 mL) was added and the unsoluble materials were filtered out. After the filtrate was concentrated, the residue was purified by silica gel column chromatography (hexane-ethyl acetate) to give the titled reference compound (26.0 g) as a yellow solid. (Yield 48%)

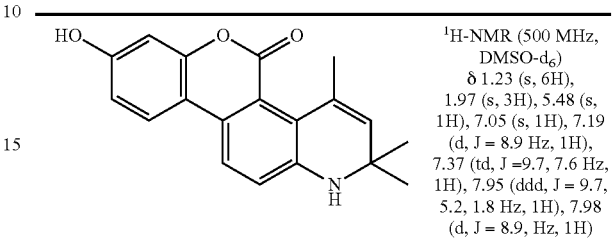

| | ¹H-NMR (500 MHz, DMSO-d₆) δ 1.23 (s, 6H), 1.97 (s, 3H), 5.48 (s, 1H), 7.05 (s, 1H), 7.19 (d, J = 8.9 Hz, 1H), 7.37 (td, J =9.7, 7.6 Hz, 1H), 7.95 (ddd, J = 9.7, 5.2, 1.8 Hz, 1H), 7.98 (d, J = 8.9, Hz, 1H) |
|---|---|

8-Methoxymethoxy-2,2,4-trimethyl-1,2-dihydro-6-oxa-1-azachrysen-5-one (Reference Compound No. 1-(5))

A mixture of 8-hydroxy-2,2,4-trimethyl-1,2-dihydro-6-oxa-1-azachrysen-5-one (Reference Compound No. 1-(4), 1.00 g, 3.25 mmol), chlorodimethylether (420 µL, 5.53 mmol) and potassium carbonate (1.35 g, 9.77 mmol) was suspended in anhydrous N,N-dimethylformamide (15 mL) and the suspension was stirred at 50° C. overnight. After cooling down, ethyl acetate (100 mL) and diethylether (100 mL) were added thereto. The whole was washed with water (150 mL, 100 mL) and saturated brine (100 mL) successively, dried over anhydrous magnesium sulfate, and then the solvent was removed under reduced pressure. The obtained residue was purified by silica gel column chromatography (hexane-ethyl acetate) to give the titled reference compound (747 mg) as a yellow solid. (Yield 66%)

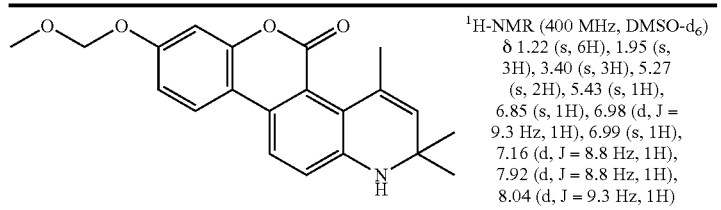

| | ¹H-NMR (400 MHz, DMSO-d₆) δ 1.22 (s, 6H), 1.95 (s, 3H), 3.40 (s, 3H), 5.27 (s, 2H), 5.43 (s, 1H), 6.85 (s, 1H), 6.98 (d, J = 9.3 Hz, 1H), 6.99 (s, 1H), 7.16 (d, J = 8.8 Hz, 1H), 7.92 (d, J = 8.8 Hz, 1H), 8.04 (d, J = 9.3 Hz, 1H) |
|---|---|

6-(2-Hydroxy-4-methoxymethoxyphenyl)-5-hydroxymethyl-2,2,4-trimethyl-1,2-dihydroquioline (Reference Compound No. 1-(6))

Lithium aluminum hydride (167 mg, 4.40 mmol) was suspended in anhydrous tetrahydrofuran (3 mL). A solution of 8-methoxymethoxy-2,2,4-trimethyl-1,2-dihydro-6-oxa-1-azachrysen-5-one (Reference Compound No. 1-(5), 744.1 mg, 2.12 mmol) in anhydrous tetrahydrofuran (10 mL) was added dropwise to the suspension at 0° C., the reaction mixture was stirred at the same temperature for 30 minutes. Ethyl acetate (2 mL) and water (1 mL) were added to the reaction mixture successively, and then ethyl acetate (150 mL) was added thereto. 1N aqueous HCl solution (6 mL) was added, the mixture was washed with water (100 mL, twice) and saturated brine (50 mL) successively, and then dried over anhydrous magnesium sulfate. The solvent was removed under reduced pressure to give the titled reference compound (750.6 mg) as a pale yellow amorphous product. (Quantitative)

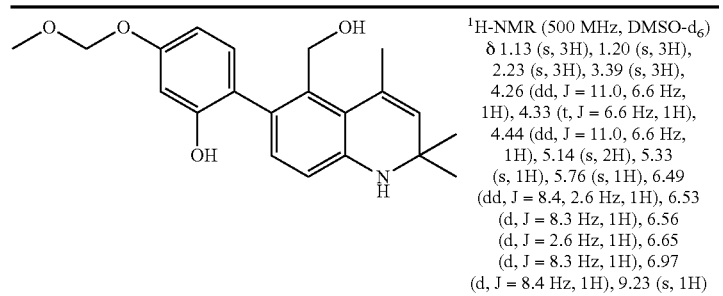

$^1$H-NMR (500 MHz, DMSO-$d_6$) δ 1.13 (s, 3H), 1.20 (s, 3H), 2.23 (s, 3H), 3.39 (s, 3H), 4.26 (dd, J = 11.0, 6.6 Hz, 1H), 4.33 (t, J = 6.6 Hz, 1H), 4.44 (dd, J = 11.0, 6.6 Hz, 1H), 5.14 (s, 2H), 5.33 (s, 1H), 5.76 (s, 1H), 6.49 (dd, J = 8.4, 2.6 Hz, 1H), 6.53 (d, J = 8.3 Hz, 1H), 6.56 (d, J = 2.6 Hz, 1H), 6.65 (d, J = 8.3 Hz, 1H), 6.97 (d, J = 8.4 Hz, 1H), 9.23 (s, 1H)

5-Hydroxymethyl-6-(2-methoxy-4-methoxymethoxyphenyl)-2,2,4-trimethyl-1,2-dihydroquioline (Reference Compound No. 1)

A mixture of 6-(2-hydroxy-4-methoxymethoxyphenyl)-5-hydroxymethyl-2,2,4-trimethyl-1,2-dihydroquinoline (Reference Compound No. 1-(6), 746.1 mg, 2.10 mmol), methyl iodide (131 µL, 2.10 mmol) and potassium carbonate (582 mg, 4.21 mmol) was suspended in anhydrous N,N-dimethylformamide (10 mL) and the suspension was stirred at 50° C. for 1 hour. After cooling down, the mixture was diluted with ethyl acetate (50 mL) and diethylether (50 mL). The mixture was washed with water (100 mL, twice) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (513.2 mg) as a colorless solid. (Yield 66%)

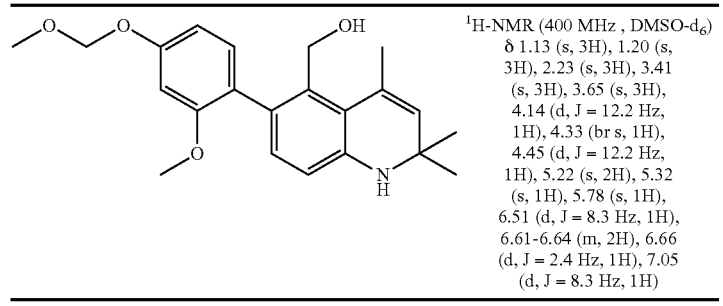

$^1$H-NMR (400 MHz, DMSO-$d_6$) δ 1.13 (s, 3H), 1.20 (s, 3H), 2.23 (s, 3H), 3.41 (s, 3H), 3.65 (s, 3H), 4.14 (d, J = 12.2 Hz, 1H), 4.33 (br s, 1H), 4.45 (d, J = 12.2 Hz, 1H), 5.22 (s, 2H), 5.32 (s, 1H), 5.78 (s, 1H), 6.51 (d, J = 8.3 Hz, 1H), 6.61-6.64 (m, 2H), 6.66 (d, J = 2.4 Hz, 1H), 7.05 (d, J = 8.3 Hz, 1H)

Reference Example 2

5-Chloromethyl-6-(2-methoxy-4-methoxymethoxyphenyl)-2,2,4-trimethyl-1,2-dihydroquioline (Reference Compound No. 2)

5-Hydroxymethyl-6-(2-methoxy-4-methoxymethoxyphenyl)-2,2,4-trimethyl-1,2-dihydroquioline (Reference Compound No. 1, 1.02 g, 2.76 mmol) was dissolved in anhydrous methylene dichloride (10 mL), and then triethylamine (0.490 mL, 3.52 mmol) and methanesulfonyl chloride (231 μL, 2.98 mmol) were added successively. The reaction mixture was stirred at room temperature for 5 hours. Chloroform (50 mL) and water (50 mL) were added to the reaction mixture and separated. The organic layer was washed with saturated brine (50 mL), dried over anhydrous magnesium sulfate, and then the solvent was removed under reduced pressure. The obtained residue was purified by silica gel column chromatography (hexane-ethyl acetate) to give the titled reference compound (515 mg) as an orange amorphous product. (Yield 49%)

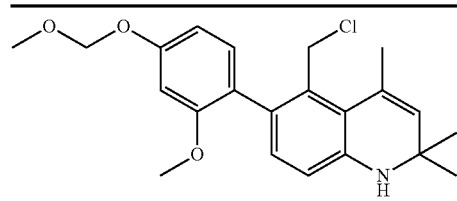

$^1$H-NMR (400 MHz, DMSO-$d_6$) δ 1.14 (s, 3H), 1.20 (s, 3H), 2.26 (s, 3H), 3.42 (s, 3H), 3.67 (s, 3H), 4.40 (d, J = 11.7 Hz, 1H), 4.80 (d, J = 11.7 Hz, 1H), 5.23 (s, 2H), 5.45 (s, 1H), 6.01 (br s, 1H), 6.60 (d, J = 8.2 Hz, 1H), 6.66 (dd, J = 8.3, 2.4 Hz, 1H), 6.66 (d, J = 8.2 Hz, 1H), 6.70 (d, J = 2.4 Hz, 1H), 7.03 (d, J = 8.3 Hz, 1H)

Reference Example 3

6-(2-Methoxy-4-methoxymethoxyphenyl)-5-(2-methoxyphenylaminomethyl)-2,2,4-trimethyl-1,2-dihydroquioline (Reference Compound No. 3-1)

A mixture of 5-chloromethyl-6-(2-methoxy-4-methoxymethoxyphenyl)-2,2,4-trimethyl-1,2-dihydroquioline (Reference Compound No. 2, 262 mg, 0.675 mmol), 2-methoxyaniline (84 μL, 0.74 mmol) and potassium carbonate (151 mg, 1.09 mmol) was suspended in anhydrous N,N-dimethylformamide (4 mL) and the suspension was stirred at 80° C. overnight. After cooling down, ethyl acetate (20 mL) and water (20 mL) were added to the reaction mixture and separated. The organic layer was washed with saturated brine (20 mL), dried over anhydrous magnesium sulfate, and then the solvent was removed under reduced pressure. The obtained residue was purified by silica gel column chromatography (hexane-ethyl acetate) to give the titled reference compound (196 mg) as a yellow amorphous product. (Yield 61%)

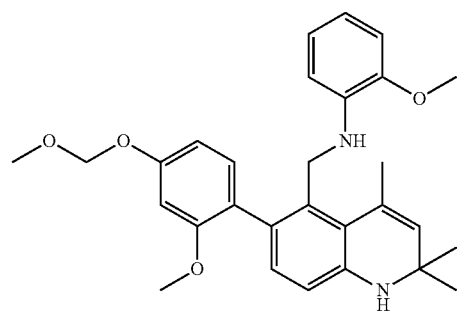

$^1$H-NMR (400 MHz, DMSO-$d_6$) δ 1.14 (s, 3H), 1.21 (s, 3H), 2.06 (s, 3H), 3.37 (s, 3H), 3.64 (s, 3H), 3.71 (s, 3H), 3.84 (dd, J = 12.1, 3.3 Hz, 1H), 4.03 (dd, J = 12.1, 6.5 Hz, 1H), 4.23 (dd, J = 6.5, 3.3 Hz, 1H), 5.17 (s, 2H), 5.38 (s, 1H), 5.95 (s, 1H), 6.36 (dd, J = 7.8, 1.4 Hz, 1H), 6.50 (td, J = 7.8, 1.4 Hz, 1H), 6.58 (dd, J = 8.3, 1.0 Hz, 1H), 6.58 (d, J = 8.2 Hz, 1H), 6.61 (d, J = 1.9 Hz, 1H), 6.67 (td, J = 7.8, 1, 2 Hz, 1H), 6.67 (d, J = 8.2 Hz, 1H), 6.73 (dd, J = 7.8, 1.2 Hz, 1H), 6.98 (d, J = 8.3 Hz, 1H)

Using Reference Compound No. 2, the following Reference Compound (No. 3-2) was obtained by a method similar to that of Reference Compound No. 3-1.

| | |
|---|---|
| 5-(5-Fluoro-2-methylphenyl aminomethyl)-6-(2-methoxy-4-methoxymethoxyphenyl)-2,2,4-trimethyl-1,2-dihydroquioline (Reference Compound No. 3-2) 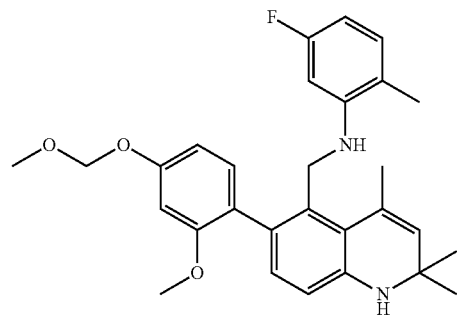 | $^1$H-NMR (400 MHz, DMSO-$d_6$) δ 1.09 (s, 3H), 1.19 (s, 3H), 1.89 (s, 3H), 2.03 (s, 3H), 3.38 (s, 3H), 3.69 (s, 3H), 3.93 (dd, J = 13.2, 5.0 Hz, 1H), 4.06 (dd, J = 13.2, 4.3 Hz, 1H), 4.17-4.19 (m, 1H), 5.19 (s, 2H), 5.39 (s, 1H), 5.96 (s, 1H), 6.05 (dd, J = 12.2, 2.6 Hz, 1H), 6.20 (td, J = 8.5, 2.6 Hz, 1H), 6.59 (d, J = 8.3 Hz, 1H), 6.61 (dd, J = 8.5, 2.6 Hz, 1H), 6.67 (d, J = 2.6 Hz, 1H), 6.70 (d, J = 8.3 Hz, 1H), 6.85-6.89 (m, 1H), 7.07 (d, J = 8.5 Hz, 1H) |

Reference Example 4

6-(4-Hydroxy-2-methoxyphenyl)-5-(2-methoxyphenylaminomethyl)-2,2,4-trimethyl-1,2-dihydroquioline (Reference Compound No. 4-1)

6-(2-Methoxy-4-methoxymethoxyphenyl)-5-(2-methoxyphenylaminomethyl)-2,2,4-trimethyl-1,2-dihydroquinoline (Reference Compound No. 3-1, 181 mg, 0.381 mmol) was dissolved in 1,4-dioxane (3 mL), 4N HCl/1,4-dioxane solution (1 mL) was added thereto, and then the mixture was stirred at room temperature for 2.5 hours. The mixture was diluted with ethyl acetate (30 mL), washed with saturated aqueous sodium hydrogen carbonate solution (30 mL), water (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled reference compound (101 mg) as a pale orange solid. (Yield 62%)

| | |
|---|---|
| 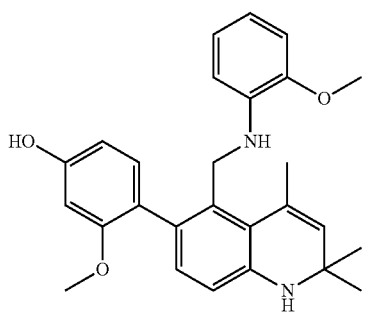 [SMILES: COc1ccccc1NCc1c(-c2ccc(O)cc2OC)ccc2c1C(C)=CC(C)(C)N2] | $^1$H-NMR (500 MHz, DMSO-$d_6$) δ 1.13 (s, 3H), 1.21 (s, 3H), 2.06 (s, 3H), 3.59 (s, 3H), 3.71 (s, 3H), 3.83 (dd, J = 12.2, 3.4 Hz, 1H), 4.02 (dd, J = 12.2, 6.7 Hz, 1H), 4.23 (dd, J = 6.7, 3.4 Hz, 1H), 5.37 (s, 1H), 5.90 (s, 1H), 6.31 (dd, J = 8.2, 2.2 Hz, 1H), 6.35 (dd, J = 7.7, 1.6 Hz, 1H), 6.36 (d, J = 2.2 Hz, 1H), 6.50 (td, J = 7.7, 1.6 Hz, 1H), 6.56 (d, J = 8.1 Hz, 1H), 6.66 (d, J = 8.1 Hz, 1H), 6.68 (td, J = 7.7, 1.2 Hz, 1H), 6.73 (dd, J = 7.7, 1.2 Hz, 1H), 6.84 (d, J = 8.2 Hz, 1H), 9.36 (s, 1H) |

Using Reference Compound No. 3-2, the following Reference Compound (No. 4-2) was obtained by a method similar to that of Reference Compound No. 4-1.

| | |
|---|---|
| 5-(5-Fluoro-2-methylphenyl aminomethyl)-6-(4-hydroxy-2-methoxyphenyl)-2,2,4-trimethyl-1,2-dihydroquioline (Reference Compound No. 4-2)<br>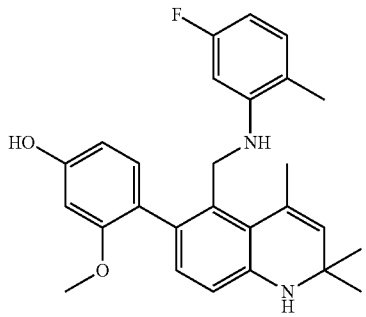 | $^1$H-NMR (400 MHz, DMSO-$d_6$) δ 1.09 (s, 3H), 1.19 (s, 3H), 1.89 (s, 3H), 2.04 (s, 3H), 3.65 (s, 3H), 3.93 (dd, J = 13.3, 6.7 Hz, 1H), 4.02-4.07 (m, 1H), 4.14-4.17 (m, 1H), 5.39 (s, 1H), 5.93 (s, 1H), 6.06 (dd, J = 12.1, 2.5 Hz, 1H), 6.20 (td, J = 8.4, 2.5 Hz, 1H), 6.35 (dd, J = 8.1, 2.2 Hz, 1H), 6.42 (d, J = 2.2 Hz, 1H), 6.57 (d, J = 8.2 Hz, 1H), 6.69 (d, J = 8.2 Hz, 1H), 6.86-6.89 (m, 1H), 6.93 (d, J = 8.1 Hz, 1H), 9.41 (s, 1H) |

Reference Example 5

6-(4-Hydroxy-2-methoxyphenyl)-5-[N-(2-methoxyphenyl)-N-(9-fluorenylmethoxycarbonyl)aminomethyl]-2,2,4-trimethyl-1,2-dihydroquioline (Reference Compound No. 5)

6-(4-Hydroxy-2-methoxyphenyl)-5-(2-methoxyphenylaminomethyl)-2,2,4-trimethyl-1,2-dihydroquioline (Reference Compound No. 4-1, 37.7 mg, 0.0876 mmol) and sodium hydrogen carbonate (9.5 mg, 0.113 mmol) were dissolved in 1,4-dioxane (0.5 mL)-water (0.5 mL), and then 9-fluorenylmethoxycarbonyl chloride (25.6 mg, 0.0990 mmol) was added thereto under ice cooling. After the reaction mixture was stirred at room temperature for 3 hours, it was diluted with ethyl acetate (10 mL). The mixture was washed with 1N aqueous HCl solution (10 mL), water (10 mL) and saturated brine (10 mL) successively, dried over anhydrous magnesium sulfate, and then the solvent was removed under reduced pressure. The obtained residue was purified by silica gel column chromatography (hexane-ethyl acetate) to give the titled reference compound (19.7 mg) as a colorless amorphous product. (Yield 34%)

| | |
|---|---|
| | $^1$H-NMR (400 MHz, DMSO-$d_6$) δ 1.22 (s, 3H), 1.28 (s, 3H), 2.20 (s, 3H), 3.29 (s, 3H), 3.61 (s, 3H), 3.89 (s, 2H), 5.30 (d, J = 14.3 Hz, 1H), 5.45 (s, 1H), 5.81 (d, J = 14.3 Hz, 1H), 5.85 (s, 1H), 6.22 (dd, J = 8.2, 2.1 Hz, 1H), 6.34-6.35 (m, 2H), 6.43 (d, J = 8.3 Hz, 1H), 6.63-6.65 (m, 2H), 6.87-6.91 (m, 3H), 7.09-7.25 (m, 4H), 7.31-7.35 (m, 2H), 7.79 (d, J = 7.6 Hz, 2H), 9.32 (s, 1H) |

Example 1

6-[4-(Furan-2-ylcarbonyloxy)-2-methoxyphenyl]-5-(2-methoxyphenylaminomethyl)-2,2,4-trimethyl-1,2-dihydroquioline (Compound No. 1-1)

6-(4-Hydroxy-2-methoxyphenyl)-5-[N-(2-methoxyphenyl)-N-(9-fluorenylmethoxycarbonyl)aminomethyl]-2,2,4-trimethyl-1,2-dihydroquioline (Reference Compound No. 5, 17.4 mg, 0.0267 mmol) was dissolved in methylene dichloride (0.5 mL), and then triethylamine (10 μL, 0.072 mmol) and 2-furoyl chloride (3.6 μL, 0.036 mmol) were added thereto successively. After the reaction mixture was stirred at room temperature for 3 hours, the reaction mixture was purified by silica gel column chromatography (hexane-ethyl acetate) to give a colorless amorphous product (15.6 mg). The obtained colorless amorphous product (11.8 mg) was dissolved in N,N-dimethylformamide (0.3 mL) and piperidine (15.6 μL, 0.158 mmoL) was added thereto. After the reaction mixture was stirred at room temperature for 1 minute, it was diluted with ethyl acetate (10 mL). The reaction mixture was washed with water (10 mL) and saturated brine (10 mL) successively, dried over anhydrous magnesium sulfate, and then the solvent was removed under reduced pressure. The obtained residue was purified by silica gel column chromatography (hexane-ethyl acetate) to give the titled compound (6.0 mg) as a colorless solid. (Yield 76%)

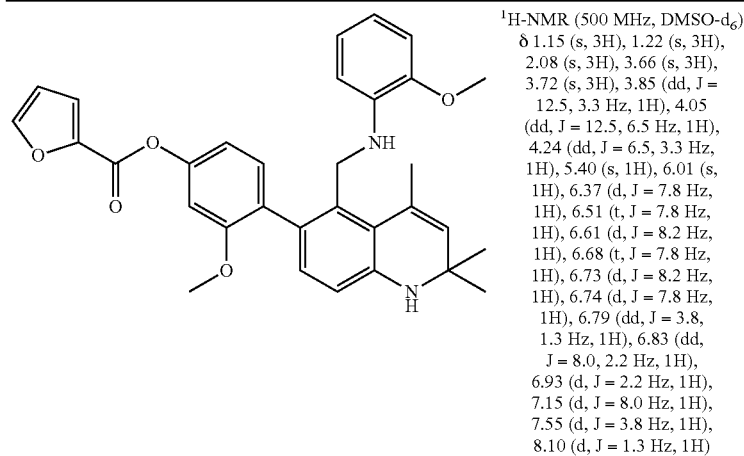

$^1$H-NMR (500 MHz, DMSO-$d_6$) δ 1.15 (s, 3H), 1.22 (s, 3H), 2.08 (s, 3H), 3.66 (s, 3H), 3.72 (s, 3H), 3.85 (dd, J = 12.5, 3.3 Hz, 1H), 4.05 (dd, J = 12.5, 6.5 Hz, 1H), 4.24 (dd, J = 6.5, 3.3 Hz, 1H), 5.40 (s, 1H), 6.01 (s, 1H), 6.37 (d, J = 7.8 Hz, 1H), 6.51 (t, J = 7.8 Hz, 1H), 6.61 (d, J = 8.2 Hz, 1H), 6.68 (t, J = 7.8 Hz, 1H), 6.73 (d, J = 8.2 Hz, 1H), 6.74 (d, J = 7.8 Hz, 1H), 6.79 (dd, J = 3.8, 1.3 Hz, 1H), 6.83 (dd, J = 8.0, 2.2 Hz, 1H), 6.93 (d, J = 2.2 Hz, 1H), 7.15 (d, J = 8.0 Hz, 1H), 7.55 (d, J = 3.8 Hz, 1H), 8.10 (d, J = 1.3 Hz, 1H)

6-[2-Methoxy-4-(2-methylpyridin-3-ylcarbonyloxy) phenyl]-5-(2-methoxyphenylaminomethyl)-2,2,4-trimethyl-1,2-dihydroquioline (Compound No. 1-2)

A mixture of 6-(4-hydroxy-2-methoxyphenyl)-5-(2-methoxyphenylaminomethyl)-2,2,4-trimethyl-1,2-dihydroquioline (Reference Compound No. 4-1, 25.0 mg, 0.0581 mmol), 2-methylnicotinoic acid (8.0 mg, 0.058 mmol), N,N-diisopropylethylamine (20.2 μL, 0.116 mmol) and O-(7-azabenzotriazol-1-yl)-N,N,N,N-tetramethyluronium hexafluorophosphate (24.3 mg, 0.0639 mmol) was dissolved in anhydrous N,N-dimethylformamide (0.5 mL), and then the reaction mixture was stirred at room temperature overnight. The reaction mixture was diluted with ethyl acetate (70 mL). The mixture was washed with water (70 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (20.7 mg) as a colorless solid. (Yield 65%)

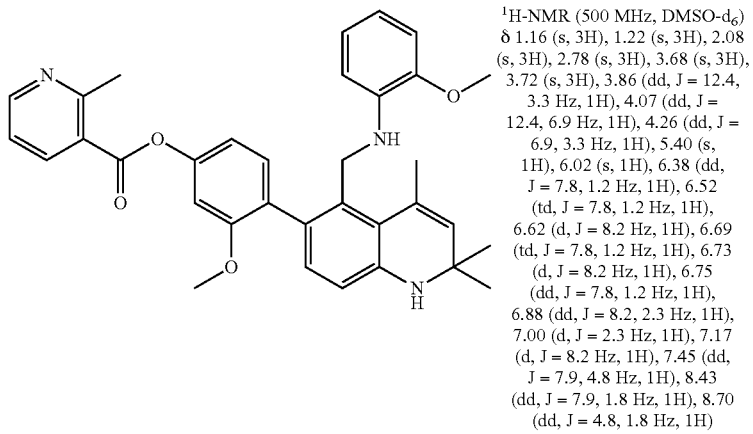

$^1$H-NMR (500 MHz, DMSO-$d_6$)
δ 1.16 (s, 3H), 1.22 (s, 3H), 2.08 (s, 3H), 2.78 (s, 3H), 3.68 (s, 3H), 3.72 (s, 3H), 3.86 (dd, J = 12.4, 3.3 Hz, 1H), 4.07 (dd, J = 12.4, 6.9 Hz, 1H), 4.26 (dd, J = 6.9, 3.3 Hz, 1H), 5.40 (s, 1H), 6.02 (s, 1H), 6.38 (dd, J = 7.8, 1.2 Hz, 1H), 6.52 (td, J = 7.8, 1.2 Hz, 1H), 6.62 (d, J = 8.2 Hz, 1H), 6.69 (td, J = 7.8, 1.2 Hz, 1H), 6.73 (d, J = 8.2 Hz, 1H), 6.75 (dd, J = 7.8, 1.2 Hz, 1H), 6.88 (dd, J = 8.2, 2.3 Hz, 1H), 7.00 (d, J = 2.3 Hz, 1H), 7.17 (d, J = 8.2 Hz, 1H), 7.45 (dd, J = 7.9, 4.8 Hz, 1H), 8.43 (dd, J = 7.9, 1.8 Hz, 1H), 8.70 (dd, J = 4.8, 1.8 Hz, 1H)

6-(4-Benzoyloxy-2-methoxyphenyl)-5-(2-methoxyphenylaminomethyl)-2,2,4-trimethyl-1,2-dihydroquioline (Compound No. 1-3)

6-(4-Hydroxy-2-methoxyphenyl)-5-(2-methoxyphenylaminomethyl)-2,2,4-trimethyl-1,2-dihydroquioline (Reference Compound No. 4-1, 25.0 mg, 0.0581 mmol) was dissolved in methylene dichloride (0.5 mL), and then triethylamine (16.2 μL, 0.116 mmol) and benzoyl chloride (8.7 μL, 0.075 mmol) were added thereto successively under ice cooling. The reaction mixture was stirred under ice cooling for 30 minutes. The reaction mixture was purified by silica gel column chromatography (hexane-ethyl acetate) to give the titled compound (13.0 mg) as a colorless amorphous product. (Yield 65%)

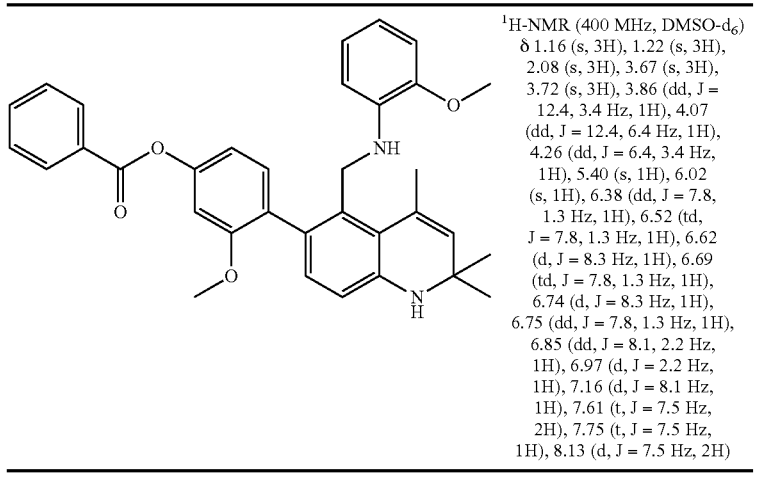

$^1$H-NMR (400 MHz, DMSO-$d_6$)
δ 1.16 (s, 3H), 1.22 (s, 3H), 2.08 (s, 3H), 3.67 (s, 3H), 3.72 (s, 3H), 3.86 (dd, J = 12.4, 3.4 Hz, 1H), 4.07 (dd, J = 12.4, 6.4 Hz, 1H), 4.26 (dd, J = 6.4, 3.4 Hz, 1H), 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.3 Hz, 1H), 6.69 (td, J = 7.8, 1.3 Hz, 1H), 6.74 (d, J = 8.3 Hz, 1H), 6.75 (dd, J = 7.8, 1.3 Hz, 1H), 6.85 (dd, J = 8.1, 2.2 Hz, 1H), 6.97 (d, J = 2.2 Hz, 1H), 7.16 (d, J = 8.1 Hz, 1H), 7.61 (t, J = 7.5 Hz, 2H), 7.75 (t, J = 7.5 Hz, 1H), 8.13 (d, J = 7.5 Hz, 2H)

Using any compounds among Reference Compounds No. 4-1, 4-2 or 5, the following Compounds (No. 1-4~1-45) were obtained by a method similar to that of Compound No. 1-1, 1-2 or 1-3.

---

6-[2-Methoxy-4-(2-methoxybenzoyloxy) phenyl]-5-(2-methoxyphenylaminomethyl)-2,2,4-trimethyl-1,2-dihydroquioline (Compound No. 1-4)

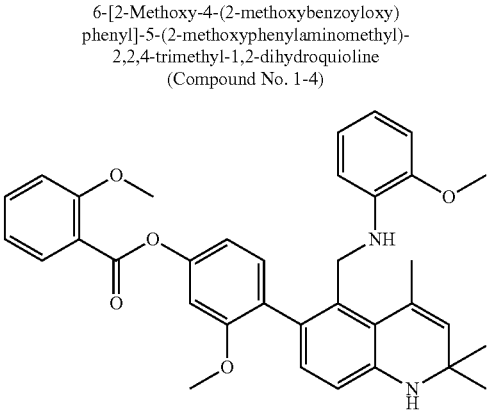 [SMILES: COc1ccccc1NCc1c(-c2ccc(OC(=O)c3ccccc3OC)cc2OC)ccc2c1C(C)=CC(C)(C)N2]

$^1$H-NMR (500 MHz, DMSO-d$_6$) δ 1.16 (s, 3H), 1.22 (s, 3H), 2.06 (s, 3H), 3.67 (s, 3H), 3.72 (s, 3H), 3.85-3.88 (m, 1H), 3.86 (s, 3H), 4.05-4.09 (m, 1H), 4.24-4.26 (m, 1H), 5.40 (s, 1H), 6.01 (s, 1H), 6.38 (dd, J = 7.7, 1.2 Hz, 1H), 6.52 (td, J = 7.7, 1.2 Hz, 1H), 6.62 (d, J = 8.2 Hz, 1H), 6.69 (td, J = 7.7, 1.2 Hz, 1H), 6.73 (d, J = 8.2 Hz, 1H), 6.73-6.75 (m, 1H), 6.80 (dd, J = 8.0, 2.3 Hz, 1H), 6.89 (d, J = 2.3 Hz, 1H), 7.07-7.10 (m, 1H), 7.15 (d, J = 8.0 Hz, 1H), 7.22 (d, J = 7.9 Hz, 1H), 7.63 (td, J = 7.9, 1.7 Hz, 1H), 7.90 (dd, J = 7.9, 1.7 Hz, 1H)

---

6-[2-Methoxy-4-(2-methoxybenzoyloxy) phenyl]-5-(2-methoxyphenylaminomethyl)-2,2,4-trimethyl-1,2-dihydroquioline (Compound No. 1-5)

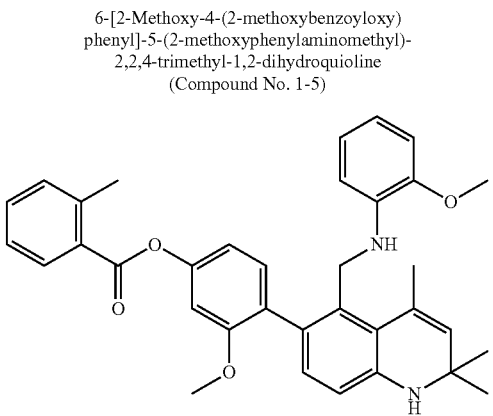 [SMILES: COc1ccccc1NCc1c(-c2ccc(OC(=O)c3ccccc3C)cc2OC)ccc2c1C(C)=CC(C)(C)N2]

$^1$H-NMR (400 MHz, DMSO-d$_6$) δ 1.03 (s, 3H), 1.22 (s, 3H), 2.06 (s, 3H), 2.59 (s, 3H), 3.68 (s, 3H), 3.72 (s, 3H), 3.85-3.88 (m, 1H), 4.05-4.07 (m, 1H), 4.25-4.26 (m, 1H), 5.40 (s, 1H), 6.02 (s, 1H), 6.39 (d, J = 7.8 Hz, 1H), 6.52 (t, J = 7.8 Hz, 1H), 6.63 (d, J = 8.2 Hz, 1H), 6.70 (t, J = 7.8 Hz, 1H), 6.74 (d, J = 8.2 Hz, 1H), 6.75 (d, J = 7.8 Hz, 1H), 6.85 (dd, J = 8.2, 2.2 Hz, 1H), 6.96 (d, J = 2.2 Hz, 1H), 7.15 (d, J = 8.2 Hz, 1H), 7.37-7.42 (m, 2H), 7.56 (t, J = 7.7 Hz, 1H), 8.07 (d, J = 7.7 Hz, 1H)

---

6-[4-(Furan-3-ylcarbonyloxy)-2-methoxyphenyl]-5-(2-methoxyphenylaminomethyl)-2,2,4-trimethyl-1,2-dihydroquioline (Compound No. 1-6)

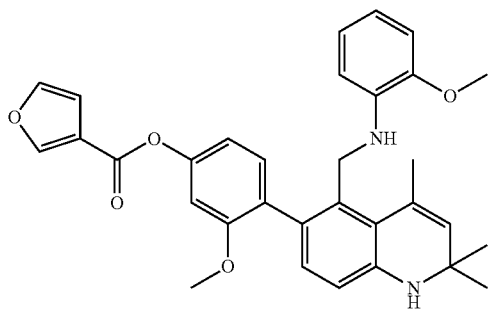

$^1$H-NMR (500 MHz, DMSO-d$_6$) δ 1.15 (s, 3H), 1.22 (s, 3H), 2.08 (s, 3H), 3.66 (s, 3H), 3.72 (s, 3H), 3.81-3.84 (m, 1H), 4.02-4.05 (m, 1H), 4.24-4.26 (m, 1H), 5.40 (s, 1H), 6.02 (s, 1H), 6.36 (d, J = 7.7 Hz, 1H), 6.52 (t, J = 7.7 Hz, 1H), 6.62 (d, J = 8.3 Hz, 1H), 6.69 (t, J = 7.7 Hz, 1H), 6.73 (d, J = 8.3 Hz, 1H), 6.73-6.75 (m, 1H), 6.80 (dd, J = 8.2, 2.3 Hz, 1H), 6.89 (d, J = 2.3 Hz, 1H), 6.93 (dd, J = 1.7, 0.8 Hz, 1H), 7.14 (d, J = 8.2 Hz, 1H), 7.90 (t, J = 1.7 Hz, 1H), 8.62 (dd, J = 1.7, 0.8 Hz, 1H)

| Compound | NMR |
|---|---|
| 5-(2-Methoxyphenylaminomethyl)-6-[2-methoxy-4-(thiophen-3-ylcarbonyloxy)phenyl]-2,2,4-trimethyl-1,2-dihydroquioline (Compound No. 1-7) 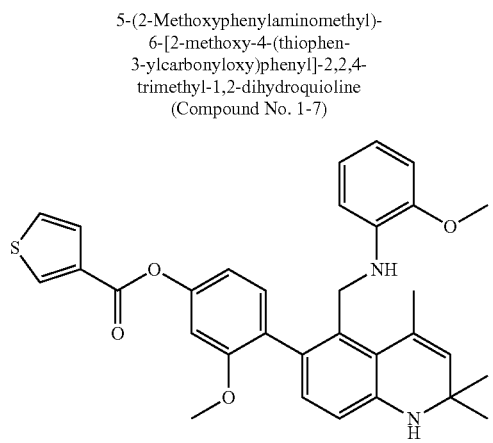 [SMILES: COc1ccccc1NCc1c(-c2ccc(OC(=O)c3ccsc3)cc2OC)ccc2c1C(C)=CC(C)(C)N2] | $^1$H-NMR (500 MHz, DMSO-d$_6$) δ 1.16 (s, 3H), 1.22 (s, 3H), 2.08 (s, 3H), 3.66 (s, 3H), 3.72 (s, 3H), 3.83-3.86 (m, 1H), 4.05-4.08 (m, 1H), 4.24-4.26 (m, 1H), 5.40 (s, 1H), 6.01 (s, 1H), 6.36 (dd, J = 7.7, 1.3 Hz, 1H), 6.52 (td, J = 7.7, 1.3 Hz, 1H), 6.62 (d, J = 8.2 Hz, 1H), 6.69 (td, J = 7.7, 1.3 Hz, 1H), 6.74 (d, J = 8.2 Hz, 1H), 6.74 (dd, J = 7.7, 1.3 Hz, 1H), 6.82 (dd, J = 8.3, 2.1 Hz, 1H), 6.92 (d, J = 2.1 Hz, 1H), 7.15 (d, J = 8.3 Hz, 1H), 7.14 (dd, J = 5.1, 1.4 Hz, 1H), 7.74 (dd, J = 5.1, 2.9 Hz, 1H), 8.59 (dd, J = 2.9, 1.4 Hz, 1H) |
| 5-(2-Methoxyphenylaminomethyl)-6-[2-methoxy-4-(pyridin-3-ylcarbonyloxy)phenyl]-2,2,4-trimethyl-1,2-dihydroquioline (Compound No. 1-8) 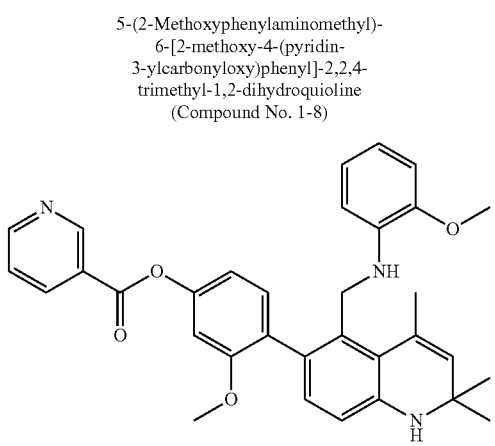 [SMILES: COc1ccccc1NCc1c(-c2ccc(OC(=O)c3cccnc3)cc2OC)ccc2c1C(C)=CC(C)(C)N2] | $^1$H-NMR (500 MHz, DMSO-d$_6$) δ 1.16 (s, 3H), 1.22 (s, 3H), 2.08 (s, 3H), 3.67 (s, 3H), 3.72 (s, 3H), 3.86 (dd, J = 12.2, 3.3 Hz, 1H), 4.06-4.09 (m, 1H), 4.25 (dd, J = 6.8, 3.3 Hz, 1H), 5.40 (s, 1H), 6.02 (s, 1H), 6.38 (dd, J = 7.7, 1.4 Hz, 1H), 6.52 (td, J = 7.7, 1.4 Hz, 1H), 6.62 (d, J = 8.2 Hz, 1H), 6.69 (td, J = 7.7, 1.4 Hz, 1H), 6.74 (d, J = 8.2 Hz, 1H), 6.74-6.76 (m, 1H), 6.90 (dd, J = 8.3, 2.2 Hz, 1H), 7.02 (d, J = 2.2 Hz, 1H), 7.17 (d, J = 8.3 Hz, 1H), 7.65 (ddd, J = 7.9, 4.9, 0.9 Hz, 1H), 8.46 (dt, J = 7.9, 2.0 Hz, 1H), 8.90 (dd, J = 4.9, 2.0 Hz, 1H), 9.26 (dd, J = 2.0, 0.9 Hz, 1H) |
| 6-[4-(2-Chlorobenzoyloxy)-2-methoxyphenyl]-5-(5-fluoro-2-methylphenylaminomethyl)-2,2,4-trimethyl-1,2-dihydroquioline (Compound No. 1-9) 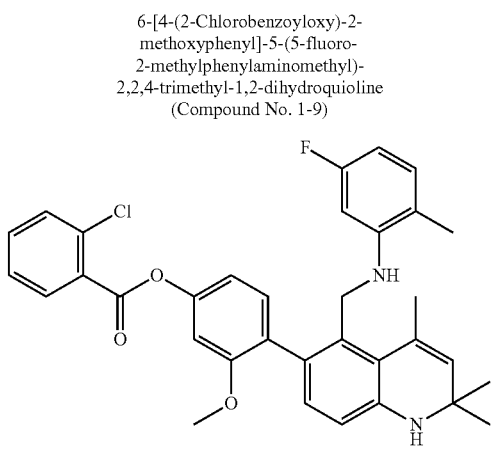 [SMILES: COc1cc(OC(=O)c2ccccc2Cl)ccc1-c1ccc2c(c1CNc1cc(F)ccc1C)C(C)=CC(C)(C)N2] | $^1$H-NMR (400 MHz, DMSO-d$_6$) δ 1.11 (s, 3H), 1.20 (s, 3H), 1.91 (s, 3H), 2.05 (s, 3H), 3.74 (s, 3H), 3.95 (dd, J = 13.1, 5.2 Hz, 1H), 4.10 (dd, J = 13.1, 4.2 Hz, 1H), 4.25 (br s, 1H), 5.41 (s, 1H), 6.04 (s, 1H), 6.07 (dd, J = 12.1, 2.5 Hz, 1H), 6.21 (td, J = 8.4, 2.5 Hz, 1H), 6.63 (d, J = 8.2 Hz, 1H), 6.76 (d, J = 8.2 Hz, 1H), 6.86-6.90 (m, 1H), 6.90 (dd, J = 8.1, 2.4 Hz, 1H), 7.04 (d, J = 2.4 Hz, 1H), 7.27 (d, J = 8.1 Hz, 1H), 7.54-7.58 (m, 1H), 7.67-7.69 (m, 2H), 8.10 (d, J = 7.3 Hz, 1H) |

| | |
|---|---|
| 6-[4-(2-Chlorobenzoyloxy)-2-methoxyphenyl]-5-(2-methoxyphenylaminomethyl)-2,2,4-trimethyl-1,2-dihydroquioline (Compound No. 1-10) 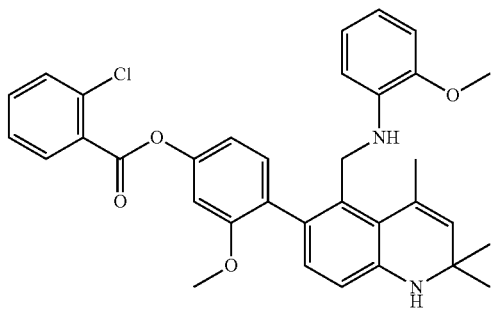 | $^1$H-NMR (400 MHZ, DMSO-$d_6$) 1.16 (s, 3H), 1.22 (s, 3H), 2.08 (s, 3H), 3.68 (s, 3H), 3.72 (s, 3H), 3.86 (dd, J = 12.1, 2.8 Hz, 1H), 4.03-4.09 (m, 1H), 4.24-4.26 (m, 1H), 5.40 (s, 1H), 6.03 (s, 1H), 6.38 (d, J = 7.5 Hz, 1H), 6.52 (t, J = 7.5 Hz, 1H), 6.62 (d, J = 8.3 Hz, 1H), 6.69 (t, J = 7.5 Hz, 1H), 6.74 (d, J = 8.3 Hz, 1H), 6.74 (d, J = 7.5 Hz, 1H), 6.88 (dd, J = 8.2, 2.3 Hz, 1H), 6.98 (d, J = 2.3 Hz, 1H), 7.18 (d, J = 8.2 Hz, 1H), 7.53-7.57 (m, 1H), 7.66-7.68 (m, 2H), 8.09 (d, J = 7.6 Hz, 1H) |
| 6-(4-Butyryloxy-2-methoxyphenyl)-5-(2-methoxyphenylaminomethyl)-2,2,4-trimethyl-1,2-dihydroquioline (Compound No. 1-11) 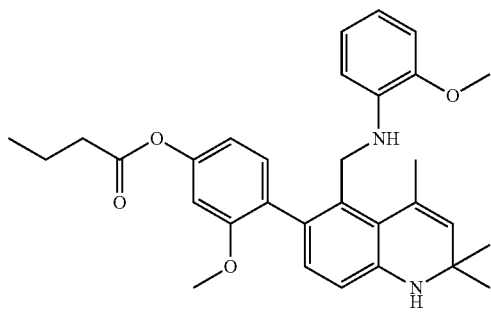 | $^1$H-NMR (400 MHz, CDCl$_3$) δ 1.04 (t, J = 7.3 Hz, 3H), 1.25 (s, 3H), 1.29 (s, 3H), 1.79 (sept, J = 7.3 Hz, 2H), 2.17 (s, 3H), 2.53 (t, J = 7.3 Hz, 2H), 3.66 (s, 3H), 3.75 (s, 3H), 3.87 (br s, 1H), 4.01 (d, J = 12.3 Hz, 1H), 4.14 (d, J = 12.3 Hz, 1H), 4.34 (br s, 1H), 5.46 (s, 1H), 6.38 (dd, J = 7.8, 1.5 Hz, 1H), 6.55-6.59 (m, 1H), 6.56 (d, J = 8.1 Hz, 1H), 6.59 (d, J = 2.2 Hz, 1H), 6.67 (dd, J = 8.1, 2.2 Hz, 1H), 6.69 (dd, J = 7.8, 1.5 Hz, 1H), 6.77 (td, J = 7.8, 1.5 Hz, 1H), 6.85 (d, J = 8.1 Hz, 1H), 7.14 (d, J = 8.1 Hz, 1H) |
| 6-[4-(2-Fluorobenzoyloxy)-2-methoxyphenyl]-5-(2-methoxyphenylaminomethyl)-2,2,4-trimethyl-1,2-dihydroquioline (Compound No. 1-12) 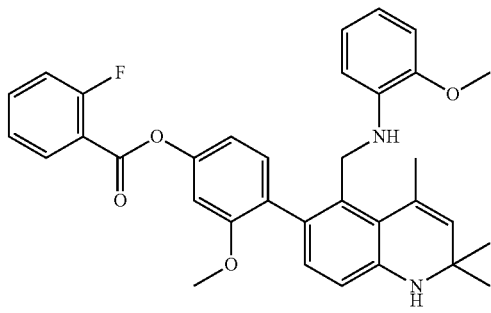 | $^1$H-NMR (400 MHz, DMSO-$d_6$) δ 1.16 (s, 3H), 1.22 (s, 3H), 2.08 (s, 3H), 3.67 (s, 3H), 3.72 (s, 3H), 3.86 (dd, J = 12.7, 3.3 Hz, 1H), 4.07 (dd, J = 12.7, 6.5 Hz, 1H), 4.25 (dd, J = 6.5, 3.3 Hz, 1H), 5.40 (s, 1H), 6.03 (s, 1H), 6.38 (dd, J = 7.6, 1.2 Hz, 1H), 6.52 (td, J = 7.6, 1.2 Hz, 1H), 6.62 (d, J = 8.2 Hz, 1H), 6.69 (td, J = 7.6, 1.2 Hz, 1H), 6.74 (d, J = 8.2 Hz, 1H), 6.74 (dd, J = 7.6, 1.2 Hz, 1H), 6.86 (dd, J = 8.1, 2.3 Hz, 1H), 6.97 (d, J = 2.3 Hz, 1H), 7.16 (d, J = 8.1 Hz, 1H), 7.39-7.46 (m, 2H), 7.75-7.80 (m, 1H), 8.10 (td, J = 7.7, 1.8 Hz, 1H) |

| | |
|---|---|
| 5-(2-Methoxyphenylaminomethyl)-6-[2-methoxy-4-(pyridin-4-ylcarbonyloxy)phenyl]-2,2,4-trimethyl-1,2-dihydroquioline (Compound No. 1-13)<br>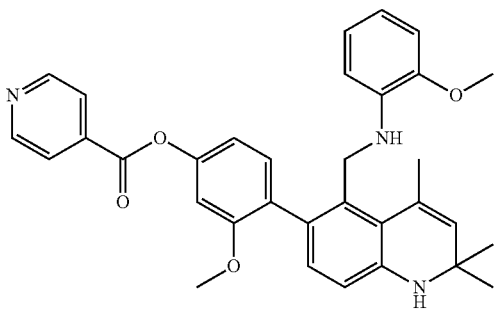 | $^1$H-NMR (400 MHz, DMSO-d$_6$) δ 1.16 (s, 3H), 1.22 (s, 3H), 2.08 (s, 3H), 3.67 (s, 3H), 3.72 (s, 3H), 3.85 (dd, J = 12.3, 3.5 Hz, 1H), 4.07 (dd, J = 12.3, 7.0 Hz, 1H), 4.25 (dd, J = 7.0, 3.5 Hz, 1H), 5.40 (s, 1H), 6.03 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.74 (d, J = 8.2 Hz, 1H), 6.74 (dd, J = 7.8, 1.3 Hz, 1H), 6.90 (dd, J = 8.1, 2.2 Hz, 1H), 7.02 (d, J = 2.2 Hz, 1H), 7.18 (d, J = 8.1 Hz, 1H), 8.00 (d, J = 6.1 Hz, 2H), 8.88 (d, J = 6.1 Hz, 2H) |
| 6-(4-Isopropylcarbonyloxy-2-methoxyphenyl)-5-(2-methoxyphenylaminomethyl)-2,2,4-trimethyl-1,2-dihydroquioline (Compound No. 1-14)<br>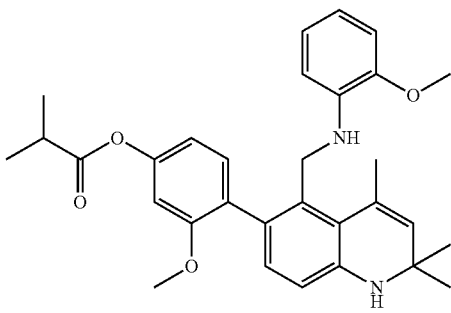 | $^1$H-NMR (400 MHz, DMSO-d$_6$) δ 1.15 (s, 3H), 1.21 (s, 3H), 1.22 (d, J = 6.8 Hz, 6H), 2.06 (s, 3H), 2.78 (hept, J = 6.8 Hz, 1H), 3.65 (s, 3H), 3.71 (s, 3H), 3.82 (dd, J = 12.4, 3.2 Hz, 1H), 4.04 (dd, J = 12.4, 6.7 Hz, 1H), 4.23 (dd, J = 6.7, 3.2 Hz, 1H), 5.39 (s, 1H), 6.01 (s, 1H), 6.35 (dd, J = 7.8, 1.6 Hz, 1H), 6.51 (td, J = 7.8, 1.6 Hz 1H), 6.60 (d, J = 8.3 Hz, 1H), 6.67 (dd, J = 8.1, 2.1 Hz, 1H), 6.68-6.72 (m, 1H), 6.71 (d, J = 8.3 Hz, 1H), 6.74 (dd, J = 7.8, 1.6 Hz, 1H), 6.75 (d, J = 2.1 Hz, 1H), 7.10 (d, J = 8.1 Hz, 1H) |
| 5-(2-Methoxyphenylaminomethyl)-6-[2-methoxy-4-(thiophen-2-ylcarbonyloxy)phenyl]-2,2,4-trimethyl-1,2-dihydroquioline (Compound No. 1-15)<br>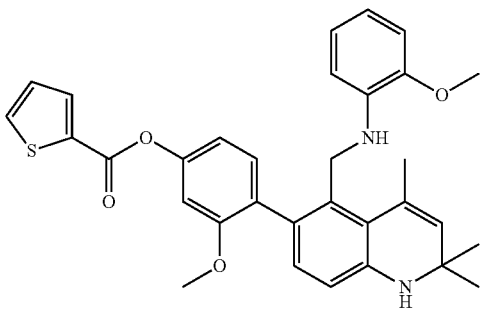 | 1H-NMR (400 MHz, DMSO-d$_6$) δ 1.16 (s, 3H), 1.22 (s, 3H), 2.08 (s, 3H), 3.67 (s, 3H), 3.72 (s, 3H), 3.85 (dd, J = 12.2, 3.5 Hz, 1H), 4.04-4.08 (m, 1H), 4.24 (dd, J = 6.6, 3.5 Hz, 1H), 5.40 (s, 1H), 6.03 (s, 1H), 6.37 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.73 (d, J = 8.2 Hz, 1H), 6.74 (dd, J = 7.8, 1.3 Hz, 1H), 6.84 (dd, J = 8.1, 2.3 Hz, 1H), 6.94 (d, J = 2.3 Hz, 1H), 7.15 (d, J = 8.1 Hz, 1H), 7.31 (dd, J = 5.0, 3.7 Hz, 1H), 8.01 (dd, J = 3.7, 1.3 Hz, 1H), 8.09 (dd, J = 5.0, 1.3 Hz, 1H) |

| | |
|---|---|
| 5-(5-Fluoro-2-methylphenyl aminomethyl)-6-[2-methoxy-4-(pyridin-3-ylcarbonyloxy) phenyl]-2,2,4-trimethyl-1,2-dihydroquioline (Compound No. 1-16)<br>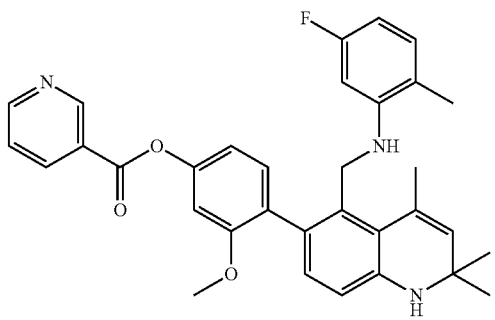 | $^1$H-NMR (500 MHz, DMSO-$d_6$) δ 1.12 (s, 3H), 1.20 (s, 3H), 1.92 (s, 3H), 2.05 (s, 3H), 3.72 (s, 3H), 3.95 (dd, J = 13.1, 4.6 Hz, 1H), 4.10 (dd, J = 13.1, 4.6 Hz, 1H), 4.24 (t, J = 4.6 Hz, 1H), 5.41 (s, 1H), 6.03 (s, 1H), 6.08 (dd, J = 12.4, 2.5 Hz, 1H), 6.21 (td, J = 8.4, 2.5 Hz, 1H), 6.63 (d, J = 8.2 Hz, 1H), 6.77 (d, J = 8.2 Hz, 1H), 6.87-6.90 (m, 1H), 6.92 (dd, J = 8.1, 2.3 Hz, 1H), 7.08 (d, J = 2.3 Hz, 1H), 7.27 (d, J = 8.1 Hz, 1H), 7.66 (ddd, J = 8.0, 4.9, 0.9 Hz, 1H), 8.47 (dt, J = 8.0, 2.0 Hz, 1H), 8.90 (dd, J = 4.9, 2.0 Hz, 1H), 9.27 (dd, J = 2.0, 0.9 Hz, 1H) |
| 5-(5-Fluoro-2-methylphenyl aminomethyl)-6-[4-(furan-2-ylcarbonyloxy)-2-methoxyphenyl]-2,2,4-trimethyl-1,2-dihydroquioline (Compound No. 1-17)<br>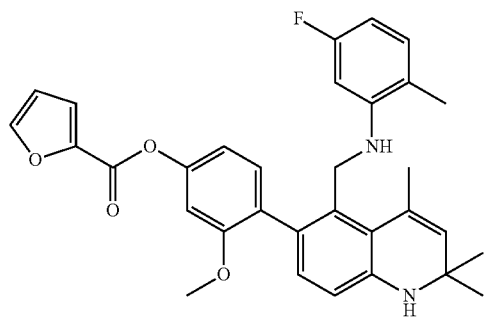 | $^1$H-NMR (400 MHz, DMSO-$d_6$) δ 1.11 (s, 3H), 1.20 (s, 3H), 1.90 (s, 3H), 2.05 (s, 3H), 3.71 (s, 3H), 3.93 (dd, J = 13.1, 4.2 Hz, 1H), 4.09 (dd, J = 13.1, 4.2 Hz, 1H), 4.24 (t, J = 4.2 Hz, 1H), 5.41 (s, 1H), 6.04 (s, 1H), 6.06 (dd, J = 12.7, 2.6 Hz, 1H), 6.21 (td, J = 8.5, 2.6 Hz, 1H), 6.62 (d, J = 8.2 Hz, 1H), 6.75 (d, J = 8.2 Hz, 1H), 6.80 (dd, J = 3.6, 1.7 Hz, 1H), 6.84-6.90 (m, 2H), 6.99 (d, J = 2.2 Hz, 1H), 7.24 (d, J = 8.3 Hz, 1H), 7.57 (dd, J = 3.6, 0.8 Hz, 1H), 8.11 (dd, J = 1.7, 0.8 Hz, 1H) |
| 6-[2-Methoxy-4-(3-methoxycarbonylbenzoyloxy) phenyl]-5-(2-methoxyphenylaminomethyl)-2,2,4-trimethyl-1,2-dihydroquioline (Compound No. 1-18)<br>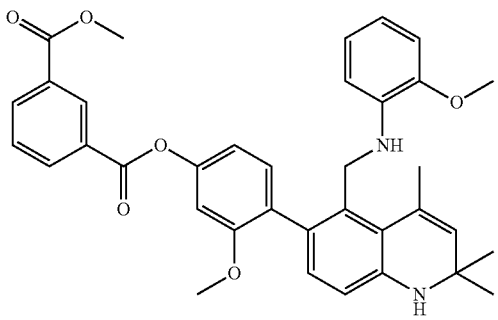 | $^1$H-NMR (500 MHz, DMSO-$d_6$) δ 1.16 (s, 3H), 1.22 (s, 3H), 2.08 (s, 3H), 3.67 (s, 3H), 3.72 (s, 3H), 3.87 (dd, J = 12.4, 3.3 Hz, 1H), 3.91 (s, 3H), 4.07 (dd, J = 12.4, 6.6 Hz, 1H), 4.26 (dd, J = 6.6, 3.3 Hz, 1H) 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.70 (td, J = 7.8, 1.3 Hz, 1H), 6.75 (d, J = 8.2 Hz, 1H), 6.75 (dd, J = 7.8, 1.3 Hz, 1H), 6.89 (dd, J = 8.1, 2.3 Hz, 1H), 7.01 (d, J = 2.3 Hz, 1H), 7.17 (d, J = 8.1 Hz, 1H), 7.78 (t, J = 7.8 Hz, 1H), 8.30 (dt, J = 7.8, 1.5 Hz, 1H), 8.38 (dt, J = 7.8, 1.5 Hz, 1H), 8.64 (t, J = 1.5 Hz, 1H) |

| | |
|---|---|
| 6-[2-Methoxy-4-(3-methylbenzoyloxy) phenyl]-5-(2-methoxyphenylaminomethyl)-2,2,4-trimethyl-1,2-dihydroquioline (Compound No. 1-19)<br/>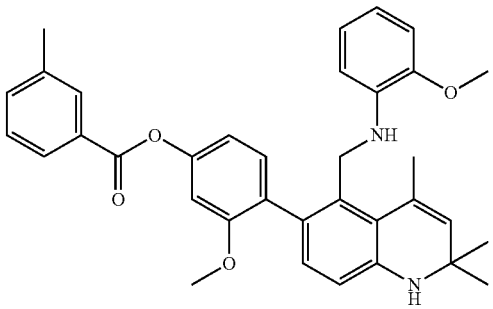 | $^1$H-NMR (400 MHz, DMSO-d$_6$) δ 1.16 (s, 3H), 1.22 (s, 3H), 2.08 (s, 3H), 2.41 (s, 3H), 3.67 (s, 3H), 3.72 (s, 3H), 3.85 (dd, J = 12.7, 3.4 Hz, 1H), 4.07 (dd, J = 12.7, 6.8 Hz, 1H), 4.25 (dd, J = 6.8, 3.4 Hz, 1H), 5.40 (s, 1H), 6.02 (s, 1H), 6.38 (dd, J = 7.8, 1.4 Hz, 1H), 6.52 (td, J = 7.8, 1.4 Hz, 1H), 6.62 (d, J = 8.2 Hz, 1H), 6.69 (td, J = 7.8, 1.4 Hz, 1H), 6.74 (d, J = 8.2 Hz, 1H), 6.75 (dd, J = 7.8, 1.4 Hz, 1H), 6.84 (dd, J = 8.1, 2.4 Hz, 1H), 6.95 (d, J = 2.4 Hz, 1H), 7.16 (d, J = 8.1 Hz, 1H), 7.49 (t, J = 7.7 Hz, 1H), 7.56 (d, J = 7.7 Hz, 1H), 7.92 (d, J = 7.7 Hz, 1H), 7.95 (s, 1H) |
| 6-[2-Methoxy-4-(4-methylbenzoyloxy) phenyl]-5-(2-methoxyphenylaminomethyl)-2,2,4-trimethyl-1,2-dihydroquioline (Compound No. 1-20)<br/>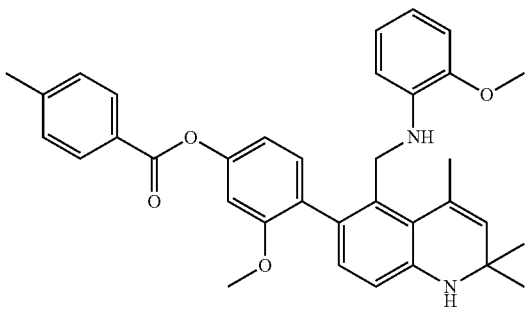 | $^1$H-NMR (500 MHz, DMSO-d$_6$) δ 1.16 (s, 3H), 1.22 (s, 3H), 2.08 (s, 3H), 2.42 (s, 3H), 3.67 (s, 3H), 3.72 (s, 3H), 3.86 (dd, J = 12.2, 3.5 Hz, 1H), 4.07 (dd, J = 12.2, 6.3 Hz, 1H), 4.25 (dd, J = 6.3, 3.5 Hz, 1H), 5.40 (s, 1H), 6.01 (s, 1H), 6.38 (dd, J = 7.7, 1.3 Hz, 1H), 6.52 (td, J = 7.7, 1.3 Hz, 1H), 6.62 (d, J = 8.1 Hz, 1H), 6.69 (td, J = 7.7, 1.3 Hz, 1H), 6.74 (d, J = 8.1 Hz, 1H), 6.74 (dd, J = 7.7, 1.3 Hz, 1H), 6.84 (dd, J = 8.2, 2.2 Hz, 1H), 6.94 (d, J = 2.2 Hz, 1H), 7.15 (d, J = 8.2 Hz, 1H), 7.41 (d, J = 8.4 Hz, 2H), 8.02 (d, J = 8.4 Hz, 2H) |
| 6-[4-(3-Chlorobenzoyloxy)-2-methoxyphenyl]-5-(2-methoxyphenylaminomethyl)-2,2,4-trimethyl-1,2-dihydroquioline (Compound No. 1-21)<br/>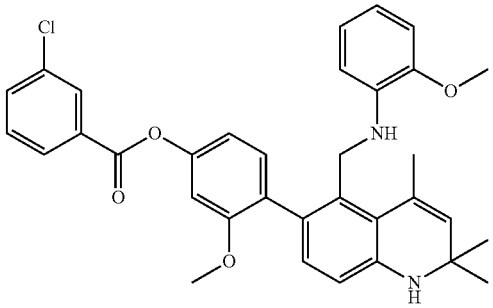 | $^1$H-NMR (400 MHz, DMSO-d$_6$) δ 1.16 (s, 3H), 1.22 (s, 3H), 2.08 (s, 3H), 3.67 (s, 3H), 3.72 (s, 3H), 3.85 (dd, J = 12.3, 3.3 Hz, 1H), 4.07 (dd, J = 12.3, 6.5 Hz, 1H), 4.25 (dd, J = 6.5, 3.3 Hz, 1H), 5.40 (s, 1H), 6.02 (s, 1H), 6.38 (dd, J = 7.7, 1.3 Hz, 1H), 6.52 (td, J = 7.7, 1.3 Hz, 1H), 6.62 (d, J = 8.2 Hz, 1H), 6.69 (td, J = 7.7, 1.3 Hz, 1H), 6.74 (d, J = 8.2 Hz, 1H), 6.75 (dd, J = 7.7, 1.3 Hz, 1H), 6.88 (dd, J = 8.3, 2.2 Hz, 1H), 7.00 (d, J = 2.2 Hz, 1H), 7.17 (d, J = 8.3 Hz, 1H), 7.65 (t, J = 8.0 Hz, 1H), 7.83 (ddd, J = 8.0, 2.2, 1.1 Hz, 1H), 8.07-8.09 (m, 1H), 8.10-8.11 (m, 1H) |

| Compound | NMR |
|---|---|
| 6-[2-Methoxy-4-(4-methoxybenzoyloxy)phenyl]-5-(2-methoxyphenylaminomethyl)-2,2,4-trimethyl-1,2-dihydroquioline (Compound No. 1-22) 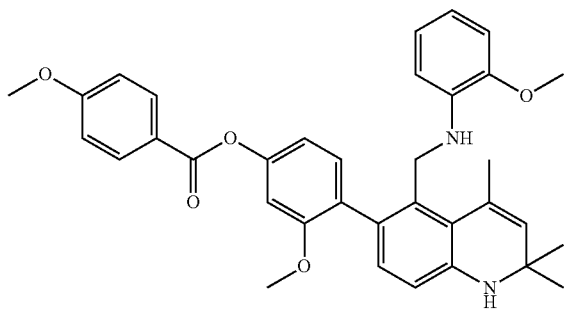 | $^1$H-NMR (500 MHz, DMSO-d$_6$) δ 1.16 (s, 3H), 1.22 (s, 3H), 2.08 (s, 3H), 3.66 (s, 3H), 3.72 (s, 3H), 3.86 (dd, J = 12.5, 3.5 Hz, 1H), 3.87 (s, 3H), 4.07 (dd, J = 12.5, 6.5 Hz, 1H), 4.25 (dd, J = 6.5, 3.5 Hz, 1H), 5.40 (s, 1H), 6.01 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.74 (d, J = 8.2 Hz, 1H), 6.74 (dd, J = 7.8, 1.3 Hz, 1H), 6.82 (dd, J = 8.2, 2.4 Hz, 1H), 6.92 (d, J = 2.4 Hz, 1H), 7.12 (d, J = 9.0 Hz, 2H), 7.14 (d, J = 8.2 Hz, 1H), 8.08 (d, J = 9.0 Hz, 2H) |
| 6-[4-(4-Fluorobenzoyloxy)-2-methoxyphenyl]-5-(2-methoxyphenylaminomethyl)-2,2,4-trimethyl-1,2-dihydroquioline (Compound No. 1-23) 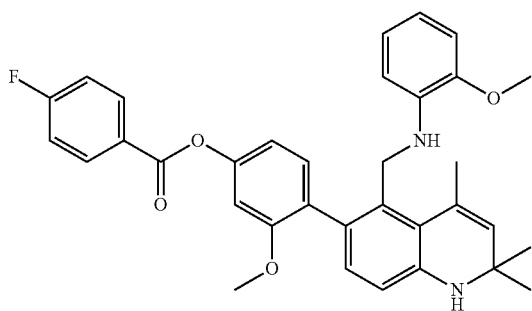 | $^1$H-NMR (500 MHz, DMSO-d$_6$) δ 1.16 (s, 3H), 1.22 (s, 3H), 2.08 (s, 3H), 3.67 (s, 3H), 3.72 (s, 3H), 3.86 (dd, J = 12.2, 3.1 Hz, 1H), 4.07 (dd, J = 12.2, 6.6 Hz, 1H), 4.25 (dd, J = 6.6, 3.1 Hz, 1H), 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.74 (d, J = 8.2 Hz, 1H), 6.74 (dd, J = 7.8, 1.3 Hz, 1H), 6.85 (dd, J = 8.0, 2.4 Hz, 1H), 6.97 (d, J = 2.4 Hz, 1H), 7.16 (d, J = 8.0 Hz, 1H), 7.41-7.47 (m, 2H), 8.18-8.23 (m, 2H) |
| 6-[4-(4-Chlorobenzoyloxy)-2-methoxyphenyl]-5-(2-methoxyphenylaminomethyl)-2,2,4-trimethyl-1,2-dihydroquioline (Compound No. 1-24) 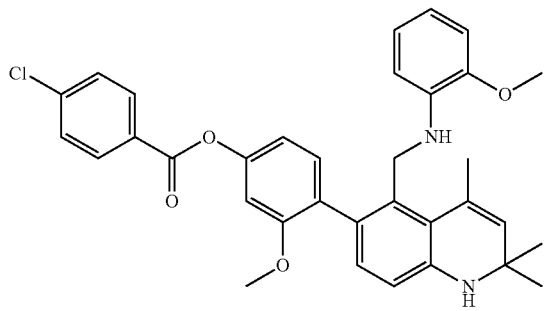 | $^1$H-NMR (400 MHz, DMSO-d$_6$) δ 1.16 (s, 3H), 1.22 (s, 3H), 2.08 (s, 3H), 3.67 (s, 3H), 3.72 (s, 3H), 3.85 (dd, J = 12.2, 3.4 Hz, 1H), 4.07 (dd, J = 12.2, 6.7 Hz, 1H), 4.25 (dd, J = 6.7, 3.4 Hz, 1H), 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.2 Hz, 1H), 6.69 (td, J = 7.8, 1.3 Hz, 1H), 6.74 (d, J = 8.2 Hz, 1H), 6.74 (dd, J = 7.8, 1.3 Hz, 1H), 6.86 (dd, J = 8.1, 2.2 Hz, 1H), 6.98 (d, J = 2.2 Hz, 1H), 7.16 (d, J = 8.1 Hz, 1H), 7.68 (d, J = 8.8 Hz, 2H), 8.13 (d, J = 8.8 Hz, 2H) |

| | |
|---|---|
| 6-[2-Methoxy-4-(2-nitrobenzoyloxy)phenyl]-5-(2-methoxyphenylaminomethyl)-2,2,4-trimethyl-1,2-dihydroquioline (Compound No. 1-25) 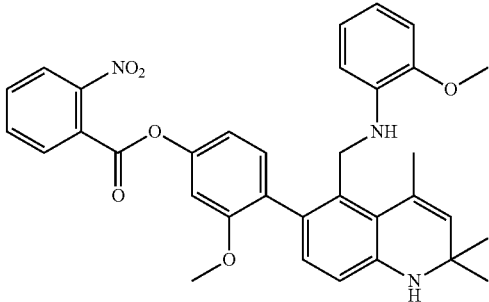 | $^1$H-NMR (400 MHz, DMSO-d$_6$) δ 1.16 (s, 3H), 1.22 (s, 3H), 2.08 (s, 3H), 3.68 (s, 3H), 3.72 (s, 3H), 3.85 (dd, J = 12.3, 3.0 Hz, 1H), 4.06 (dd, J = 12.3, 6.7 Hz, 1H), 4.24 (dd, J = 6.7, 3.0 Hz, 1H), 5.40 (s, 1H), 6.04 (s, 1H), 6.37 (dd, J = 7.8, 1.3 Hz, 1H), 6.51 (td, J = 7.8, 1.3 Hz, 1H), 6.62 (d, J = 8.2 Hz, 1H), 6.68 (td, J = 7.8, 1.3 Hz, 1H), 6.73 (d, J = 8.2 Hz, 1H), 6.74 (dd, J = 7.8, 1.3 Hz, 1H), 6.85 (dd, J = 8.1, 2.2 Hz, 1H), 6.94 (d, J = 2.2 Hz, 1H), 7.20 (d, J = 8.1 Hz, 1H), 7.90 (td, J = 7.6, 1.6 Hz, 1H), 7.95 (td, J = 7.6, 1.6 Hz, 1H), 8.10 (dd, J = 7.6, 1.6 Hz, 1H), 8.18 (dd, J = 7.6, 1.6 Hz, 1H) |
| 6-[2-Methoxy-4-(2-methylthiobenzoyloxy)phenyl]-5-(2-methoxyphenylaminomethyl)-2,2,4-trimethyl-1,2-dihydroquioline (Compound No. 1-26) 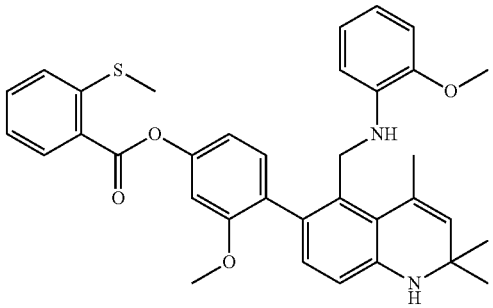 | $^1$H-NMR 400 MHz, DMSO-d$_6$) δ 1.16 (s, 3H), 1.22 (s, 3H), 2.08 (s, 3H), 2.46 (s, 3H), 3.67 (s, 3H), 3.72 (s, 3H), 3.86 (dd, J = 13.0, 3.4 Hz, 1H), 4.07 (dd, J = 13.0, 6.9 Hz, 1H), 4.25 (dd, J = 6.9, 3.4 Hz, 1H), 5.40 (s, 1H), 6.03 (s, 1H), 6.38 (dd, J = 7.8, 1.3 Hz, 1H), 6.52 (td, J = 7.8, 1.3 Hz, 1H), 6.62 (d, J = 8.1 Hz, 1H), 6.69 (td, J = 7.8, 1.3 Hz, 1H), 6.74 (d, J = 8.1 Hz, 1H), 6.74 (dd, J = 7.8, 1.3 Hz, 1H), 6.83 (dd, J = 8.2, 2.2 Hz, 1H), 6.94 (d, J = 2.2 Hz, 1H), 7.16 (d, J = 8.2 Hz, 1H), 7.31 (td, J = 7.8, 1.5 Hz, 1H), 7.46 (dd, J = 7.8, 1.5 Hz, 1H), 7.66 (td, J = 7.8, 1.5 Hz, 1H), 8.17 (dd, J = 7.8, 1.5 Hz, 1H) |
| 6-[4-(3-Acetylbenzoyloxy)-2-methoxyphenyl]-5-(2-methoxyphenylaminomethyl)-2,2,4-trimethyl-1,2-dihydroquioline (Compound No. 1-27) 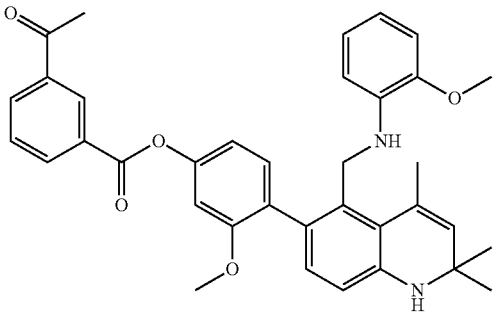 | $^1$H-NMR (500 MHz, DMSO-d$_6$) δ 1.16 (s, 3H), 1.22 (s, 3H), 2.08 (s, 3H), 2.67 (s, 3H), 3.67 (s, 3H), 3.72 (s, 3H), 3.86 (dd, J = 12.3, 3.1 Hz, 1H), 4.08 (dd, J = 12.3, 6.7 Hz, 1H), 4.26 (dd, J = 6.7, 3.1 Hz, 1H), 5.40 (s, 1H), 6.02 (s, 1H), 6.38 (dd, J = 7.8, 1.3 Hz, 1H), 6.52 (td, J = 7.8, 1.3 Hz, 1H), 6.62 (d, J = 8.1 Hz, 1H), 6.70 (td, J = 7.8, 1.3 Hz, 1H), 6.75 (d, J = 8.1 Hz, 2H), 6.89 (dd, J = 8.2, 2.3 Hz, 1H), 7.00 (d, J = 2.3 Hz, 1H), 7.18 (d, J = 8.2 Hz, 1H), 7.77 (t, J = 7.8 Hz, 1H), 8.31 (dt, J = 7.8, 1.5 Hz, 1H), 8.36 (dt, J = 7.8, 1.5 Hz, 1H), 8.61 (t, J = 1.5 Hz, 1H) |

| Compound | NMR |
|---|---|
| 6-[4-(3-Chlorothiophen-2-yl carbonyloxy)-2-methoxyphenyl]-5-(2-methoxyphenylaminomethyl)-2,2,4-trimethyl-1,2-dihydroquioline (Compound No. 1-28) 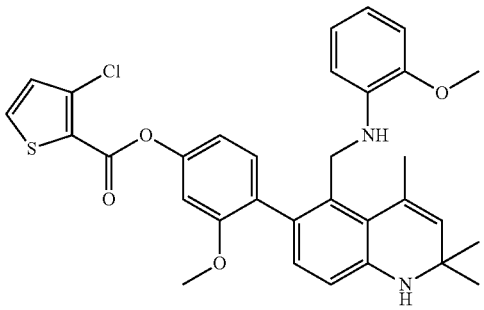 | $^1$H-NMR (400 MHz, DMSO-d$_6$) δ 1.16 (s, 3H, 1.22 (s, 3H), 2.08 (s, 3H), 3.67 (s, 3H), 3.72 (s, 3H), 3.86 (dd, J = 12.2, 3.4 Hz, 1H), 4.06 (dd, J = 12.2, 6.6 Hz, 1H), 4.24 (dd, J = 6.6, 3.4 Hz, 1H), 5.40 (s, 1H), 6.03 (s, 1H), 6.37 (dd, J = 7.8, 1.4 Hz, 1H), 6.52 (td, J = 7.8, 1.4 Hz, 1H), 6.62 (d, J = 8.3 Hz, 1H), 6.69 (td, J = 7.8, 1.4 Hz, 1H), 6.73 (d, J = 8.3 Hz, 1H), 6.75 (dd, J = 7.8, 1.4 Hz, 1H), 6.84 (dd, J = 8.3, 2.2 Hz, 1H), 6.96 (d, J = 2.2 Hz, 1H), 7.15 (d, J = 8.3 Hz, 1H), 7.35 (d, J = 5.2 Hz, 1H), 8.14 (d, J = 5.2 Hz, 1H) |
| 6-[2-Methoxy-4-(3-methylfuran-2-ylcarbonyloxy)phenyl]-5-(2-methoxyphenylaminomethyl)-2,2,4-trimethyl-1,2-dihydroquioline (Compound No. 1-29) 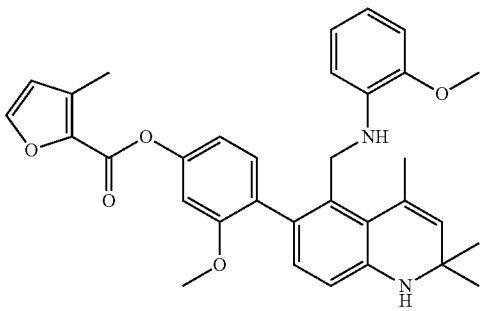 | $^1$H-NMR (500 MHz, DMSO-d$_6$) δ 1.15 (s, 3H), 1.22 (s, 3H), 2.07 (s, 3H), 2.36 (s, 3H), 3.66 (s, 3H), 3.72 (s, 3H), 3.87 (dd, J = 12.4, 3.5 Hz, 1H), 4.06 (dd, J = 12.4, 6.9 Hz, 1H), 4.24 (dd, J = 6.9, 3.5 Hz, 1H), 5.39 (s, 1H), 6.01 (s, 1H), 6.37 (dd, J = 7.7, 1.4 Hz, 1H), 6.51 (td, J = 7.7, 1.4 Hz, 1H), 6.61 (d, J = 7.9 Hz, 1H), 6.69 (d, J = 1.4 Hz, 1H), 6.69 (td, J = 7.7, 1.4 Hz, 1H), 6.73 (d, J = 7.9 Hz, 1H), 6.74 (dd, J = 7.7, 1.4 Hz, 1H), 6.81 (dd, J = 8.0, 2.2 Hz, 1H), 6.92 (d, J = 2.2 Hz, 1H), 7.14 (d, J = 8.0 Hz, 1H), 7.94 (d, J = 1.4 Hz, 1H) |
| 5-(2-Methoxyphenylaminomethyl)-6-[2-methoxy-4-(thiazol-4-ylcarbonyloxy)phenyl]-2,2,4-trimethyl-1,2-dihydroquioline (Compound No. 1-30) 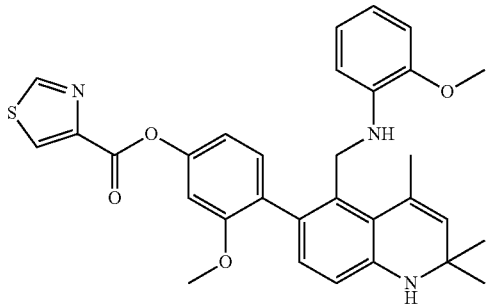 | $^1$H-NMR (400 MHz, DMSO-d$_6$) δ 1.16 (s, 3H, 1.22 (s, 3H), 2.08 (s, 3H), 3.67 (s, 3H), 3.72 (s, 3H), 3.86 (dd, J = 11.8, 3.5 Hz, 1H), 4.07 (dd, J = 11.8, 6.8 Hz, 1H), 4.24 (dd, J = 6.8, 3.5 Hz, 1H), 5.40 (s, 1H), 6.02 (s, 1H), 6.37 (dd, J = 7.8, 1.3 Hz, 1H), 6.52 (td, J = 7.8, 1.3 Hz, 1H), 6.62 (d, J = 8.1 Hz, 1H), 6.69 (td, J = 7.8, 1.3 Hz, 1H), 6.74 (d, J = 8.1 Hz, 2H), 6.85 (dd, J = 8.2, 2.2 Hz, 1H), 6.95 (d, J = 2.2 Hz, 1H), 7.16 (d, J = 8.2 Hz, 1H), 8.86 (d, J = 2.0 Hz, 1H), 9.27 (d, J = 2.0 Hz, 1H) |

| | |
|---|---|
| 6-[2-Methoxy-4-(6-methylpyridin-3-ylcarbonyloxy)phenyl]-5-(2-methoxyphenylaminomethyl)-2,2,4-trimethyl-1,2-dihydroquioline (Compound No. 1-31)<br />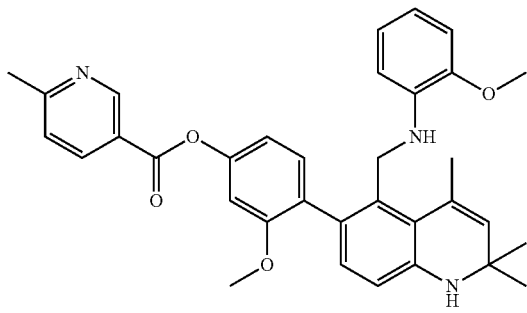 | $^1$H-NMR (500 MHz, DMSO-d$_6$) δ 1.16 (s, 3H), 1.22 (s, 3H), 2.08 (s, 3H), 2.60 (s, 3H), 3.67 (s, 3H), 3.72 (s, 3H), 3.85 (dd, J = 12.1, 3.4 Hz, 1H), 4.07 (dd, J = 12.1, 6.4 Hz, 1H), 4.25 (dd, J = 6.4, 3.4 Hz, 1H), 5.40 (s, 1H), 6.02 (s, 1H), 6.37 (dd, J = 7.8, 1.3 Hz, 1H), 6.52 (td, J = 7.8, 1.3 Hz, 1H), 6.62 (d, J = 8.1 Hz, 1H), 6.69 (td, J = 7.8, 1.3 Hz, 1H), 6.74 (d, J = 8.1 Hz, 1H), 6.74 (dd, J = 7.8, 1.3 Hz, 1H), 6.87 (dd, J = 8.1, 2.3 Hz, 1H), 6.99 (d, J = 2.3 Hz, 1H), 7.16 (d, J = 8.1 Hz, 1H), 7.50 (d, J = 8.2 Hz, 1H), 8.33 (dd, J = 8.2, 2.4 Hz, 1H), 9.12 (d, J = 2.4 Hz, 1H) |
| 6-[2-Methoxy-4-(2-methoxypyridin-3-ylcarbonyloxy)phenyl]-5-(2-methoxyphenylaminomethyl)-2,2,4-trimethyl-1,2-dihydroquioline (Compound No. 1-32)<br />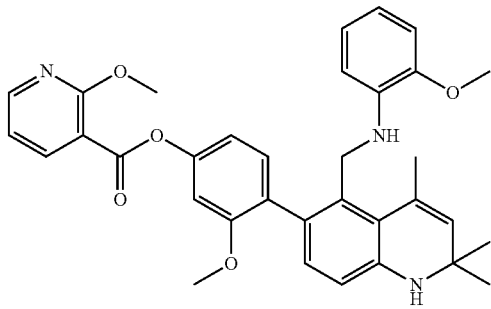 | $^1$H-NMR (400 MHz, DMSO-d$_6$) δ 1.16 (s, 3H), 1.22 (s, 3H), 2.08 (s, 3H), 3.67 (s, 3H), 3.72 (s, 3H), 3.85 (dd, J = 12.7, 3.1 Hz, 1H), 3.97 (s, 3H), 4.07 (dd, J = 12.7, 6.8 Hz, 1H), 4.25 (dd, J = 6.8, 3.1 Hz, 1H), 5.40 (s, 1H), 6.02 (s, 1H), 6.37 (dd, J = 7.7, 1.3 Hz, 1H), 6.52 (td, J = 7.7, 1.3 Hz, 1H), 6.62 (d, J = 8.2 Hz, 1H), 6.69 (td, J = 7.7, 1.3 Hz, 1H), 6.73 (d, J = 8.2 Hz, 1H), 6.74 (dd, J = 7.7, 1.3 Hz, 1H), 6.82 (dd, J = 8.1, 2.2 Hz, 1H), 6.93 (d, J = 2.2 Hz, 1H), 7.15 (d, J = 8.1 Hz, 1H), 7.19 (dd, J = 7.5, 4.9 Hz, 1H), 8.39 (dd, J = 7.5, 2.1 Hz, 1H), 8.47 (dd, J = 4.9, 2.1 Hz, 1H) |
| 5-(5-Fluoro-2-methylphenylaminomethyl)-6-[4-(furan-3-ylcarbonyloxy)-2-methoxyphenyl]-2,2,4-trimethyl-1,2-dihydroquioline (Compound No. 1-33)<br />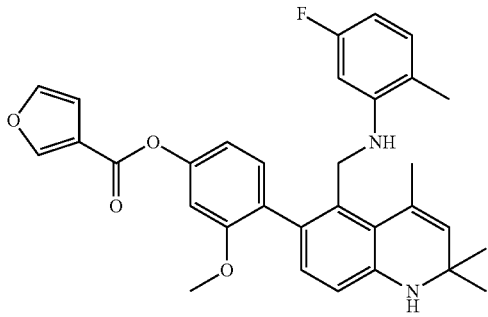 | $^1$H-NMR (400 MHz, DMSO-d$_6$) δ 1.11 (s, 3H), 1.20 (s, 3H), 1.90 (s, 3H), 2.05 (s, 3H), 3.71 (s, 3H), 3.93 (dd, J = 13.2, 4.6 Hz, 1H), 4.08 (dd, J = 13.2, 4.6 Hz, 1H), 4.20-4.25 (m, 1H), 5.41 (s, 1H), 6.03 (s, 1H), 6.06 (dd, J = 12.2, 2.5 Hz, 1H), 6.21 (td, J = 8.4, 2.5 Hz, 1H), 6.62 (d, J = 8.2 Hz, 1H), 6.75 (d, J = 8.2 Hz, 1H), 6.83 (dd, J = 8.1, 2.2 Hz, 1H), 6.86-6.90 (m, 1H), 6.94 (dd, J = 1.7, 0.9 Hz, 1H), 6.96 (d, J = 2.2 Hz, 1H), 7.23 (d, J = 8.1 Hz, 1H), 7.91 (t, J = 1.7 Hz, 1H), 8.63 (dd, J = 1.7, 0.9 Hz, 1H) |

| | |
|---|---|
| 5-(5-Fluoro-2-methylphenylaminomethyl)-6-[2-methoxy-4-(pyridin-4-ylcarbonyloxy)phenyl]-2,2,4-trimethyl-1,2-dihydroquioline (Compound No. 1-34) 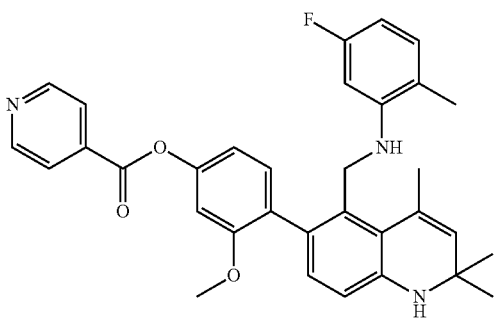 | $^1$H-NMR (400 MHz, DMSO-d$_6$) δ 1.12 (s, 3H), 1.20 (s, 3H), 1.91 (s, 3H), 2.05 (s, 3H), 3.72 (s, 3H), 3.94 (dd, J = 13.1, 4.9 Hz, 1H), 4.10 (dd, J = 13.1, 4.2 Hz, 1H), 4.23-4.26 (m, 1H), 5.41 (s, 1H), 6.04 (s, 1H), 6.07 (dd, J = 12.2, 2.4 Hz, 1H), 6.21 (td, J = 8.4, 2.4 Hz, 1H), 6.63 (d, J = 8.2 Hz, 1H), 6.76 (d, J = 8.2 Hz, 1H), 6.86-6.90 (m, 1H), 6.92 (dd, J = 8.3, 2.2 Hz, 1H), 7.08 (d, J = 2.2 Hz, 1H), 7.27 (d, J = 8.3 Hz, 1H), 8.01 (d, J = 6.1 Hz, 2H), 8.89 (d, J = 6.1 Hz, 2H) |
| 6-[4-(2-Fluorobenzoyloxy)-2-methoxyphenyl]-5-(5-fluoro-2-methylphenylaminomethyl)-2,2,4-trimethyl-1,2-dihydroquioline (Compound No. 1-35) 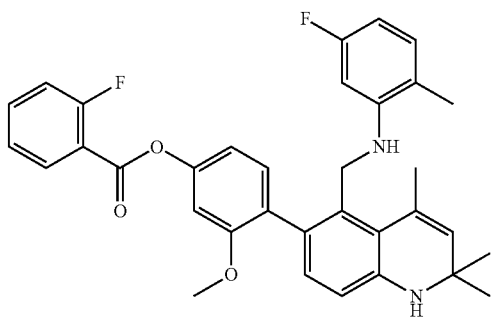 | $^1$H-NMR (400 MHz, DMSO-d$_6$) δ 1.11 (s, 3H), 1.20 (s, 3H), 1.91 (s, 3H), 2.05 (s, 3H), 3.73 (s, 3H), 3.95 (dd, J = 13.4, 4.8 Hz, 1H), 4.10 (dd, J = 13.4, 4.2 Hz, 1H), 4.22-4.27 (m, 1H), 5.41 (s, 1H), 6.03 (s, 1H), 6.07 (dd, J = 12.2, 2.6 Hz, 1H), 6.21 (td, J = 8.5, 2.6 Hz, 1H), 6.62 (d, J = 8.3 Hz, 1H), 6.76 (d, J = 8.3 Hz, 1H), 6.85-6.91 (m, 1H), 6.89 (dd, J = 8.2, 2.2 Hz, 1H), 7.03 (d, J = 2.2 Hz, 1H), 7.26 (d, J = 8.2 Hz, 1H), 7.40-7.47 (m, 2H), 7.75-7.81 (m, 1H), 8.11 (td, J = 7.8, 1.6 Hz, 1H) |
| 5-(5-Fluoro-2-methylphenylaminomethyl)-6-[2-methoxy-4-(thiophen-2-ylcarbonyloxy)phenyl]-2,2,4-trimethyl-1,2-dihydroquioline (Compound No. 1-36) 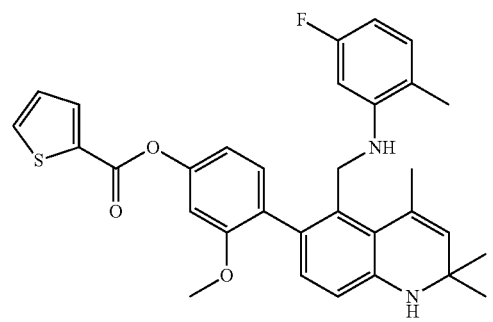 | $^1$H-NMR (400 MHz, DMSO-d$_6$) δ 1.11 (s, 3H), 1.20 (s, 3H), 1.91 (s, 3H), 2.05 (s, 3H), 3.72 (s, 3H), 3.94 (dd, J = 13.0, 5.0 Hz, 1H), 4.09 (dd, J = 13.0, 4.2 Hz, 1H), 4.22-4.26 (m, 1H), 5.41 (s, 1H), 6.03 (s, 1H), 6.07 (dd, J = 12.2, 2.5 Hz, 1H), 6.21 (td, J = 8.4, 2.5 Hz, 1H), 6.62 (d, J = 8.2 Hz, 1H), 6.76 (d, J = 8.2 Hz, 1H), 6.86-6.90 (m, 1H), 6.87 (dd, J = 8.2, 2.3 Hz, 1H), 7.00 (d, J = 2.3 Hz, 1H), 7.24 (d, J = 8.2 Hz, 1H), 7.31 (dd, J = 5.0, 3.7 Hz, 1H), 8.02 (dd, J = 3.7, 1.3 Hz, 1H), 8.10 (dd, J = 5.0, 1.3 Hz, 1H) |

| | |
|---|---|
| 6-[4-(4-Fluorobenzoyloxy)-2-methoxyphenyl]-5-(5-fluoro-2-methylphenylaminomethyl)-2,2,4-trimethyl-1,2-dihydroquioline (Compound No. 1-37) 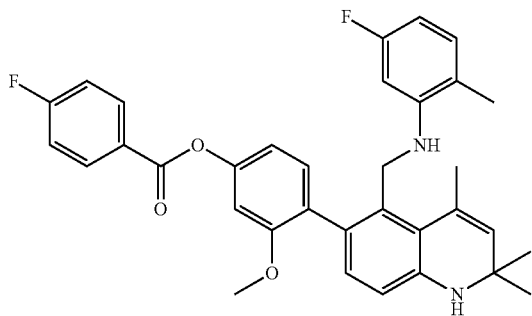 | $^1$H-NMR (400 MHz, DMSO-d$_6$) δ 1.11 (s, 3H), 1.20 (s, 3H), 1.91 (s, 3H), 2.05 (s, 3H), 3.72 (s, 3H), 3.94 (dd, J = 12.9, 5.0 Hz, 1H), 4.10 (dd, J = 12.9, 3.9 Hz, 1H), 4.23-4.26 (m, 1H), 5.41 (s, 1H), 6.03 (s, 1H), 6.07 (dd, J = 12.2, 2.5 Hz, 1H), 6.21 (td, J = 8.5, 2.5 Hz, 1H), 6.62 (d, J = 8.1 Hz, 1H), 6.76 (d, J = 8.1 Hz, 1H), 6.86-6.91 (m, 1H), 6.88 (dd, J = 8.3, 2.2 Hz, 1H), 7.03 (d, J = 2.2 Hz, 1H), 7.25 (d, J = 8.3 Hz, 1H), 7.45 (t, J = 9.0 Hz, 2H), 8.21 (dd, J = 9.0, 5.5 Hz, 2H) |
| 5-(5-Fluoro-2-methylphenylaminomethyl)-6-[2-methoxy-4-(2-methylpyridin-3-ylcarbonyloxy)phenyl]-2,2,4-trimethyl-1,2-dihydroquioline (Compound No. 1-38) 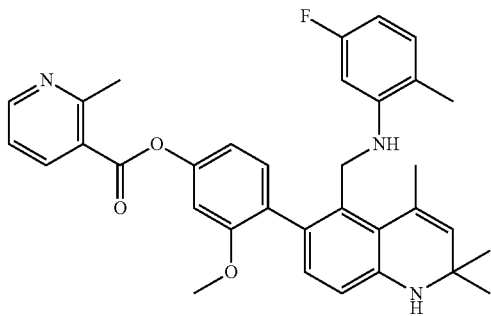 | $^1$H-NMR (500 MHz, DMSO-d$_6$) δ 1.11 (s, 3H), 1.20 (s, 3H), 1.92 (s, 3H), 2.05 (s, 3H), 2.80 (s, 3H), 3.73 (s, 3H), 3.95 (dd, J = 13.0, 5.0 Hz, 1H), 4.10 (dd, J = 13.0, 4.4 Hz, 1H), 4.24-4.26 (m, 1H), 5.41 (s, 1H), 6.03 (s, 1H), 6.07 (dd, J = 11.9, 2.5 Hz, 1H), 6.21 (td, J = 8.5, 2.5 Hz, 1H), 6.63 (d, J = 8.1 Hz, 1H), 6.76 (d, J = 8.1 Hz, 1H), 6.86-6.90 (m, 1H), 6.91 (dd, J = 8.1, 2.3 Hz, 1H), 7.06 (d, J = 2.3 Hz, 1H), 7.26 (d, J = 8.1 Hz, 1H), 7.46 (dd, J = 7.9, 5.0 Hz, 1H), 8.44 (dd, J = 7.9, 1.8 Hz, 1H), 8.71 (dd, J = 5.0, 1.8 Hz, 1H) |
| 5-(5-Fluoro-2-methylphenylaminomethyl)-6-[4-(2-methylthiobenzoyloxy)-2-methoxyphenyl]-2,2,4-trimethyl-1,2-dihydroquioline (Compound No. 1-39) 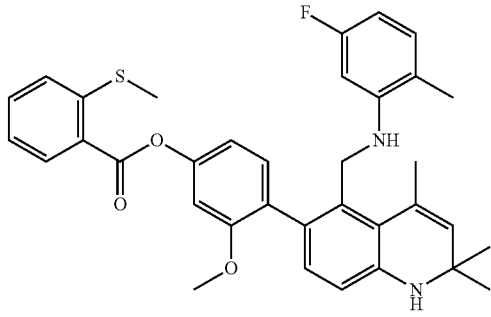 | $^1$H-NMR (400 MHz, DMSO-d$_6$) δ 1.11 (s, 3H), 1.20 (s, 3H), 1.91 (s, 3H), 2.05 (s, 3H), 2.47 (s, 3H), 3.72 (s, 3H), 3.95 (dd, J = 13.3, 4.5 Hz, 1H), 4.10 (dd, J = 13.3, 4.3 Hz, 1H), 4.23-4.26 (m, 1H), 5.41 (s, 1H), 6.03 (s, 1H), 6.08 (dd, J = 12.1, 2.5 Hz, 1H), 6.21 (td, J = 8.4, 2.5 Hz, 1H), 6.63 (d, J = 8.2 Hz, 1H), 6.76 (d, J = 8.2 Hz, 1H), 6.86 (dd, J = 8.1, 2.1 Hz, 1H), 6.86-6.90 (m, 1H), 6.99 (d, J = 2.1 Hz, 1H), 7.25 (d, J = 8.1 Hz, 1H), 7.32 (t, J = 8.0 Hz, 1H), 7.47 (d, J = 8.0 Hz, 1H), 7.67 (td, J = 8.0, 1.6 Hz, 1H), 8.18 (dd, J = 8.0, 1.6 Hz, 1H) |

| | |
|---|---|
| 5-(5-Fluoro-2-methylphenylaminomethyl)-6-[4-(3-methoxycarbonylbenzoyloxy)-2-methoxyphenyl]-2,2,4-trimethyl-1,2-dihydroquioline (Compound No. 1-40) 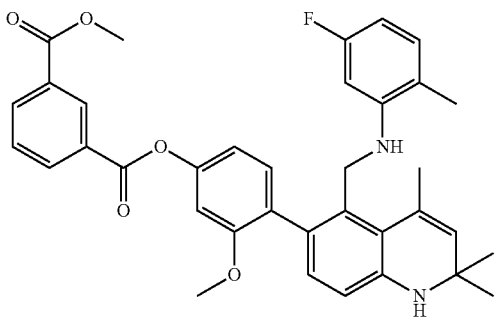 | $^1$H-NMR (500 MHz, DMSO-d$_6$) δ 1.11 (s, 3H), 1.20 (s, 3H), 1.92 (s, 3H), 2.05 (s, 3H), 3.73 (s, 3H), 3.92 (s, 3H), 3.95 (dd, J = 13.1, 4.9 Hz, 1H), 4.10 (dd, J = 13.1, 4.3 Hz, 1H), 4.23-4.25 (m, 1H), 5.41 (s, 1H), 6.03 (s, 1H), 6.08 (dd, J = 12.1, 2.5 Hz, 1H), 6.21 (td, J = 8.4, 2.5 Hz, 1H), 6.63 (d, J = 8.1 Hz, 1H), 6.77 (d, J = 8.1 Hz, 1H), 6.87-6.90 (m, 1H), 6.91 (dd, J = 8.2, 2.1 Hz, 1H), 7.07 (d, J = 2.1 Hz, 1H), 7.27 (d, J = 8.2 Hz, 1H), 7.79 (t, J = 7.8 Hz, 1H), 8.31 (dt, J = 7.8, 1.5 Hz, 1H), 8.39 (dt, J = 7.8, 1.5 Hz, 1H), 8.65 (t, J = 1.5 Hz, 1H) |
| 5-(5-Fluoro-2-methylphenylaminomethyl)-6-[2-methoxy-4-(2-methoxypyridin-3-ylcarbonyloxy)phenyl]-2,2,4-trimethyl-1,2-dihydroquioline (Compound No. 1-41) 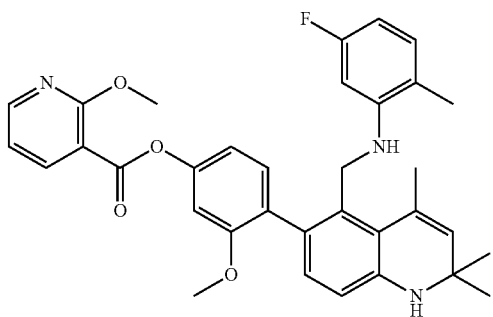 | $^1$H-NMR (500 MHz, DMSO-d$_6$) δ 1.11 (s, 3H), 1.20 (s, 3H), 1.91 (s, 3H), 2.05 (s, 3H), 3.72 (s, 3H), 3.95 (dd, J = 13.2, 4.3 Hz, 1H), 3.97 (s, 3H), 4.09 (dd, J = 13.2, 4.3 Hz, 1H), 4.23 (t, J = 4.3 Hz, 1H), 5.41 (s, 1H), 6.02 (s, 1H), 6.07 (dd, J = 12.2, 2.4 Hz, 1H), 6.21 (td, J = 8.4, 2.4 Hz, 1H), 6.62 (d, J = 8.2 Hz, 1H), 6.76 (d, J = 8.2 Hz, 1H), 6.85 (dd, J = 8.0, 2.2 Hz, 1H), 6.87-6.90 (m, 1H), 6.98 (d, J = 2.2 Hz, 1H), 7.19 (dd, J = 7.6, 4.9 Hz, 1H), 7.25 (d, J = 8.0 Hz, 1H), 8.40 (dd, J = 7.6, 2.0 Hz, 1H), 8.47 (dd, J = 4.9, 2.0 Hz, 1H) |
| 5-(5-Fluoro-2-methylphenylaminomethyl)-6-[2-methoxy-4-(3-methylfuran-2-ylcarbonyloxy)phenyl]-2,2,4-trimethyl-1,2-dihydroquioline (Compound No. 1-42) 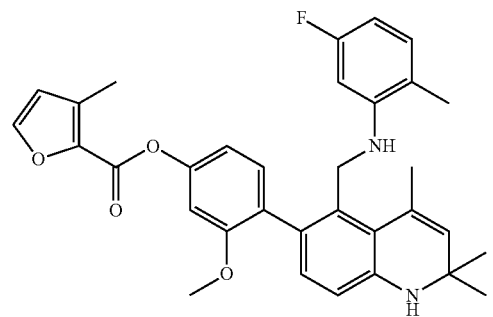 | $^1$H-NMR (400 MHz, DMSO-d$_6$) δ 1.11 (s, 3H), 1.19 (s, 3H), 1.91 (s, 3H), 2.04 (s, 3H), 2.38 (s, 3H), 3.72 (s, 3H), 3.94 (dd, J = 12.9, 4.3 Hz, 1H), 4.10 (dd, J = 12.9, 4.3 Hz, 1H), 4.24 (t, J = 4.3 Hz, 1H), 5.41 (s, 1H), 6.03 (s, 1H), 6.06 (dd, J = 12.2, 2.5 Hz, 1H), 6.20 (td, J = 8.5, 2.5 Hz, 1H), 6.62 (d, J = 8.3 Hz, 1H), 6.69 (d, J = 1.7 Hz, 1H), 6.75 (d, J = 8.3 Hz, 1H), 6.84 (dd, J = 8.2, 2.3 Hz, 1H), 6.86-6.90 (m, 1H), 6.98 (d, J = 2.3 Hz, 1H), 7.23 (d, J = 8.2 Hz, 1H), 7.95 (d, J = 1.7 Hz, 1H) |

| Compound | NMR |
|---|---|
| 6-(4-Dimethylaminocarbonyloxy-2-methoxyphenyl)-5-(2-methoxyphenylaminomethyl)-2,2,4-trimethyl-1,2-dihydroquioline (Compound No. 1-43) 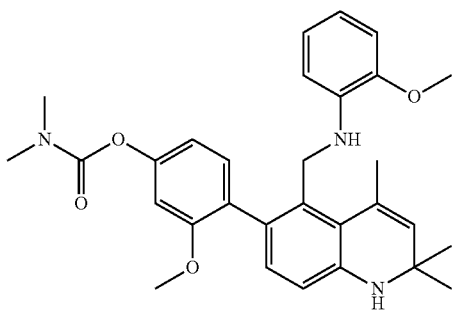 | $^1$H-NMR (400 MHz, DMSO-$d_6$) δ 1.15 (s, 3H), 1.21 (s, 3H), 2.06 (s, 3H), 2.90 (s, 3H), 3.02 (s, 3H), 3.64 (s, 3H), 3.71 (s, 3H), 3.82 (dd, J = 12.1, 3.3 Hz, 1H), 4.04 (dd, J = 12.1, 6.8 Hz, 1H), 4.23 (dd, J = 6.8, 3.3 Hz, 1H), 5.39 (s, 1H), 5.99 (s, 1H), 6.35 (dd, J = 7.8, 1.3 Hz, 1H), 6.51 (td, J = 7.8, 1.3 Hz, 1H), 6.60 (d, J = 8.3 Hz, 1H), 6.67 (dd, J = 7.8, 1.3 Hz, 1H), 6.68 (td, J = 7.8, 1.3 Hz, 1H), 6.70 (d, J = 8.3 Hz, 1H), 6.74 (dd, J = 8.1, 1.8 Hz, 1H), 6.75 (d, J = 1.8 Hz, 1H), 7.06 (d, J = 8.1 Hz, 1H) |
| 6-[2-Methoxy-4-(morpholin-4-ylcarbonyloxy)phenyl]-5-(2-methoxyphenylaminomethyl)-2,2,4-trimethyl-1,2-dihydroquioline (Compound No. 1-44) 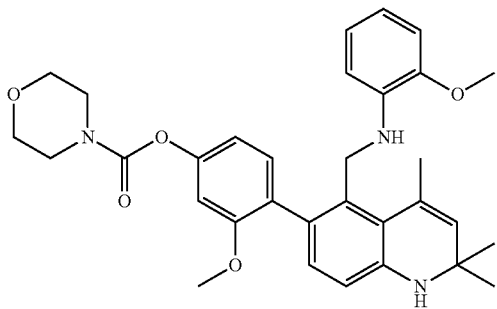 | $^1$H-NMR (400 MHz, DMSO-$d_6$) δ 1.15 (s, 3H), 1.21 (s, 3H), 2.07 (s, 3H), 3.38-3.43 (m, 2H), 3.54-3.59 (m, 2H), 3.61-3.64 (m, 4H), 3.64 (s, 3H), 3.71 (s, 3H), 3.82 (dd, J = 13.1, 3.7 Hz, 1H), 4.04 (dd, J = 13.1, 6.6 Hz, 1H), 4.23 (dd, J = 6.6, 3.7 Hz, 1H), 5.39 (s, 1H), 5.99 (s, 1H), 6.35 (dd, J = 7.7, 1.3 Hz, 1H), 6.51 (td, J = 7.7, 1.3 Hz, 1H), 6.60 (d, J = 8.3 Hz, 1H), 6.65-6.75 (m, 4H), 6.78 (d, J = 2.2 Hz, 1H), 7.07 (d, J = 8.3 Hz, 1H) |
| 5-(5-Fluoro-2-methylphenylaminomethyl)-6-[2-methoxy-4-(morpholin-4-ylcarbonyloxy)phenyl]-2,2,4-trimethyl-1,2-dihydroquioline (Compound No. 1-45) 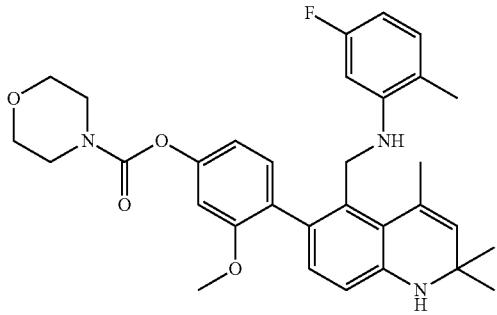 | $^1$H-NMR (400 MHz, DMSO-$d_6$) δ 1.10 (s, 3H), 1.19 (s, 3H), 1.90 (s, 3H), 2.04 (s, 3H), 3.38-3.44 (m, 2H), 3.54-3.60 (m, 2H), 3.63-3.66 (m, 4H), 3.70 (s, 3H), 3.91 (dd, J = 13.2, 4.8 Hz, 1H), 4.06 (dd, J = 13.2, 4.8 Hz, 1H), 4.19-4.23 (m, 1H), 5.40 (s, 1H), 6.01 (s, 1H), 6.04 (dd, J = 12.1, 2.5 Hz, 1H), 6.20 (td, J = 8.4, 2.5 Hz, 1H), 6.60 (d, J = 8.2 Hz, 1H), 6.73 (d, J = 8.2 Hz, 1H), 6.73 (dd, J = 8.2, 2.1 Hz, 1H), 6.84 (d, J = 2.1 Hz, 1H), 6.85-6.90 (m, 1H), 7.16 (d, J = 8.2 Hz, 1H) |

Example 2

5-(2-Methoxyphenylaminomethyl)-6-(2-methoxy-4-propylsulfonyloxyphenyl)-2,2,4-trimethyl-1,2-dihydroquioline (Compound No. 2-1)

6-(4-Hydroxy-2-methoxyphenyl)-5-(2-methoxyphenylaminomethyl)-2,2,4-trimethyl-1,2-dihydroquioline (Reference Compound No. 4-1, 25.0 mg, 0.0581 mmol) was dissolved in methylene dichloride (0.5 mL), triethylamine (16.2 μL, 0.116 mmol) and 1-propanesulfonyl chloride (6.5 μL, 0.058 mmol) were added thereto, and then the mixture was stirred under ice cooling for 30 minutes. The reaction mixture was purified by silica gel column chromatography (hexane-ethyl acetate) to give the titled compound (26.8 mg) as a colorless amorphous product. (Yield 86%)

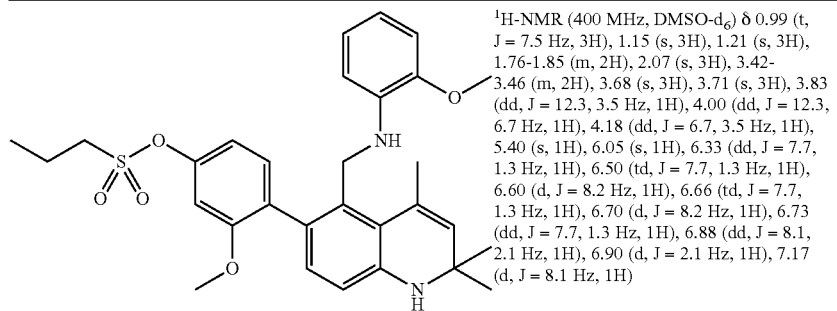

¹H-NMR (400 MHz, DMSO-d₆) δ 0.99 (t, J = 7.5 Hz, 3H), 1.15 (s, 3H), 1.21 (s, 3H), 1.76-1.85 (m, 2H), 2.07 (s, 3H), 3.42-3.46 (m, 2H), 3.68 (s, 3H), 3.71 (s, 3H), 3.83 (dd, J = 12.3, 3.5 Hz, 1H), 4.00 (dd, J = 12.3, 6.7 Hz, 1H), 4.18 (dd, J = 6.7, 3.5 Hz, 1H), 5.40 (s, 1H), 6.05 (s, 1H), 6.33 (dd, J = 7.7, 1.3 Hz, 1H), 6.50 (td, J = 7.7, 1.3 Hz, 1H), 6.60 (d, J = 8.2 Hz, 1H), 6.66 (td, J = 7.7, 1.3 Hz, 1H), 6.70 (d, J = 8.2 Hz, 1H), 6.73 (dd, J = 7.7, 1.3 Hz, 1H), 6.88 (dd, J = 8.1, 2.1 Hz, 1H), 6.90 (d, J = 2.1 Hz, 1H), 7.17 (d, J = 8.1 Hz, 1H)

Using Reference Compound No. 4-1 or 4-2, the following Compounds (No. 2-2~2-11) were obtained by a method similar to that of Compound No. 2-1.

6-(4-Isopropylsulfonyloxy-2-methoxyphenyl)-5-(2-methoxyphenylaminomethyl)-2,2,4-trimethyl-1,2-dihydroquioline (Compound No. 2-2)

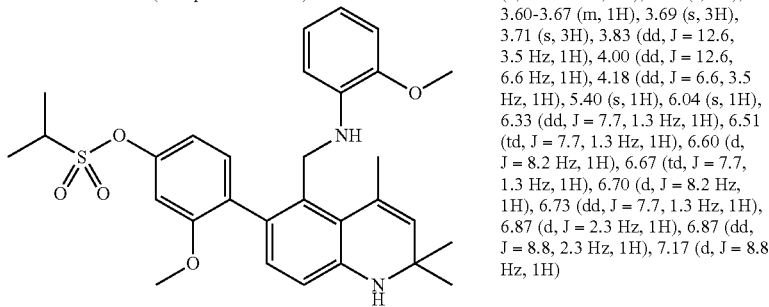

¹H-NMR (400 MHz, DMSO-d₆) δ 1.15 (s, 3H), 1.21 (s, 3H), 1.39 (d, J = 6.8 Hz, 6H), 2.07 (s, 3H), 3.60-3.67 (m, 1H), 3.69 (s, 3H), 3.71 (s, 3H), 3.83 (dd, J = 12.6, 3.5 Hz, 1H), 4.00 (dd, J = 12.6, 6.6 Hz, 1H), 4.18 (dd, J = 6.6, 3.5 Hz, 1H), 5.40 (s, 1H), 6.04 (s, 1H), 6.33 (dd, J = 7.7, 1.3 Hz, 1H), 6.51 (td, J = 7.7, 1.3 Hz, 1H), 6.60 (d, J = 8.2 Hz, 1H), 6.67 (td, J = 7.7, 1.3 Hz, 1H), 6.70 (d, J = 8.2 Hz, 1H), 6.73 (dd, J = 7.7, 1.3 Hz, 1H), 6.87 (d, J = 2.3 Hz, 1H), 6.87 (dd, J = 8.8, 2.3 Hz, 1H), 7.17 (d, J = 8.8 Hz, 1H)

6-(4-Isobutylsulfonyloxy-2-methoxyphenyl)-5-(2-methoxyphenylaminomethyl)-2,2,4-trimethyl-1,2-dihydroquioline (Compound No. 2-3)

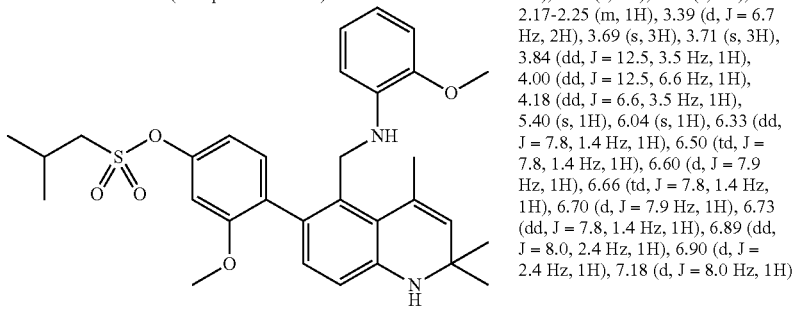

¹H-NMR (500 MHz, DMSO-d₆) δ 1.04 (d, J = 6.7 Hz, 6H), 1.15 (s, 3H), 1.21 (s, 3H), 2.07 (s, 3H), 2.17-2.25 (m, 1H), 3.39 (d, J = 6.7 Hz, 2H), 3.69 (s, 3H), 3.71 (s, 3H), 3.84 (dd, J = 12.5, 3.5 Hz, 1H), 4.00 (dd, J = 12.5, 6.6 Hz, 1H), 4.18 (dd, J = 6.6, 3.5 Hz, 1H), 5.40 (s, 1H), 6.04 (s, 1H), 6.33 (dd, J = 7.8, 1.4 Hz, 1H), 6.50 (td, J = 7.8, 1.4 Hz, 1H), 6.60 (d, J = 7.9 Hz, 1H), 6.66 (td, J = 7.8, 1.4 Hz, 1H), 6.70 (d, J = 7.9 Hz, 1H), 6.73 (dd, J = 7.8, 1.4 Hz, 1H), 6.89 (dd, J = 8.0, 2.4 Hz, 1H), 6.90 (d, J = 2.4 Hz, 1H), 7.18 (d, J = 8.0 Hz, 1H)

5-(2-Methoxyphenylaminomethyl)-6-[2-methoxy-4-(3,3,3-trifluoropropylsulfonyloxy)phenyl]-2,2,4-trimethyl-1,2-dihydroquioline (Compound No. 2-4)

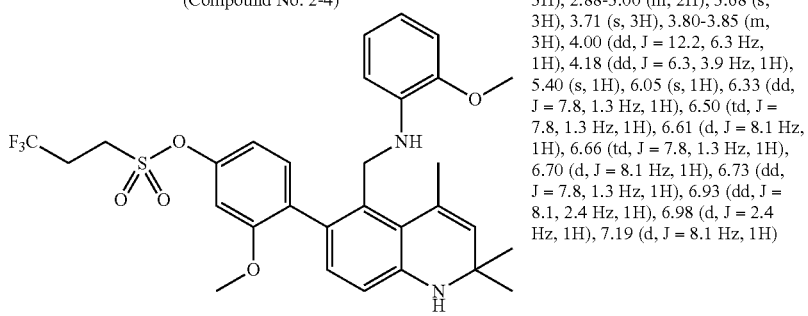

¹H-NMR (400 MHz, DMSO-d₆) δ 1.15 (s, 3H), 1.21 (s, 3H), 2.07 (s, 3H), 2.88-3.00 (m, 2H), 3.68 (s, 3H), 3.71 (s, 3H), 3.80-3.85 (m, 3H), 4.00 (dd, J = 12.2, 6.3 Hz, 1H), 4.18 (dd, J = 6.3, 3.9 Hz, 1H), 5.40 (s, 1H), 6.05 (s, 1H), 6.33 (dd, J = 7.8, 1.3 Hz, 1H), 6.50 (td, J = 7.8, 1.3 Hz, 1H), 6.61 (d, J = 8.1 Hz, 1H), 6.66 (td, J = 7.8, 1.3 Hz, 1H), 6.70 (d, J = 8.1 Hz, 1H), 6.73 (dd, J = 7.8, 1.3 Hz, 1H), 6.93 (dd, J = 8.1, 2.4 Hz, 1H), 6.98 (d, J = 2.4 Hz, 1H), 7.19 (d, J = 8.1 Hz, 1H)

| Compound | NMR |
|---|---|
| 6-(2-Methoxy-4-methylsulfonyloxyphenyl)-5-(2-methoxyphenylaminomethyl)-2,2,4-trimethyl-1,2-dihydroquioline (Compound No. 2-5) 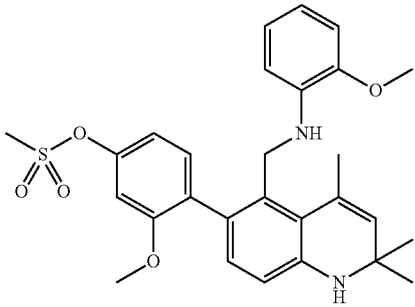 | $^1$H-NMR (500 MHz, CDCl$_3$) δ 1.26 (s, 3H), 1.30 (s, 3H), 2.19 (s, 3H), 3.01 (s, 3H), 3.70 (s, 3H), 3.75 (s, 3H), 3.89 (brs, 1H), 4.00 (d, J = 12.4 Hz, 1H), 4.06 (d, J = 12.4 Hz, 1H), 4.28 (s, 1H), 5.47 (s, 1H), 6.34 (dd, J = 7.8, 1.3 Hz, 1H), 6.56 (td, J = 7.8, 1.3 Hz, 1H), 6.56 (d, J = 7.9 Hz, 1H), 6.68 (dd, J = 7.8, 1.3 Hz, 1H), 6.75 (td, J = 7.8, 1.3 Hz, 1H), 6.78 (d, J = 2.2 Hz, 1H), 6.81 (d, J = 7.9 Hz, 1H), 6.82 (dd, J = 8.1, 2.2 Hz, 1H), 7.18 (d, J = 8.1 Hz, 1H) |
| 5-(5-Fluoro-2-methylphenylaminomethyl)-6-(2-methoxy-4-propylsulfonyloxyphenyl)-2,2,4-trimethyl-1,2-dihydroquioline (Compound No. 2-6) 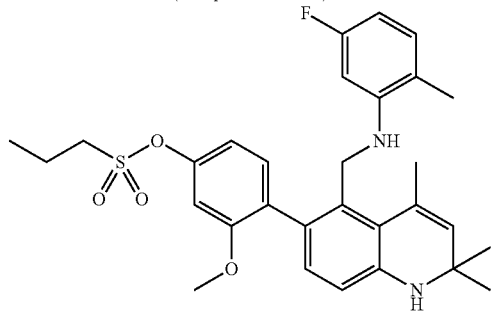 | $^1$H-NMR (500 MHz, DMSO-d$_6$) δ 1.00 (t, J = 7.5 Hz, 3H), 1.11 (s, 3H), 1.19 (s, 3H), 1.78-1.86 (m, 2H), 1.88 (s, 3H), 2.05 (s, 3H), 3.43-3.48 (m, 2H), 3.73 (s, 3H), 3.89 (dd, J = 13.1, 4.9 Hz, 1H), 4.07 (dd, J = 13.1, 4.3 Hz, 1H), 4.20-4.23 (m, 1H), 5.41 (s, 1H), 6.03 (dd, J = 12.2, 2.5 Hz, 1H), 6.04 (s, 1H), 6.19 (td, J = 8.5, 2.5 Hz, 1H), 6.61 (d, J = 8.1 Hz, 1H), 6.72 (d, J = 8.1 Hz, 1H), 6.84-6.88 (m, 1H), 6.91 (dd, J = 8.2, 2.4 Hz, 1H), 6.95 (d, J = 2.4 Hz, 1H), 7.25 (d, J = 8.2 Hz, 1H) |
| 6-(4-Cyclopropylsulfonyloxy-2-methoxyphenyl)-5-(2-methoxyphenylaminomethyl)-2,2,4-trimethyl-1,2-dihydroquioline (Compound No. 2-7) 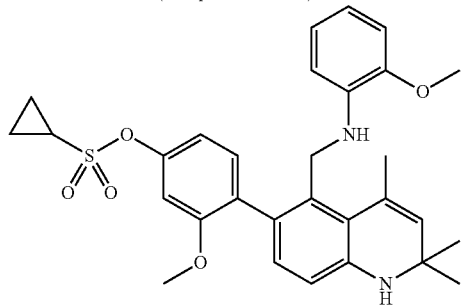 | $^1$H-NMR (500 MHz, DMSO-d$_6$) δ 0.80-1.05 (m, 4H), 1.15 (s, 3H), 1.22 (s, 3H), 2.09 (s, 3H), 2.91 (tt, J = 7.9, 4.9 Hz, 1H), 3.68 (s, 3H), 3.71 (s, 3H), 3.81 (dd, J = 12.4, 3.4 Hz, 1H), 3.99 (dd, J = 12.4, 6.2 Hz, 1H), 4.18 (dd, J = 6.2, 3.4 Hz, 1H), 5.40 (s, 1H), 6.03 (s, 1H), 6.32 (dd, J = 7.8, 1.2 Hz, 1H), 6.50 (td, J = 7.8, 1.2 Hz, 1H), 6.61 (d, J = 8.4 Hz, 1H), 6.66 (td, J = 7.8, 1.2 Hz, 1H), 6.71 (d, J = 8.4 Hz, 1H), 6.72 (dd, J = 7.8, 1.2 Hz, 1H), 6.89 (dd, J = 8.2, 2.2 Hz, 1H), 6.96 (d, J = 2.2 Hz, 1H), 7.17 (d, J = 8.2 Hz, 1H) |
| 6-(4-Ethylsulfonyloxy-2-methoxyphenyl)-5-(2-methoxyphenylaminomethyl)-2,2,4-trimethyl-1,2-dihydroquioline (Compound No. 2-8) 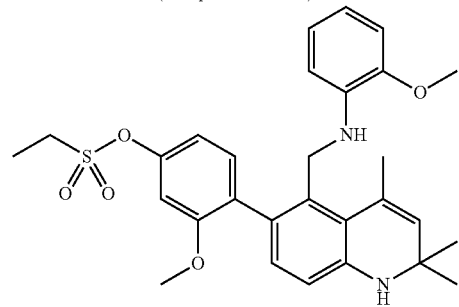 | $^1$H-NMR (500 MHz, DMSO-d$_6$) δ 1.15 (s, 3H), 1.21 (s, 3H), 1.32 (t, J = 7.3 Hz, 3H), 2.08 (s, 3H), 3.44 (q, J = 7.3 Hz, 2H), 3.69 (s, 3H), 3.71 (s, 3H), 3.84 (dd, J = 12.4, 3.7 Hz, 1H), 3.99 (dd, J = 12.4, 6.3 Hz, 1H), 4.18 (dd, J = 6.3, 3.7 Hz, 1H), 5.40 (s, 1H), 6.03 (s, 1H), 6.33 (dd, J = 7.8, 1.3 Hz, 1H), 6.50 (td, J = 7.8, 1.3 Hz, 1H), 6.60 (d, J = 8.1 Hz, 1H), 6.66 (td, J = 7.8, 1.3 Hz, 1H), 6.70 (d, J = 8.1 Hz, 1H), 6.73 (dd, J = 7.8, 1.3 Hz, 1H), 6.88 (dd, J = 8.2, 2.4 Hz, 1H), 6.90 (d, J = 2.4 Hz, 1H), 7.17 (d, J = 8.2 Hz, 1H) |

| | |
|---|---|
| 6-(4-Butylsulfonyloxy-2-methoxyphenyl)-5-(2-methoxyphenylaminomethyl)-2,2,4-trimethyl-1,2-dihydroquioline (Compound No. 2-9) 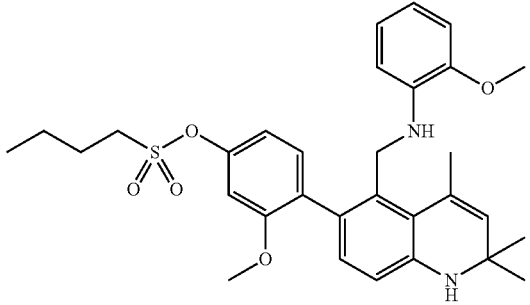 [SMILES: CCCCS(=O)(=O)Oc1ccc(-c2ccc3c(c2CNc2ccccc2OC)C(C)=CC(C)(C)N3)c(OC)c1] | $^1$H-NMR (400 MHz, DMSO-$d_6$) δ 0.88 (t, J = 7.3 Hz, 3H), 1.15 (s, 3H), 1.21 (s, 3H), 1.35-1.45 (m, 2H), 1.72-1.80 (m, 2H), 2.07 (s, 3H), 3.43-3.47 (m, 2H), 3.68 (s, 3H), 3.71 (s, 3H), 3.84 (dd, J = 12.3, 3.4 Hz, 1H), 4.00 (dd, J = 12.3, 6.3 Hz, 1H), 4.18 (dd, J = 6.3, 3.4 Hz, 1H), 5.40 (s, 1H), 6.04 (s, 1H), 6.33 (dd, J = 7.7, 1.3 Hz, 1H), 6.50 (td, J = 7.7, 1.3 Hz, 1H), 6.60 (d, J = 8.3 Hz, 1H), 6.66 (td, J = 7.7, 1.3 Hz, 1H), 6.70 (d, J = 8.3 Hz, 1H), 6.73 (dd, J = 7.7, 1.3 Hz, 1H), 6.88 (dd, J = 8.1, 2.3 Hz, 1H), 6.90 (d, J = 2.3 Hz, 1H), 7.17 (d, J = 8.1 Hz, 1H) |
| 6-(4-Cyclopentylsulfonyloxy-2-methoxyphenyl)-5-(2-methoxyphenylaminomethyl)-2,2,4-trimethyl-1,2-dihydroquioline (Compound No. 2-10) 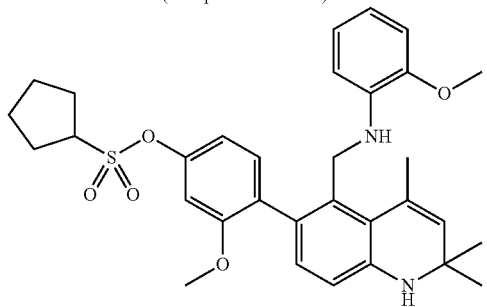 | $^1$H-NMR (500 MHz, DMSO-$d_6$) δ 1.15 (s, 3H), 1.21 (s, 3H), 1.55-1.63 (m, 2H), 1.65-1.73 (m, 2H), 1.92-1.99 (m, 2H), 2.00-2.07 (m, 2H), 2.07 (s, 3H), 3.69 (s, 3H), 3.71 (s, 3H), 3.83 (dd, J = 12.7, 3.9 Hz, 1H), 3.85-3.91 (m, 1H), 3.99 (dd, J = 12.7, 6.2 Hz, 1H), 4.18 (dd, J = 6.2, 3.9 Hz, 1H), 5.40 (s, 1H), 6.03 (s, 1H), 6.33 (dd, J = 7.8, 1.2 Hz, 1H), 6.50 (td, J = 7.8, 1.2 Hz, 1H), 6.60 (d, J = 8.2 Hz, 1H), 6.66 (td, J = 7.8, 1.2 Hz, 1H), 6.70 (d, J = 8.2 Hz, 1H), 6.73 (dd, J = 7.8, 1.2 Hz, 1H), 6.87 (d, J = 2.3 Hz, 1H), 6.87 (dd, J = 8.9, 2.3 Hz, 1H), 7.17 (d, J = 8.9 Hz, 1H) |
| 5-(5-Fluoro-2-methylphenylaminomethyl)-6-(2-methoxy-4-methylsulfonyloxyphenyl)-2,2,4-trimethyl-1,2-dihydroquioline (Compound No. 2-11) 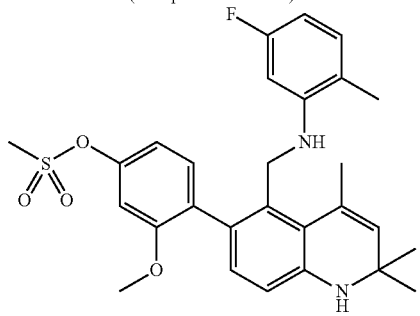 | 1H-NMR (500 MHz, DMSO-$d_6$) δ 1.11 (s, 3H), 1.19 (s, 3H), 1.88 (s, 3H), 2.05 (s, 3H), 3.34 (s, 3H), 3.74 (s, 3H), 3.90 (dd, J = 13.1, 4.4 Hz, 1H), 4.08 (dd, J = 13.1, 4.4 Hz, 1H), 4.23 (t, J = 4.4 Hz, 1H), 5.41 (s, 1H), 6.02 (dd, J = 12.2, 2.4 Hz, 1H), 6.04 (s, 1H), 6.19 (td, J = 8.5, 2.4 Hz, 1H), 6.61 (d, J = 8.2 Hz, 1H), 6.72 (d, J = 8.2 Hz, 1H), 6.85-6.88 (m, 1H), 6.92 (dd, J = 8.2, 2.3 Hz, 1H), 7.00 (d, J = 2.3 Hz, 1H), 7.26 (d, J = 8.2 Hz, 1H) |

Example 3

6-(2-Methoxy-4-methoxycarbonyloxyphenyl)-5-(2-methoxyphenylaminomethyl)-2,2,4-trimethyl-1,2-dihydroquioline (Compound No. 3-1)

6-(4-Hydroxy-2-methoxyphenyl)-5-(2-methoxyphenylaminomethyl)-2,2,4-trimethyl-1,2-dihydroquioline (Reference Compound No. 4-1, 20.0 mg, 0.0465 mmol) was dissolved in anhydrous methylene dichloride (1.0 mL), triethylamine (13 μL, 0.093 mmol) and methyl chlorocarbonate (3.6 μL, 0.047 mmol) were added thereto under ice cooling, and then the mixture was stirred for 10 minutes. The reaction mixture was purified by silica gel column chromatography (hexane-ethyl acetate) to give the titled compound (12.9 mg) as a colorless amorphous product. (Yield 57%)

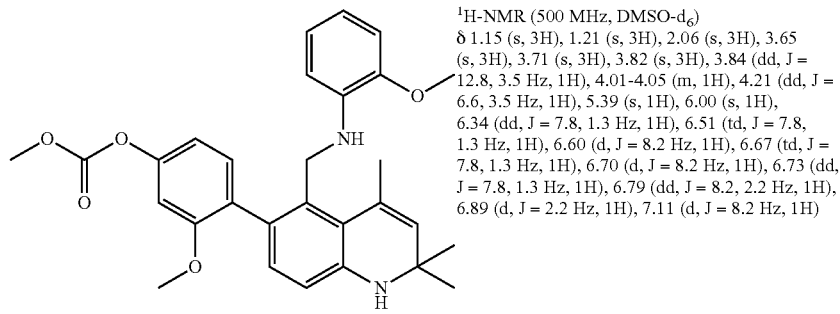

¹H-NMR (500 MHz, DMSO-d₆)
δ 1.15 (s, 3H), 1.21 (s, 3H), 2.06 (s, 3H), 3.65 (s, 3H), 3.71 (s, 3H), 3.82 (s, 3H), 3.84 (dd, J = 12.8, 3.5 Hz, 1H), 4.01-4.05 (m, 1H), 4.21 (dd, J = 6.6, 3.5 Hz, 1H), 5.39 (s, 1H), 6.00 (s, 1H), 6.34 (dd, J = 7.8, 1.3 Hz, 1H), 6.51 (td, J = 7.8, 1.3 Hz, 1H), 6.60 (d, J = 8.2 Hz, 1H), 6.67 (td, J = 7.8, 1.3 Hz, 1H), 6.70 (d, J = 8.2 Hz, 1H), 6.73 (dd, J = 7.8, 1.3 Hz, 1H), 6.79 (dd, J = 8.2, 2.2 Hz, 1H), 6.89 (d, J = 2.2 Hz, 1H), 7.11 (d, J = 8.2 Hz, 1H)

Using Reference Compound No. 4-1, the following Compounds (No. 3-2 and 3-3) were obtained by a method similar to that of Compound No. 3-1.

6-(4-Chlorophenyloxycarbonyloxy-2-methoxyphenyl)-5-(2-methoxyphenylaminomethyl)-2,2,4-trimethyl-1,2-dihydroquioline (Compound No. 3-2)

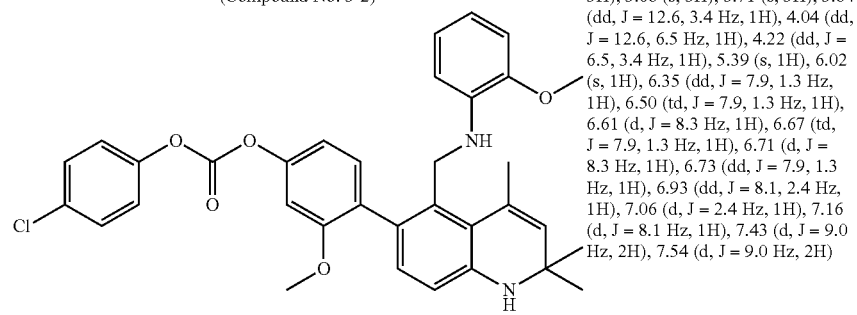

¹H-NMR (400 MHz, DMSO-d₆)
δ 1.15 (s, 3H), 1.21 (s, 3H), 2.07 (s, 3H), 3.68 (s, 3H), 3.71 (s, 3H), 3.84 (dd, J = 12.6, 3.4 Hz, 1H), 4.04 (dd, J = 12.6, 6.5 Hz, 1H), 4.22 (dd, J = 6.5, 3.4 Hz, 1H), 5.39 (s, 1H), 6.02 (s, 1H), 6.35 (dd, J = 7.9, 1.3 Hz, 1H), 6.50 (td, J = 7.9, 1.3 Hz, 1H), 6.61 (d, J = 8.3 Hz, 1H), 6.67 (td, J = 7.9, 1.3 Hz, 1H), 6.71 (d, J = 8.3 Hz, 1H), 6.73 (dd, J = 7.9, 1.3 Hz, 1H), 6.93 (dd, J = 8.1, 2.4 Hz, 1H), 7.06 (d, J = 2.4 Hz, 1H), 7.16 (d, J = 8.1 Hz, 1H), 7.43 (d, J = 9.0 Hz, 2H), 7.54 (d, J = 9.0 Hz, 2H)

6-(4-t-Butoxycarbonyloxy-2-methoxyphenyl)-5-(2-methoxyphenylaminomethyl)-2,2,4-trimethyl-1,2-dihydroquioline (Compound No. 3-3)

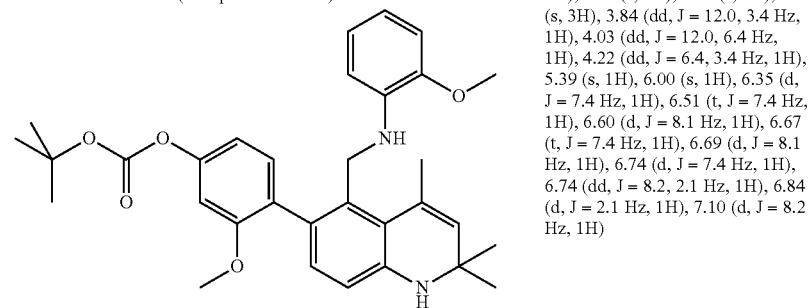

¹H-NMR (500 MHz, DMSO-d₆)
δ 1.15 (s, 3H), 1.21 (s, 3H), 1.48 (s, 9H), 2.06 (s, 3H), 3.65 (s, 3H), 3.71 (s, 3H), 3.84 (dd, J = 12.0, 3.4 Hz, 1H), 4.03 (dd, J = 12.0, 6.4 Hz, 1H), 4.22 (dd, J = 6.4, 3.4 Hz, 1H), 5.39 (s, 1H), 6.00 (s, 1H), 6.35 (d, J = 7.4 Hz, 1H), 6.51 (t, J = 7.4 Hz, 1H), 6.60 (d, J = 8.1 Hz, 1H), 6.67 (t, J = 7.4 Hz, 1H), 6.69 (d, J = 8.1 Hz, 1H), 6.74 (d, J = 7.4 Hz, 1H), 6.74 (dd, J = 8.2, 2.1 Hz, 1H), 6.84 (d, J = 2.1 Hz, 1H), 7.10 (d, J = 8.2 Hz, 1H)

Example 4

6-(4-Chlorophenylaminocarbonyloxy-2-methoxyphenyl)-5-(2-methoxyphenylaminomethyl)-2,2,4-trimethyl-1,2-dihydroquioline (Compound No. 4-1)

6-(4-Hydroxy-2-methoxyphenyl)-5-(2-methoxyphenylaminomethyl)-2,2,4-trimethyl-1,2-dihydroquioline (Reference Compound No. 4-1, 20.0 mg, 0.0465 mmol) was dissolved in anhydrous methylene dichloride (1.0 mL), triethylamine (13 µL, 0.093 mmol) and 4-chlorophenyl isocyanate (6.0 µL, 0.047 mmol) were added thereto under ice cooling, and then the mixture was stirred for 30 minutes. The reaction mixture was purified by silica gel column chromatography (hexane-ethyl acetate) to give the titled compound (26.3 mg) as a colorless amorphous product. (Yield 97%)

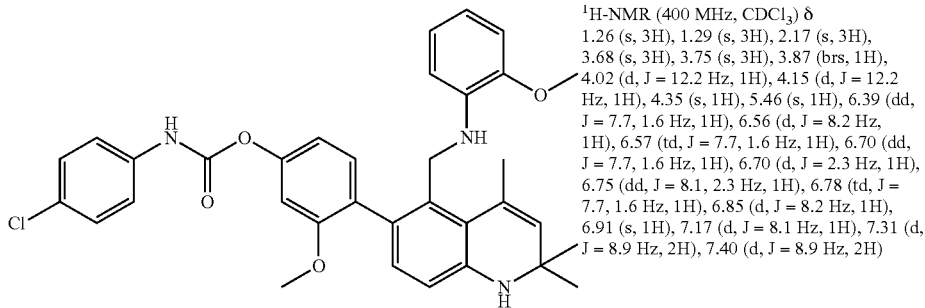

¹H-NMR (400 MHz, CDCl₃) δ
1.26 (s, 3H), 1.29 (s, 3H), 2.17 (s, 3H), 3.68 (s, 3H), 3.75 (s, 3H), 3.87 (brs, 1H), 4.02 (d, J = 12.2 Hz, 1H), 4.15 (d, J = 12.2 Hz, 1H), 4.35 (s, 1H), 5.46 (s, 1H), 6.39 (dd, J = 7.7, 1.6 Hz, 1H), 6.56 (d, J = 8.2 Hz, 1H), 6.57 (td, J = 7.7, 1.6 Hz, 1H), 6.70 (dd, J = 7.7, 1.6 Hz, 1H), 6.70 (d, J = 2.3 Hz, 1H), 6.75 (dd, J = 8.1, 2.3 Hz, 1H), 6.78 (td, J = 7.7, 1.6 Hz, 1H), 6.85 (d, J = 8.2 Hz, 1H), 6.91 (s, 1H), 7.17 (d, J = 8.1 Hz, 1H), 7.31 (d, J = 8.9 Hz, 2H), 7.40 (d, J = 8.9 Hz, 2H)

6-[4-[N-(2-Dimethylaminoethyl)-N-methylaminocarbonyloxy]-2-methoxyphenyl]-5-(2-methoxyphenylaminomethyl)-2,2,4-trimethyl-1,2-dihydroquioline (Compound No. 4-2)

A mixture of 6-(4-hydroxy-2-methoxyphenyl)-5-[N-(2-methoxyphenyl)-N-(9-fluorenylmethoxycarbonyl)aminomethyl]-2,2,4-trimethyl-1,2-dihydroquioline (Reference Compound No. 5, 25.0 mg, 0.0383 mmol), 1,1'-carbonyldiimidazole (62.0 mg, 0.382 mmol) and 4-dimethylaminopyridine (0.5 mg, 0.004 mmol) was dissolved in anhydrous tetrahydrofuran (1 mL), and then the solution was stirred at room temperature for 4.5 hours. N,N,N'-trimethylethylenediamine (39.2 mg, 0.383 mmol) was added thereto, and then the mixture was stirred at 60° C. for 2 hours. The reaction mixture was purified by silica gel column chromatography (hexane-ethyl acetate). The obtained colorless amorphous product was dissolved in N,N-dimethylformamide (1 mL), and then piperidine (50 μL) was added thereto. After the reaction mixture was stirred at room temperature for minutes, it was diluted with ethyl acetate (20 mL). The mixture was washed with water (15 mL) and saturated brine (15 mL) successively, dried over anhydrous magnesium sulfate, and then the solvent was removed under reduced pressure. The obtained residue was purified by silica gel column chromatography (hexane-ethyl acetate) to give the titled compound (9.9 mg) as a colorless amorphous product. (Yield 47%)

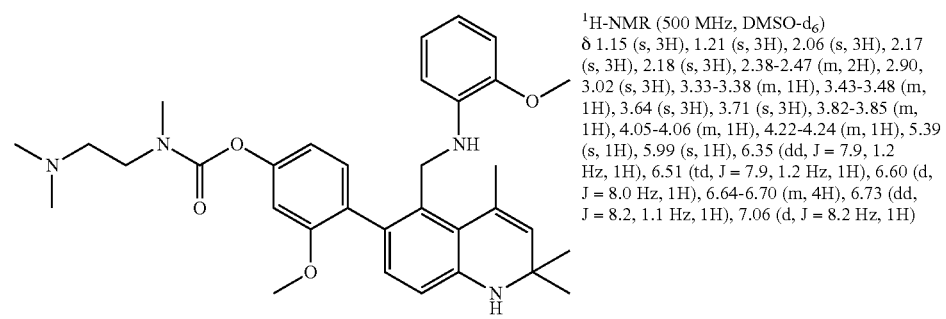

¹H-NMR (500 MHz, DMSO-d₆)
δ 1.15 (s, 3H), 1.21 (s, 3H), 2.06 (s, 3H), 2.17 (s, 3H), 2.18 (s, 3H), 2.38-2.47 (m, 2H), 2.90, 3.02 (s, 3H), 3.33-3.38 (m, 1H), 3.43-3.48 (m, 1H), 3.64 (s, 3H), 3.71 (s, 3H), 3.82-3.85 (m, 1H), 4.05-4.06 (m, 1H), 4.22-4.24 (m, 1H), 5.39 (s, 1H), 5.99 (s, 1H), 6.35 (dd, J = 7.9, 1.2 Hz, 1H), 6.51 (td, J = 7.9, 1.2 Hz, 1H), 6.60 (d, J = 8.0 Hz, 1H), 6.64-6.70 (m, 4H), 6.73 (dd, J = 8.2, 1.1 Hz, 1H), 7.06 (d, J = 8.2 Hz, 1H)

Using Reference Compound No. 4-1 or 4-2, the following Compounds (No. 4-3~4-5) were obtained by a method similar to that of Compound No. 4-1 or 4-2.

5-(2-Methoxyphenylaminomethyl)-6-[2-methoxy-4-(pyridin-3-ylaminocarbonyloxy)phenyl]-2,2,4-trimethyl-1,2-dihydroquioline
(Compound No. 4-3)

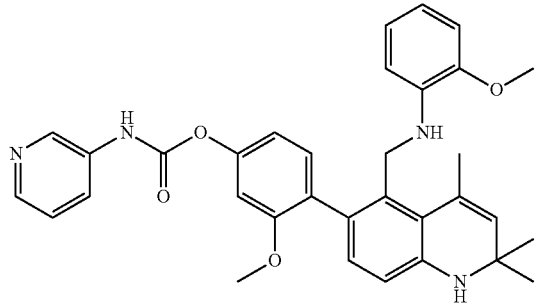 [SMILES: COc1ccccc1NCc1c(-c2ccc(OC(=O)Nc3cccnc3)cc2OC)ccc2c1C(C)=CC(C)(C)N2]

$^1$H-NMR (400 MHz, CDCl$_3$) δ 1.26 (s, 3H), 1.30 (s, 3H), 2.17 (s, 3H), 3.68 (s, 3H), 3.75 (s, 3H), 3.86 (brs, 1H), 4.03 (d, J = 12.1 Hz, 1H), 4.15 (d, J = 12.1 Hz, 1H), 4.34 (s, 1H), 5.46 (s, 1H), 6.39 (dd, J = 7.7, 1.4 Hz, 1H), 6.57 (d, J = 8.1 Hz, 1H), 6.57 (td, J = 7.7, 1.4 Hz, 1H), 6.70 (dd, J = 7.7, 1.4 Hz, 1H), 6.71 (d, J = 2.3 Hz, 1H), 6.77 (dd, J = 8.2, 2.3 Hz, 1H), 6.78 (td, J = 7.7, 1.4 Hz, 1H), 6.86 (d, J = 8.1 Hz, 1H), 7.02 (s, 1H), 7.18 (d, J = 8.2 Hz, 1H), 7.30 (dd, J = 8.4, 4.8 Hz, 1H), 8.02-8.07 (m, 1H), 8.37 (dd, J = 4.8, 1.5 Hz, 1H), 8.57 (d, J = 2.2 Hz, 1H)

6-[4-[N-(2-Dimethylaminoethyl)-N-methylaminocarbonyloxy]-2-methoxyphenyl]-5-(5-fluoro-2-methylphenylaminomethyl)-2,2,4-trimethyl-1,2-di-hydroquioline
(Compound No. 4-4)

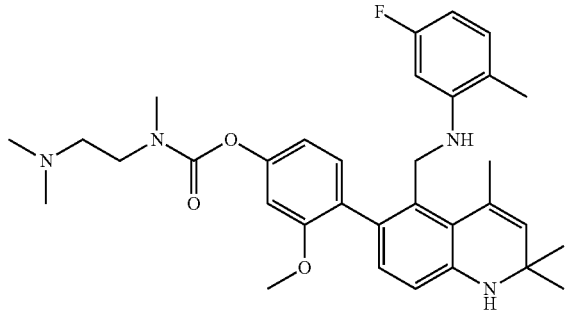

$^1$H-NMR (400 MHz, CDCl$_3$) δ 1.24 (s, 3H), 1.29 (s, 3H), 1.93 (s, 3H), 2.10 (s, 3H), 2.30 (s, 6H), 2.53-2.58 (m, 2H), 3.04, 3.12 (s, 3H), 3.47-3.55 (m, 2H), 3.69 (s, 4H), 4.09 (s, 3H), 5.48 (s, 1H), 6.08 (dd, J = 11.7, 2.4 Hz, 1H), 6.23 (td, J = 8.4, 2.4 Hz, 1H), 6.58 (d, J = 8.1 Hz, 1H), 6.70-6.75 (m, 2H), 6.85-6.88 (m, 2H), 7.14 (d, J = 8.1 Hz, 1H)

6-[4-[N-(2-Dimethylaminoethyl)-N-ethylaminocarbonyloxy]-2-methoxyphenyl]-5-(5-fluoro-2-methylphenylaminomethyl)-2,2,4-trimethyl-1,2-di-hydroquioline
(Compound No. 4-5)

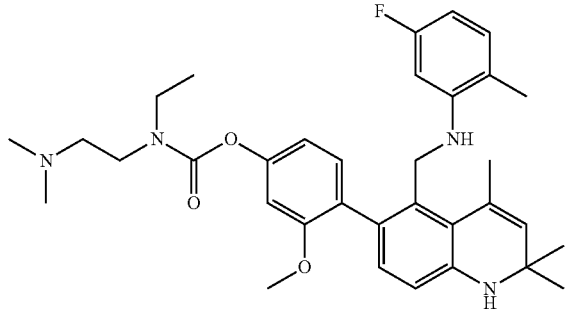

$^1$H-NMR (400 MHz, CDCl$_3$) δ 1.21-1.27 (m, 3H), 1.24 (s, 3H), 1.29 (s, 3H), 1.93 (s, 3H), 2.10 (s, 3H), 2.30 (s, 6H), 2.53-2.58 (m, 2H), 3.40-3.52 (m, 4H), 3.70 (s, 4H), 4.10 (s, 2H), 5.48 (br s, 1H), 6.08 (dd, J = 11.8, 2.4 Hz, 1H), 6.23 (td, J = 8.4, 2.4 Hz, 1H), 6.58 (d, J = 8.1 Hz, 1H), 6.69-6.72 (m, 1H), 6.74 (dd, J = 8.1, 2.2 Hz, 1H), 6.84-6.89 (m, 2H), 7.14 (d, J = 8.1 Hz, 1H)

Preparation Examples

Hereinafter, typical preparation examples of the present compound are shown.

1) Tablet (in 150 mg)

| | |
|---|---|
| Present compound | 1 mg |
| Lactose | 100 mg |
| Cornstarch | 40 mg |
| Carboxymethyl cellulose calcium | 4.5 mg |
| Hydroxypropyl cellulose | 4 mg |
| Magnesium stearate | 0.5 mg |

A tablet of the above-mentioned formulation is coated with 3 mg of a coating agent (for example, a coating agent which is used conventionally such as hydroxypropylmethyl cellulose, macrogol or a silicone resin), whereby an objective tablet can be obtained. In addition, a desired tablet can be obtained by appropriately changing the kind and/or amount of the present compound and additives.

2) Capsule (in 150 mg)

| | |
|---|---|
| Present compound | 5 mg |
| Lactose | 135 mg |
| Carboxymethyl cellulose calcium | 4.5 mg |
| Hydroxypropyl cellulose | 4 mg |
| Magnesium stearate | 1.5 mg |

A desired capsule can be obtained by appropriately changing the kind and/or amount of the present compound and additives.

3) Eye Drop (in 100 mL)

| Present compound | 100 mg |
|---|---|
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kind and/or amount of the present compound and additives.

[Pharmacological Test]

1. Evaluation Test for Binding Activity to Glucocorticoid Receptor (hereinafter referred to as "GR")

In order to evaluate a binding activity to GR, a receptor competitor assay was carried out by a fluorescence polarization method. In the assay, a GR competitor assay kit (manufactured by Invitrogen, cat No. P2816) was used, and a procedure was carried out according to the protocol attached to the kit. Hereinafter, the specific method will be described.

(Preparation of Reagents)

GR screening buffer: A buffer containing 10 mM potassium phosphate (pH 7.4), 20 mM sodium molybdate ($Na_2MoO_4$), 0.1 mM ethylene diamine tetraacetic acid (EDTA), 5 mM dithiothreitol (DTT), 0.1 mM stabilizing peptide and 2% dimethylsulfoxide was prepared.

4×GS1 solution: Fluormone™ GS1, which is a fluorescent glucocorticoid ligand, was diluted with GR screening buffer, whereby a 4 nM solution was prepared.

4×GR solution: Recombinant human GR was diluted with GR screening buffer, whereby a 16 nM solution was prepared.

(Preparation of Test Compound Solution)

After a test compound was dissolved in dimethylsulfoxide, the resulting solution was diluted with GR screening buffer, whereby a 20 µM test compound solution was prepared.

(Test Method and Measurement Method)

1) The test compound solution was added in an amount of 10 µL into each well of a 384-well plate, and then, 4×GS1 solution and 4×GR solution were added in an amount of 5 µL into each well, respectively.

2) The plate was incubated in a dark place at room temperature for 2 to 4 hours.

3) By using a multimode plate reader, Analyst™ HT (manufactured by LJL Biosystems), fluorescence polarization of each well was measured. As the blank, a well containing GR screening buffer in place of the test compound and 4×GS1 solution was used.

4) The same procedure as that in the above 1) to 3) was carried out except that GR screening buffer was used in place of the test compound solution, and the obtained result was taken as the negative control.

5) The same procedure as that in the above 1) to 3) was carried out except that 2 mM dexamethasone was used in place of the test compound solution, and the obtained result was taken as the positive control.

(Calculation Equation of GR Binding Ratio)

A GR binding ratio (%) was calculated from the following equation.

GR binding ratio(%)=100×[1−(fluorescence polarization of test compound solution−fluorescence polarization of positive control solution)/(fluorescence polarization of negative control solution−fluorescence polarization of positive control solution)]

(Test Results and Discussion)

As an example of the test results, the GR binding ratios (%) of the test compounds (Compound 1-1, Compound 1-2, Compound 1-3, Compound 1-4, Compound 1-5, Compound 1-6, Compound 1-7, Compound 1-8, Compound 1-9, Compound 1-10, Compound 1-12, Compound 1-13, Compound 1-14, Compound 1-15, Compound 1-16, Compound 1-17, Compound 1-18, Compound 1-22, Compound 1-23, Compound 1-26, Compound 1-27, Compound 1-28, Compound 1-29, Compound 1-30, Compound 1-31, Compound 1-32, Compound 1-33, Compound 1-34, Compound 1-35, Compound 1-38, Compound 1-39, Compound 1-41, Compound 1-42, Compound 1-43, Compound 1-44, Compound 1-45, Compound 2-1, Compound 2-2, Compound 2-5, Compound 2-6, Compound 2-7, Compound 2-10, Compound 2-11, Compound 4-2; Compound 4-3, Compound 4-4) are shown in Table I.

TABLE I

| Test compound | GR Binding ratio (%) |
|---|---|
| Compound 1-1 | 92 |
| Compound 1-2 | 100 |
| Compound 1-3 | 95 |
| Compound 1-4 | 95 |
| Compound 1-5 | 93 |
| Compound 1-6 | 97 |
| Compound 1-7 | 95 |
| Compound 1-8 | 98 |
| Compound 1-9 | 90 |
| Compound 1-10 | 93 |
| Compound 1-12 | 99 |
| Compound 1-13 | 100 |
| Compound 1-14 | 99 |
| Compound 1-15 | 99 |
| Compound 1-16 | 100 |
| Compound 1-17 | 99 |
| Compound 1-18 | 86 |
| Compound 1-22 | 81 |
| Compound 1-23 | 86 |
| Compound 1-26 | 90 |
| Compound 1-27 | 87 |
| Compound 1-28 | 88 |
| Compound 1-29 | 93 |
| Compound 1-30 | 94 |
| Compound 1-31 | 92 |
| Compound 1-32 | 90 |
| Compound 1-33 | 100 |
| Compound 1-34 | 100 |
| Compound 1-35 | 100 |
| Compound 1-38 | 100 |
| Compound 1-39 | 100 |
| Compound 1-41 | 100 |
| Compound 1-42 | 100 |
| Compound 1-43 | 96 |
| Compound 1-44 | 96 |
| Compound 1-45 | 100 |
| Compound 2-1 | 100 |
| Compound 2-2 | 100 |
| Compound 2-5 | 93 |
| Compound 2-6 | 100 |
| Compound 2-7 | 100 |
| Compound 2-10 | 100 |
| Compound 2-11 | 100 |
| Compound 4-2 | 98 |
| Compound 4-3 | 91 |
| Compound 4-4 | 100 |

Incidentally, in the case where the GR binding ratio of the test compound is 100% or more, the GR binding ratio is indicated by 100%.

As is apparent from Table I, the present compound showed an excellent GR binding activity. Accordingly, the present compound can be used as a GR modulator, and is useful for a preventive or therapeutic agent particularly for GR-related diseases, that is, metabolic disorders, inflammatory diseases, autoimmune diseases, allergic diseases, central nervous system diseases, cardiovascular diseases, homeostasis-related diseases, glaucoma and the like.

The invention claimed is:

1. A method for treating a disease related to a glucocorticoid receptor, said disease selected from the group consisting of a metabolic disorder, an allergic disease, a central nervous system disease, a cardiovascular disease, a homeostasis-related disease and glaucoma, the method comprising administering a pharmacologically effective amount of a compound represented by the following formula (1) or a pharmaceutically acceptable salt thereof as an active ingredient to a patient:

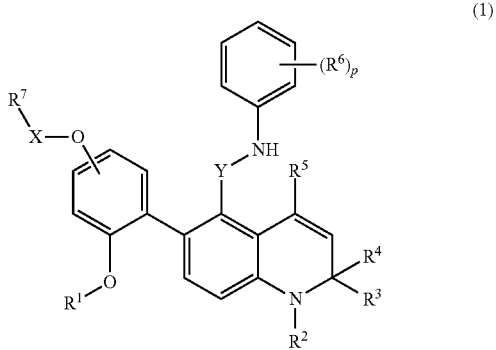

(1)

, wherein $R^1$ represents a hydrogen atom or a lower alkyl group;

$R^2$ represents a hydrogen atom or a lower alkyl group;

$R^3$ and $R^4$ are the same or different and represent a hydrogen atom or a lower alkyl group;

$R^5$ represents a hydrogen atom or a lower alkyl group;

$R^6$ represents a halogen atom, a lower alkyl group, a hydroxy group, a lower alkoxy group, a nitro group or a cyano group;

X represents —CO—, —C(O)NR$^8$—, —S(O)— or —S(O)$_2$—;

$R^7$ and/or $R^8$ are the same or different and represent a hydrogen atom, a lower alkyl group which optionally has a substituent, a lower alkenyl group which optionally has a substituent, a lower alkynyl group which optionally has a substituent, a lower cycloalkyl group which optionally has a substituent, an aryl group which optionally has a substituent, a heterocyclic group which optionally has a substituent, a lower alkoxy group which optionally has a substituent, a lower alkenyloxy group which optionally has a substituent, a lower alkynyloxy group which optionally has a substituent, a lower cycloalkyloxy group which optionally has a substituent, an aryloxy group which optionally has a substituent or a heterocyclic oxy group which optionally has a substituent;

Y represents a lower alkylene group;

p represents 0, 1, 2 or 3, in the case where p is 2 or 3, each $R^6$ is the same or different.

2. The method according to claim 1, wherein in the formula (1), $R^1$ represents a hydrogen atom or a lower alkyl group;

$R^2$ represents a hydrogen atom or a lower alkyl group;

$R^3$ and $R^4$ are the same or different and represent a hydrogen atom or a lower alkyl group;

$R^5$ represents a hydrogen atom or a lower alkyl group;

$R^6$ represents a halogen atom, a lower alkyl group, a hydroxy group, a lower alkoxy group, a nitro group or a cyano group;

X represents —CO—, —C(O)NR$^8$—, —S(O)— or —S(O)$_2$—;

$R^7$ and/or $R^8$ are the same or different and represent a hydrogen atom, a lower alkyl group, a lower alkenyl group, a lower alkynyl group, a lower cycloalkyl group, an aryl group, a heterocyclic group, a lower alkoxy group, a lower alkenyloxy group, a lower alkynyloxy group, a lower cycloalkyloxy group, an aryloxy group or a heterocyclic oxy group;

in the case where $R^7$ and/or $R^8$ is a lower alkyl group, a lower alkenyl group, a lower alkynyl group, a lower alkoxy group, a lower alkenyloxy group or a lower alkynyloxy group, the lower alkyl group, the lower alkenyl group, the lower alkynyl group, the lower alkoxy group, the lower alkenyloxy group or the lower alkynyloxy group optionally has one or a plurality of substituents selected from the group consisting of a halogen atom, a lower cycloalkyl group, an aryl group, a heterocyclic group, a hydroxy group, a lower alkoxy group, a lower alkenyloxy group, a lower alkynyloxy group, a lower cycloalkyloxy group, an aryloxy group, a heterocyclic oxy group and —NR$^a$R$^b$;

in the case where $R^7$ and/or $R^8$ is a lower cycloalkyl group, an aryl group, a heterocyclic group, a lower cycloalkyloxy group, an aryloxy group or a heterocyclic oxy group, the lower cycloalkyl group, the aryl group, the heterocyclic group, the lower cycloalkyloxy group, the aryloxy group or the heterocyclic oxy group optionally has one or a plurality of substituents selected from the group consisting of a halogen atom, a lower alkyl group, a halogenated lower alkyl group, an aryl group, a lower alkenyl group, a lower alkynyl group, a lower cycloalkyl group, an aryl group, a heterocyclic group, a hydroxy group, a lower alkoxy group, a halogenated lower alkoxy group, a lower alkenyloxy group, a lower alkynyloxy group, a lower cycloalkyloxy group, an aryloxy group, a heterocyclic oxy group, a mercapto group, a lower alkylthio group, a lower alkenylthio group, a lower alkynylthio group, a lower cycloalkylthio group, an arylthio group, a heterocyclic thio group, a lower alkylcarbonyl group, an arylcarbonyl group, a lower alkoxycarbonyl group, an aryloxycarbonyl group, a lower alkylcarbonyloxy group, an arylcarbonyloxy group, —NR$^a$R$^b$, a nitro group and a cyano group;

$R^a$ and $R^b$ are the same or different and represent a hydrogen atom, a lower alkyl group, a lower alkenyl group, a lower alkynyl group, a lower cycloalkyl group, an aryl group, a heterocyclic group, a lower alkoxycarbonyl group or an aryloxycarbonyl group;

Y represents a lower alkylene group;

p represents 0, 1, 2 or 3, in the case where p is 2 or 3, each $R^6$ is the same or different.

3. The method according to claim 1, wherein in the formula (1), $R^1$ represents a hydrogen atom or a lower alkyl group;

$R^2$ represents a hydrogen atom or a lower alkyl group;

$R^3$ and $R^4$ are the same or different and represent a hydrogen atom or a lower alkyl group;

$R^5$ represents a hydrogen atom or a lower alkyl group;

$R^6$ represents a halogen atom, a lower alkyl group, a hydroxy group or a lower alkoxy group;

X represents —CO—, —C(O)NR$^8$—, —S(O)— or —S(O)$_2$—;

R⁷ and/or R⁸ are the same or different and represent a hydrogen atom, a lower alkyl group, a lower cycloalkyl group, an aryl group, a heterocyclic group, a lower alkoxy group, lower cycloalkyloxy group, an aryloxy group or a heterocyclic oxy group;

in the case where $R^7$ and/or $R^8$ is a lower alkyl group, the lower alkyl group optionally has one or a plurality of substituents selected from the group consisting of a halogen atom and —$NR^aR^b$;

in the case where $R^7$ and/or $R^8$ is a lower cycloalkyl group, an aryl group, a heterocyclic group, a lower cycloalkyloxy group, an aryloxy group or a heterocyclic oxy group, the lower cycloalkyl group, the aryl group, the heterocyclic group, the lower cycloalkyloxy group, the aryloxy group or the heterocyclic oxy group optionally has one or a plurality of substituents selected from the group consisting of a halogen atom, a lower alkyl group, a hydroxy group, a lower alkoxy group, a mercapto group, a lower alkylthio group, a lower alkylcarbonyl group, a lower alkoxycarbonyl group, a lower alkylcarbonyloxy group and a nitro group;

$R^a$ and $R^b$ are the same or different and represent a hydrogen atom or a lower alkyl group;

Y represents a lower alkylene group;

p represents 0, 1, 2 or 3, in the case where p is 2 or 3, each $R^6$ is the same or different.

4. The method according to claim 1, wherein in the formula (I), $R^1$ represents a lower alkyl group;
$R^2$ represents a hydrogen atom;
$R^3$ and $R^4$ represent a lower alkyl group;
$R^5$ represents a lower alkyl group;
$R^6$ represents a halogen atom, a lower alkyl group or a lower alkoxy group;
X represents —CO—, —C(O)NR⁸— or —S(O)₂—;
$R^7$ represents a lower alkyl group, a lower cycloalkyl group, an aryl group, a heterocyclic group, a lower alkoxy group or an aryloxy group;
in the case where $R^7$ is a lower alkyl group, the lower alkyl group optionally has one or a plurality of substituents selected from the group consisting of a halogen atom and —$NR^aR^b$;
in the case where $R^7$ is an aryl group, a heterocyclic group or an aryloxy group, the aryl group, the heterocyclic group or the aryloxy group optionally has one or a plurality of substituents selected from the group consisting of a halogen atom, a lower alkyl group, a lower alkoxy group, a lower alkylthio group, a lower alkylcarbonyl group, a lower alkoxycarbonyl group, a lower alkylcarbonyloxy group and a nitro group;
$R^a$ and $R^b$ are the same or different and represent a hydrogen atom or a lower alkyl group;
$R^8$ represents a hydrogen atom or a lower alkyl group;
Y represents a lower alkylene group;
p represents 0, 1 or 2, in the case where p is 2, each $R^6$ is the same or different.

5. The method according to claim 1, wherein in the formula (I), $R^1$ represents a lower alkyl group;
$R^2$ represents a hydrogen atom;
$R^3$ and $R^4$ represent a lower alkyl group;
$R^5$ represents a lower alkyl group;
$R^6$ represents a halogen atom, a lower alkyl group or a lower alkoxy group;
X represents —CO—, —C(O)NR⁸— or —S(O)₂—;
$R^7$ represents a lower alkyl group, a lower cycloalkyl group, an aryl group, a heterocyclic group, a lower alkoxy group or an aryloxy group;
in the case where $R^7$ is a lower alkyl group, the lower alkyl group optionally has one or a plurality of substituents selected from the group consisting of a halogen atom and —$NR^aR^b$;
in the case where $R^7$ is an aryl group, the aryl group optionally has one or a plurality of substituents selected from the group consisting of a halogen atom, a lower alkyl group, a lower alkoxy group, a lower alkylthio group, a lower alkylcarbonyl group, a lower alkoxycarbonyl group, a lower alkylcarbonyloxy group and a nitro group;
in the case where $R^7$ is a heterocyclic group, the heterocyclic group optionally has one or a plurality of substituents selected from the group consisting of a halogen atom, a lower alkyl group and a lower alkoxy group;
in the case where $R^7$ is an aryloxy group, the aryloxy group optionally has one or a plurality of substituents which are halogen atoms;
$R^a$ and $R^b$ are the same or different and represent a hydrogen atom or a lower alkyl group;
$R^8$ represents a hydrogen atom or a lower alkyl group;
Y represents a lower alkylene group;
p represents 0, 1 or 2, in the case where p is 2, each $R^6$ is the same or different.

6. The method according to claim 1, wherein in the formula (I), $R^1$, $R^3$, $R^4$ and $R^5$ represent a methyl group; $R^2$ represents a hydrogen atom; and Y represents a methylene group.

7. The method according to claim 1, wherein the compound is selected from the group consisting of 6-[4-(furan-2-ylcarbonyloxy)-2-methoxyphenyl]-5-(2-methoxyphenylaminomethyl)-2,2,4-trimethyl-1,2-dihydroquinoline, 6-[2-methoxy-4-(2-methylpyridin-3-ylcarbonyloxy)phenyl]-5-(2-methoxyphenylaminomethyl)-2,2,4-trimethyl-1,2-dihydroquinoline, 6-(4-benzoyloxy-2-methoxyphenyl)-5-(2-methoxyphenylaminomethyl)-2,2,4-trimethyl-1,2-dihydroquinoline, 6-[2-methoxy-4-(2-methoxybenzoyloxy)phenyl]-5-(2-methoxyphenylaminomethyl)-2,2,4-trimethyl-1,2-dihydroquinoline, 6-[2-methoxy-4-(2-methylbenzoyloxy)phenyl]-5-(2-methoxyphenylaminomethyl)-2,2,4-trimethyl-1,2-dihydroquinoline, 6-[4-(furan-3-ylcarbonyloxy)-2-methoxyphenyl]-5-(2-methoxyphenylaminomethyl)-2,2,4-trimethyl-1,2-dihydroquinoline, 5-(2-methoxyphenylaminomethyl)-6-[2-methoxy-4-(thiophen-3-ylcarbonyloxy)phenyl]-2,2,4-trimethyl-1,2-dihydroquinoline, 5-(2-methoxyphenylaminomethyl)-6-[2-methoxy-4-(pyridin-3-ylcarbonyloxy)phenyl]-2,2,4-trimethyl-1,2-dihydroquinoline, 6-[4-(2-chlorobenzoyloxy)-2-methoxyphenyl]-5-(5-fluoro-2-methylphenylaminomethyl)-2,2,4-trimethyl-1,2-dihydroquinoline, 6-[4-(2-chlorobenzoyloxy)-2-methoxyphenyl]-5-(2-methoxyphenylaminomethyl)-2,2,4-trimethyl-1,2-dihydroquinoline, 6-[4-(2-fluorobenzoyloxy)-2-methoxyphenyl]-5-(2-methoxyphenylaminomethyl)-2,2,4-trimethyl-1,2-dihydroquinoline, 5-(2-methoxyphenylaminomethyl)-6-[2-methoxy-4-(pyridin-4-ylcarbonyloxy)phenyl]-2,2,4-trimethyl-1,2-dihydroquinoline, 6-(4-isopropylcarbonyloxy-2-methoxyphenyl)-5-(2-methoxyphenylaminomethyl)-2,2,4-trimethyl-1,2-dihydroquinoline, 5-(2-methoxyphenylaminomethyl)-6-[2-methoxy-4-(thiophen-2-ylcarbonyloxy)phenyl]-2,2,4-trimethyl-1,2-dihydroquinoline, 5-(5-fluoro-2-methylphenylaminomethyl)-6-[2-methoxy-4-(pyridin-3-ylcarbonyloxy)phenyl]-2,2,4-trimethyl-1,2-dihydroquinoline, 5-(5-fluoro-2-methylphenylaminomethyl)-6-[4-(furan-2-ylcarbonyloxy)-2-methoxyphenyl]-2,2,4-trimethyl-1,2-dihydroquinoline, 6-[2-methoxy-4-(3-methoxycarbonylbenzoyloxy)phenyl]-5-(2-methoxyphenylaminomethyl)-2,2,4-trimethyl-1,2-dihydroquinoline, 6-[2-methoxy-4-(4-methoxybenzoyloxy)phenyl]-5-(2-methoxyphenylaminomethyl)-2,2,4-trimethyl-1,2-dihydroquinoline, 6-[4-(4-fluorobenzoyloxy)-2-methoxyphenyl]-5-(2-methoxyphenylaminomethyl)-2,2,4-trimethyl-1,2-dihydroquinoline, 6-[2-methoxy-4-(2-methylthiobenzoyloxy)phenyl]-5-(2-methoxyphenylaminomethyl)-2,2,4-trimethyl-1,2-dihydroquinoline, 6-[4-(3-acetylbenzoyloxy)-2-methoxyphenyl]-5-(2-methoxyphenylaminomethyl)-2,2,4-trimethyl-1,2-dihydroquinoline, 6-[4-(3-chlorothiophen-2-ylcarbonyloxy)-2-methoxyphenyl]-5-(2-methoxyphenylaminomethyl)-2,2,4-trimethyl-1,2-dihydroquinoline, 6-[2-methoxy-4-(3-methylfuran-2-ylcarbonyloxy)phenyl]-5-(2-methoxyphenylaminomethyl)-2,2,4-trimethyl-1,2-dihydroquinoline, 5-(2-methoxyphenylaminomethyl)-6-[2-methoxy-4-(thiazol-4-ylcarbonyloxy)phenyl]-2,2,4-trimethyl-1,2-dihydroquinoline, 6-[2-methoxy-4-(6-methylpyridin-3-ylcarbonyloxy)phenyl]-5-(2-methoxyphenylaminomethyl)-2,2,4-trimethyl-1,2-dihydroquinoline, 6-[2-methoxy-4-(2-methoxypyridin-3-ylcarbonyloxy)phenyl]-5-(2-methoxyphenylaminomethyl)-2,2,4-trimethyl-1,2-dihydroquinoline, 5-(5-fluoro-2-methylphenylaminomethyl)-6-[4-(furan-3-ylcarbonyloxy)-2-methoxyphenyl]-2,2,4-trimethyl-1,2-dihydroquinoline, 5-(5-fluoro-2-methylphenylaminomethyl)-6-[2-methoxy-4-(pyridin-4-ylcarbonyloxy)phenyl]-2,2,4-trimethyl-1,2-dihydroquinoline, 6-[4-(2-fluorobenzoyloxy)-2-methoxyphenyl]-5-(5-fluoro-2-methylphenylaminomethyl)-2,2,4-trimethyl-1,2-dihydroquinoline, 5-(5-fluoro-2-methylphenylaminomethyl)-6-[2-methoxy-4-(2-methylpyridin-3-ylcarbonyloxy)phenyl]-2,2,4-trimethyl-1,2-dihydroquinoline, 5-(5-fluoro-2-methylphenylaminomethyl)-6-[4-(2-methylthiobenzoyloxy)-2-methoxyphenyl]-2,2,4-trimethyl-1,2-dihydroquinoline, 5-(5-fluoro-2-methylphenylaminomethyl)-6-[2-methoxy-4-(2-methoxypyridin-3-ylcarbonyloxy)phenyl]-2,2,4-trimethyl-1,2-dihydroquinoline, 5-(5-fluoro-2-methylphenylaminomethyl)-6-[2-methoxy-4-(3-methylfuran-2-ylcarbonyloxy)phenyl]-2,2,4-trimethyl-1,2-dihydroquinoline, 6-(4-dimethylaminocarbonyloxy-2-methoxyphenyl)-5-(2-methoxyphenylaminomethyl)-2,2,4-trimethyl-1,2-dihydroquinoline, 6-[2-methoxy-4-(morpholin-4-ylcarbonyloxy)phenyl]-5-(2-methoxyphenylaminomethyl)-2,2,4-trimethyl-1,2-dihydroquinoline, 5-(5-fluoro-2-methylphenylaminomethyl)-6-[2-methoxy-4-(morpholin-4-ylcarbonyloxy)phenyl]-2,2,4-trimethyl-1,2-dihydroquinoline, 5-(2-methoxyphenylaminomethyl)-6-(2-methoxy-4-propylsulfonyloxyphenyl)-2,2,4-trimethyl-1,2-dihydroquinoline, 6-(4-isopropylsulfonyloxy-2-methoxyphenyl)-5-(2-methoxyphenylaminomethyl)-2,2,4-trimethyl-1,2-dihydroquinoline, 6-(2-methoxy-4-methylsulfonyloxyphenyl)-5-(2-methoxyphenylaminomethyl)-2,2,4-trimethyl-1,2-dihydroquinoline, 5-(5-fluoro-2-methylphenylaminomethyl)-6-(2-methoxy-4-propylsulfonyloxyphenyl)-2,2,4-trimethyl-1,2-dihydroquinoline, 6-(4-cyclopropylsulfonyloxy-2-methoxyphenyl)-5-(2-methoxyphenylaminomethyl)-2,2,4-trimethyl-1,2-dihydroquinoline, 6-(4-cyclopentylsulfonyloxy-2-methoxyphenyl)-5-(2-methoxyphenylaminomethyl)-2,2,4-trimethyl-1,2-dihydroquinoline, 5-(5-fluoro-2-methylphenylaminomethyl)-6-(2-methoxy-4-methylsulfonyloxyphenyl)-2,2,4-trimethyl-1,2-dihydroquinoline, 6-[4-[N-(2-dimethylaminoethyl)-N-methylaminocarbonyloxy]-2-methoxyphenyl]-5-(2-methoxyphenylaminomethyl)-2,2,4-trimethyl-1,2-dihydroquinoline, 5-(2-methoxyphenylaminomethyl)-6-[2-methoxy-4-(pyridin-3-ylaminocarbonyloxy)phenyl]-2,2,4-trimethyl-1,2-dihydroquinoline, and 6-[4-[N-(2-dimethylaminoethyl)-N-methylaminocarbonyloxy]-2-methoxyphenyl]-5-(5-fluoro-2-methylphenylaminomethyl)-2,2,4-trimethyl-1,2-dihydroquinoline, Or a pharmaceutically acceptable salt thereof.

* * * * *